(12) United States Patent
Kurosawa et al.

(10) Patent No.: US 8,999,673 B2
(45) Date of Patent: Apr. 7, 2015

(54) METHOD FOR SPECIFICALLY PRODUCING A JOINED DNA FRAGMENT COMPRISING A SEQUENCE DERIVED FROM A TARGET GENE

(75) Inventors: Nobuyuki Kurosawa, Toyama (JP); Masaharu Isobe, Toyama (JP)

(73) Assignee: National University Corporation University of Toyama, Toyama-Shi (JP)

( * ) Notice: Subject to any disclaimer, the term of this patent is extended or adjusted under 35 U.S.C. 154(b) by 0 days.

(21) Appl. No.: 13/394,153

(22) PCT Filed: Sep. 2, 2010

(86) PCT No.: PCT/JP2010/064994
§ 371 (c)(1),
(2), (4) Date: Jun. 18, 2012

(87) PCT Pub. No.: WO2011/027808
PCT Pub. Date: Mar. 10, 2011

(65) Prior Publication Data
US 2013/0023009 A1    Jan. 24, 2013

(30) Foreign Application Priority Data

Sep. 4, 2009 (JP) ................................. 2009-205308

(51) Int. Cl.
| | | |
|---|---|---|
| C12P 19/34 | (2006.01) | |
| C12N 15/10 | (2006.01) | |
| C12N 15/66 | (2006.01) | |
| C07H 21/00 | (2006.01) | |
| C07H 21/02 | (2006.01) | |
| C07H 21/04 | (2006.01) | |
| C12N 15/64 | (2006.01) | |
| C12P 21/06 | (2006.01) | |

(52) U.S. Cl.
CPC ............ *C12N 15/10* (2013.01); *C12N 15/1027* (2013.01); *C12N 15/66* (2013.01)

(58) Field of Classification Search
None
See application file for complete search history.

(56) References Cited

U.S. PATENT DOCUMENTS

2002/0028444 A1 * 3/2002 Harney et al. ................. 435/6
2003/0162265 A1 * 8/2003 Evans et al. ................ 435/91.2

FOREIGN PATENT DOCUMENTS

WO           03/091440     11/2003
WO    WO 03/091440 A1     11/2003

OTHER PUBLICATIONS

Cha-aim et al., "Reliable fusion PCR mediated by GC-rich overlap sequences" 434 Gene 43-49 (Apr. 2009).*

International Preliminary Report on Patentability (Chapter I of the Patent cooperation Treaty) with Written Opinion for corresponding International Application No. PCT/JP2010/064994, Mar. 15, 2012.
Notification of transmittal of translation of the International Preliminary Report on Patentability for corresponding International Application No. PCT/JP2010/064994, Apr. 19, 2012.
Shevchuk, N.A. et al., Construction of long DNA molecules using long PCR-based fusion of several fragments simultaneously, Nucleic Acids Research, 2004, vol. 32, No. 2 e19, published Jan. 22, 2004.
Nagy, Z.B, et al., Assembling and cloning genes for fusion proteins using reverse transcription one-step overlap extension PCR method, Anal. Biochem., 2006, 351(2), p. 311-313.
H.-X. LilAO et al., Journal of Virological Methods, 158, (2009), pp. 171-179.
International Search Report for corresponding International Application No. PCT/JP2010/064994, Dec. 14, 2010.
Nobuyuki Kurosawa et al., "Target-selective homologous recombination cloning for high-throughput generation of monoclonal antibodies from single plasma cells", BMC Biotechnology, Biomed Central Ltd. London, GB, vol. 11, No. 1, Apr. 13, 2011, p. 39, XP021097757.
Megumi Yoshioka et al., "Target-selective joint polymerase chain reaction: A robust and rapid method for high-throughput production of recombinant monoclonal antibodies from single cells", BMC Biotechnology, Biomed Central Ltd. London, GB, vol. 11, No. 1, Jul. 21, 2011, p. 75, XP021105285.
Chinese Office Action for corresponding CN Application No. 201080039384.8, Jul. 30, 2013.
Chinese Office Action for related Chinese Application No. 201080039384.8, dated Apr. 21, 2014, with English-language translation, 15 pages.
Office Action for corresponding Japanese Patent Application No. 2011-529928, dated Nov. 18, 2014, 5 pages.
Patent Examination Report No. 1 for corresponding Australian Application No. 2010290426, dated Aug. 25, 2014, 3 pages.

* cited by examiner

*Primary Examiner* — Celine Qian
*Assistant Examiner* — Nancy J Leith
(74) *Attorney, Agent, or Firm* — Ditthavong & Steiner, P.C.

(57) ABSTRACT

Provided is a method for selectively obtaining, for a given target gene, a "joined DNA fragment" wherein just a target gene fragment is joined with desired other DNA fragments, regardless of whether a DNA fragment containing a target gene sequence has been purified. In the provided method, a double-stranded joining DNA fragment containing a sequence A and/or a sequence B is selectively joined to the ends of a target gene fragment. A mixture of a double-stranded gene fragment, the 3' end of which is protruding, and the double-stranded joining DNA fragment, which are related in a prescribed manner, undergoes at least two cycles of thermal denaturation, reassociation, and DNA synthesis, resulting in a "joined DNA fragment," which is a double-stranded DNA fragment including at least one instance of a sequence resulting from joining sequence A, the target gene sequence, and sequence B. A "single-side joined DNA fragment" can also be obtained, by a similar method.

31 Claims, 13 Drawing Sheets

Fig. 9

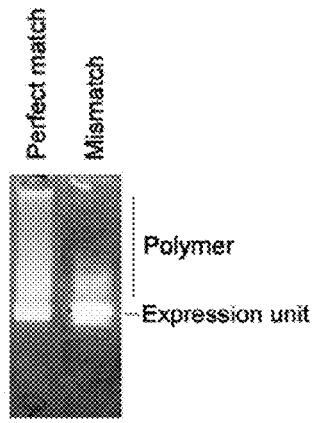

Fig. 10

```
                Primer A                      Internal sequence
CTTCGAATTCTGCAGTCGACGGTACCGCGGGCCCGGGATCCCCCCCCCCCGACATAACAACCAGAATCCTCCTCTAAAG
AAGCACCTGGGAGCACAGCTCATCACCATGGACTGGACCTGGAGGTTCCTCTTTGTGGTGGCAGCAGCTACAGGTGTCCA
GTCCCAGGTCCAGCTGGTGCAATCTGGGGCTGAGGTGAAGAAGCCTGGGTCCTCGGTGAAGATCTCCTGCAAGGCTTCTG
GAGGCACCTTCAGCAGCTATACTTTCACCTGGGTGCGACAGGCCCCTGGACAAGGGCTTGAGTGGATGGGAAGGATCATC
CCCAATGTCGGTATAGCAAACTACGCACAGAAGTTCCAGGGCAGAGTCACGCTTATCGCGGACAAATTCACGAATTCAAC
GTACATGGAGCTGAGCAGCCTGAGATCTGATGACACGGCCGTTTATTTTTGTGCCGGAGACCCCTCGGGCCACTCACATG
ACTACTGGGGCCAAGGAACCCTGGTCACCGTCTCCTCAGCTTCCACCAAGGGCCCATCCGTCTTCCCCCTGGCGCCCTGC
TCCAGGAGCACCTCCGAGAGCACAGCCGCCCTGGGCTGCCTGGTCAAGGACTACTTCCCCGAACCGGTGACGGTGTCGTG
GAACTCAGGCGCCCTGACCAGCGGCGTGCACACCTTCCCGGCT
       Internal sequence           Primer B
```

(SEQ ID NO: 1)

Fig. 11

(SEQ ID NO: 4)

Fig. 12

(SEQ ID NO: 8)

(SEQ ID NO: 8)

SEQUENCE LISTING

<160> NUMBER OF SEQ ID NOS: 25

<210> SEQ ID NO 1
<211> LENGTH: 683
<212> TYPE: DNA
<213> ORGANISM: Artificial Sequence
<220> FEATURE:
<223> OTHER INFORMATION: Description of Artificial Sequence: Synthetic
      gene fragment polynucleotide

<400> SEQUENCE: 1
ctccgaattc tgcagtcgac ggtaccgcgg gcccgggatc ccccccccc cgacataaca      60 accagaatcc tcctctaaag aagcacctgg gagcacagct catcaccatg gactggacct    120
ggaggttcct ctttgtggtg gcagcagcta caggtgtcca gtcccaggtc cagctggtgc    180
aatctggggc tgaggtgaag aagcctgggt cctcggtgaa gatctcctgc aaggcttctg    240

```
gaggcacctt cagcagctat actttcacct gggtgcgaca ggcccctgga caagggcttg    300
agtggatggg aaggatcatc cccaatgtcg gtatagcaaa ctacgcacag aagttccagg    360
gcagagtcac gcttatcgcg gacaaattca cgaattcaac gtacatggag ctgagcagcc    420
tgagatctga tgacacggcc gtttattttt gtgccgagag cccctcgggc cactcacatg    480
actactgggg ccaaggaacc ctggtcaccg tctcctcagc ttccaccaag ggcccatccg    540 tcttcccccct ggcgccctgc tccaggagca cctccgagag cacagccgcc ctgggctgcc    600
tggtcaagga ctacttcccc gaaccggtga cggtgtcgtg gaactcaggc gccctgacca    660
gcggcgtgca ccttcccg gct                                              683
```

`<210>` SEQ ID NO 2
`<211>` LENGTH: 38
`<212>` TYPE: DNA
`<213>` ORGANISM: Artificial Sequence
`<220>` FEATURE:
`<223>` OTHER INFORMATION: Description of Artificial Sequence: Synthetic
       primer

`<400>` SEQUENCE: 2

```
ctccgaattc tgcagtcgac ggtaccgcgg gcccggga                              38
```

`<210>` SEQ ID NO 3
`<211>` LENGTH: 25
`<212>` TYPE: DNA
`<213>` ORGANISM: Artificial Sequence
`<220>` FEATURE:
`<223>` OTHER INFORMATION: Description of Artificial Sequence: Synthetic
       primer

`<400>` SEQUENCE: 3

```
agccgggaag gtgtgcacgc cgctg                                           25
```

`<210>` SEQ ID NO 4
`<211>` LENGTH: 628
`<212>` TYPE: DNA
`<213>` ORGANISM: Artificial sequence
`<220>` FEATURE:
`<223>` OTHER INFORMATION: Description of Artificial Sequence: Synthetic
       gene fragment polynucleotide

`<400>` SEQUENCE: 4

```
cttcgaattc tgcagtcgac ggtaccgcgg gcccgggatc caccggtcgc caccatggtg    60
agcaagggcg aggagctgtt caccggggtg gtgcccatcc tggtcgagct ggacggcgac   120
gtaaacggcc acaagttcag cgtgtccggc gagggcgagg gcgatgccac ctacggcaag   180
ctgaccctga agttcatctg caccaccggc aagctgcccg tgccctggcc cacccctgtg   240
accaccctga cctacggcgt gcagtgcttc agccgctacc ccgaccacat gaagcagcac   300
gacttcttca gtccgccat gcccgaaggc tacgtccagg agcgcaccat cttcttcaag   360
gacgacggca actacaagac ccgcgccgag gtgaagttcg agggcgacac cctggtgaac   420
cgcatcgagc tgaagggcat cgacttcaag gaggacggca acatcctggg gcacaagctg   480
gagtacaact acaacagcca caacgtctat atcatggccg acaagcagaa gaacggcatc   540
aaggtgaact tcaagatccg ccacaacatc gaggacggca gcgtgcagct cgccgaccac   600
taccagcggc gtgcacacct tcccggct                                        628
```

`<210>` SEQ ID NO 5
`<211>` LENGTH: 3533

<212> TYPE: DNA
<213> ORGANISM: Artificial sequence
<220> FEATURE:
<223> OTHER INFORMATION: Description of Artificial Sequence: Synthetic gene fragment polynucleotide

<400> SEQUENCE: 5

| | | | | | | |
|---|---|---|---|---|---|---|
| tagttattaa | tagtaatcaa | ttacggggtc | attagttcat | agcccatata | tggagttccg | 60 |
| cgttacataa | cttacggtaa | atggcccgcc | tggctgaccg | cccaacgacc | cccgcccatt | 120 |
| gacgtcaata | atgacgtatg | ttcccatagt | aacgccaata | gggactttcc | attgacgtca | 180 |
| atgggtggag | tatttacggt | aaactgccca | cttggcagta | catcaagtgt | atcatatgcc | 240 |
| aagtacgccc | cctattgacg | tcaatgacgg | taaatggccc | gcctggcatt | atgcccagta | 300 |
| catgacctta | tgggactttc | ctacttggca | gtacatctac | gtattagtca | tcgctattac | 360 |
| catggtgatg | cggttttggc | agtacatcaa | tgggcgtgga | tagcggtttg | actcacgggg | 420 |
| atttccaagt | ctccacccca | ttgacgtcaa | tgggagtttg | ttttggcacc | aaaatcaacg | 480 |
| ggactttcca | aaatgtcgta | acaactccgc | cccattgacg | caaatgggcg | gtaggcgtgt | 540 |
| acggtgggag | gtctatataa | gcagagctgg | tttagtgaac | cgtcagatcc | gctagcgcta | 600 |
| ccggactcag | atctcgagct | caagcttcga | attctgcagt | cgacggtacc | gcgggcccgg | 660 |
| gatccccccc | cccccgata | tctaaataca | ttcaaatatg | tatccgctca | tgagacaata | 720 |
| accctgataa | atgcttcaat | aatattgaaa | aggaagagt | atgagtattc | aacatttccg | 780 |
| tgtcgccctt | attcccttt | ttgcggcatt | ttgccttcct | gttttgctc | acccagaaac | 840 |
| gctggtgaaa | gtaaaagatg | ctgaagatca | gttgggtgca | cgagtgggtt | acatcgaact | 900 |
| ggatctcaac | agcggtaaga | tccttgagag | ttttcgcccc | gaagaacgtt | ttccaatgat | 960 |
| gagcactttt | aaagttctgc | tatgtggcgc | ggtattatcc | cgtattgacg | ccgggcaaga | 1020 |
| gcaactcggt | cgccgcatac | actattctca | gaatgacttg | gttgagtact | caccagtcac | 1080 |
| agaaaagcat | cttacggatg | gcatgacagt | aagagaatta | tgcagtgctg | ccataaccat | 1140 |
| gagtgataac | actgcggcca | acttacttct | gacaacgatc | ggaggaccga | aggagctaac | 1200 |
| cgcttttttg | cacaacatgg | gggatcatgt | aactcgcctt | gatcgttggg | aaccggagct | 1260 |
| gaatgaagcc | ataccaaacg | acgagcgtga | caccacgatg | cctgtagcaa | tggcaacaac | 1320 |
| gttgcgcaaa | ctattaactg | gcgaactact | tactctagct | tcccggcaac | aattaataga | 1380 |
| ctggatggag | gcggataaag | ttgcaggacc | acttctgcgc | tcggcccttc | cggctggctg | 1440 |
| gtttattgct | gataaatctg | gagccggtga | gcgtgggtct | cgcggtatca | ttgcagcact | 1500 |
| ggggccagat | ggtaagccct | cccgtatcgt | agttatctac | acgacgggga | gtcaggcaac | 1560 |
| tatggatgaa | cgaaatagac | agatcgctga | gataggtgcc | tcactgatta | agcattggta | 1620 |
| actgtcagac | caagtttact | catatatact | ttagattgat | ttaaaacttc | attttttaatt | 1680 |
| taaaaggatc | taggtgaaga | tccttttttga | taatctcatg | accaaaatcc | cttaacgtga | 1740 |
| gttttcgttc | cactgagcgt | cagacccccgt | agaaaagatc | aaaggatctt | cttgagatcc | 1800 |
| tttttttctg | cgcgtaatct | gctgcttgca | aacaaaaaaa | ccaccgctac | cagcggtggt | 1860 |
| ttgtttgccg | gatcaagagc | taccaactct | ttttccgaag | gtaactggct | tcagcagagc | 1920 |
| gcagatacca | aatactgttc | ttctagtgta | gccgtagtta | ggccaccact | tcaagaactc | 1980 |
| tgtagcaccg | cctacatacc | tcgctctgct | aatcctgtta | ccagtggctg | ctgccagtgg | 2040 |
| cgataagtcg | tgtcttaccg | ggttggactc | aagacgatag | ttaccggata | aggcgcagcg | 2100 |
| gtcgggctga | acggggggtt | cgtgcacaca | gcccagcttg | gagcgaacga | cctacaccga | 2160 |

```
actgagatac ctacagcgtg agctatgaga aagcgccacg cttcccgaag ggagaaaggc    2220
ggacaggtat ccggtaagcg gcagggtcgg aacaggagag cgcacgaggg agcttccagg    2280
gggaaacgcc tggtatcttt atagtcctgt cgggtttcgc cacctctgac ttgagcgtcg    2340 attttttgtga tgctcgtcag gggggcgagc cctatggaaa aacgccagca acgcggcctt   2400
tttacggttc ctggccgata tcacgtggaa ctcaggcgcc ctgaccagcg gcgtgcacac    2460
cttcccggct gtcctacagt cctcaggact ctactccctc agcagcgtgg tgaccgtgcc    2520
ctccagcagc ttgggcaccc agacctacac ctgcaacgtg aatcacaagc ccagcaacac    2580
caaggtggac aagagagttg agcccaaatc ttgtgacaaa actcacacat gcccaccgtg    2640
cccagcacct gaactcctgg ggggaccgtc agtcttcctc ttccccccaa acccaagga    2700 caccctcatg atctcccgga cccctgaggt cacatgcgtg gtggtggacg tgagccacga    2760
agaccctgag gtcaagttca actggtacgt ggacggcgtg gaggtgcata atgccaagac    2820
aaagccgcgg gaggagcagt acaacagcac gtaccgtgtg gtcagcgtcc tcaccgtcct    2880
gcaccaggac tggctgaatg gcaaggagta caagtgcaag gtctccaaca agccctccc     2940 agcccccatc gagaaaacca tctccaaagc caaagggcag ccccgagaac acaggtgta    3000 caccctgccc ccatcccggg atgagctgac caagaaccag gtcagcctga cctgcctggt    3060
caaaggcttc tatcccagcg acatcgccgt ggagtgggag agcaatgggc agccggagaa    3120
caactacaag accacgcctc ccgtgctgga ctccgacggc tccttcttcc tctacagcaa    3180
gctcaccgtg gacaagagca ggtggcagca ggggaacgtc ttctcatgct ccgtgatgca    3240
tgagggtctg cacaaccact acacgcagaa gagcctctcc ctgtctccgg gtaaatgagt    3300
gcgacggcgg ccgcgactct agatcataat cagccatacc acatttgtag aggttttact    3360
tgctttaaaa aacctcccac acctccccct gaacctgaaa cataaaatga atgcaattgt    3420
tgttgttaac ttgtttattg cagcttataa tggttacaaa taaagcaata gcatcacaaa    3480
tttcacaaat aaagcatttt tttcactgca ttctagttgt ggtttgtcca aac           3533
```

<210> SEQ ID NO 6
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 6

```
gggggggggg ggggggatc ccgg                                            24
```

<210> SEQ ID NO 7
<211> LENGTH: 25
<212> TYPE: DNA
<213> ORGANISM: Artificial sequence
<220> FEATURE:
<223> OTHER INFORMATION: Description of Artificial Sequence: Synthetic
      primer

<400> SEQUENCE: 7

```
cgtggaactc aggcgccctg accag                                          25
```

<210> SEQ ID NO 8
<211> LENGTH: 1797
<212> TYPE: DNA
<213> ORGANISM: Artificial sequence
<220> FEATURE:

<223> OTHER INFORMATION: Description of Artificial Sequence: Synthetic
      gene fragment polynucleotide

<400> SEQUENCE: 8

| | | | | | |
|---|---|---|---|---|---|
| cgtggaactc | aggcgccctg | accagcggcg | tgcacacctt | cccggctgtc | ctacagtcct | 60 |
| caggactcta | ctccctcagc | agcgtggtga | ccgtgccctc | cagcagcttg | ggcacccaga | 120 |
| cctacacctg | caacgtgaat | cacaagccca | gcaacaccaa | ggtggacaag | agagttgagc | 180 |
| ccaaatcttg | tgacaaaact | cacacatgcc | caccgtgccc | agcacctgaa | ctcctggggg | 240 |
| gaccgtcagt | cttcctcttc | cccccaaaac | ccaaggacac | cctcatgatc | tcccggaccc | 300 |
| ctgaggtcac | atgcgtggtg | gtggacgtga | gccacgaaga | ccctgaggtc | aagttcaact | 360 |
| ggtacgtgga | cggcgtggag | gtgcataatg | ccaagacaaa | gccgcgggag | gagcagtaca | 420 |
| acagcacgta | ccgtgtggtc | agcgtcctca | ccgtcctgca | ccaggactgg | ctgaatggca | 480 |
| aggagtacaa | gtgcaaggtc | tccaacaaag | ccctcccagc | ccccatcgag | aaaaccatct | 540 |
| ccaaagccaa | agggcagccc | cgagaaccac | aggtgtacac | cctgccccca | tcccgggatg | 600 |
| agctgaccaa | gaaccaggtc | agcctgacct | gcctggtcaa | aggcttctat | cccagcgaca | 660 |
| tcgccgtgga | gtgggagagc | aatgggcagc | cggagaacaa | ctacaagacc | acgcctcccg | 720 |
| tgctggactc | cgacggctcc | ttcttcctct | acagcaagct | caccgtggac | aagagcaggt | 780 |
| ggcagcaggg | gaacgtcttc | tcatgctccg | tgatgcatga | gggtctgcac | aaccactaca | 840 |
| cgcagaagag | cctctccctg | tctccgggta | aatgagtgcg | acggcggcca | agtcgacttg | 900 |
| gccgactcta | gatcataatc | agccatacca | catttgtaga | ggttttactt | gctttaaaaa | 960 |
| acctcccaca | cctccccctg | aacctgaaac | ataaaatgaa | tgcaattgtt | gttgttaact | 1020 |
| tgtttattgc | agcttataat | ggttacaaat | aaagcaatag | catcacaaat | ttcacaaata | 1080 |
| aagcattttt | ttcactgcat | tctagttgtg | gtttgtccaa | actagttatt | aatagtaatc | 1140 |
| aattacgggg | tcattagttc | atagcccata | tatggagttc | cgcgttacat | aacttacggt | 1200 |
| aaatggcccg | cctggctgac | cgcccaacga | cccccgccca | ttgacgtcaa | taatgacgta | 1260 |
| tgttcccata | gtaacgccaa | tagggacttt | ccattgacgt | caatgggtgg | agtatttacg | 1320 |
| gtaaactgcc | cacttggcag | tacatcaagt | gtatcatatg | ccaagtacgc | ccctattga | 1380 |
| cgtcaatgac | ggtaaatggc | ccgcctggca | ttatgcccag | tacatgacct | tatgggactt | 1440 |
| tcctacttgg | cagtacatct | acgtattagt | catcgctatt | accatggtga | tgcggttttg | 1500 |
| gcagtacatc | aatgggcgtg | atagcggtt | tgactcacgg | ggatttccaa | gtctccaccc | 1560 |
| cattgacgtc | aatgggagtt | tgttttggca | ccaaaatcaa | cgggactttc | caaaatgtcg | 1620 |
| taacaactcc | gccccattga | cgcaaatggg | cggtaggcgt | gtacggtggg | aggtctatat | 1680 |
| aagcagagct | ggtttagtga | accgtcagat | ccgctagcgc | taccggactc | agatctcgag | 1740 |
| ctcaagcttc | gaattctgca | gtcgacggta | ccgcgggccc | gggatccccc | cccccc | 1797 |

<210> SEQ ID NO 9
<211> LENGTH: 37
<212> TYPE: DNA
<213> ORGANISM: Artificial sequence
<220> FEATURE:
<223> OTHER INFORMATION: Description of Artificial Sequence: Synthetic
      primer

<400> SEQUENCE: 9
agagaagatc ttagttatta atagtaatca attacgg         37

```
<210> SEQ ID NO 10
<211> LENGTH: 37
<212> TYPE: DNA
<213> ORGANISM: Artificial sequence
<220> FEATURE:
<223> OTHER INFORMATION: Description of Artificial Sequence: Synthetic
      primer

<400> SEQUENCE: 10
aaggaagatc tggacaaacc acaactagaa tgcagtg                              37

<210> SEQ ID NO 11
<211> LENGTH: 26
<212> TYPE: DNA
<213> ORGANISM: Artificial sequence
<220> FEATURE:
<223> OTHER INFORMATION: Description of Artificial Sequence: Synthetic
      primer

<400> SEQUENCE: 11
tagttattaa tagtaatcaa ttacgg                                         26

<210> SEQ ID NO 12
<211> LENGTH: 27
<212> TYPE: DNA
<213> ORGANISM: Artificial sequence
<220> FEATURE:
<223> OTHER INFORMATION: Description of Artificial Sequence: Synthetic
      primer

<400> SEQUENCE: 12
tggacaaacc acaactagaa tgcagtg                                        27

<210> SEQ ID NO 13
<211> LENGTH: 35
<212> TYPE: DNA
<213> ORGANISM: Artificial sequence
<220> FEATURE:
<223> OTHER INFORMATION: Description of Artificial Sequence: Synthetic
      primer
<220> FEATURE:
<221> NAME/KEY: misc_feature
<222> LOCATION: (35)..(35)
<223> OTHER INFORMATION: a, c, g, or t

<400> SEQUENCE: 13
cggtaccgcg ggcccgggat ccccccccccc cccdn                              35

<210> SEQ ID NO 14
<211> LENGTH: 27
<212> TYPE: DNA
<213> ORGANISM: Artificial sequence
<220> FEATURE:
<223> OTHER INFORMATION: Description of Artificial Sequence: Synthetic
      primer

<400> SEQUENCE: 14
acgctgctga gggagtagag tcctgag                                        27

<210> SEQ ID NO 15
<211> LENGTH: 25
<212> TYPE: DNA
<213> ORGANISM: Artificial sequence
<220> FEATURE:
<223> OTHER INFORMATION: Description of Artificial Sequence: Synthetic
      primer

<400> SEQUENCE: 15
```
ctttggcctc tctgggatag aagtt                                         25

<210> SEQ ID NO 16
<211> LENGTH: 30
<212> TYPE: DNA
<213> ORGANISM: Artificial sequence
<220> FEATURE:
<223> OTHER INFORMATION: Description of Artificial Sequence: Synthetic
      primer

<400> SEQUENCE: 16
acaacagagg cagttccaga tttcaactgc                                    30

<210> SEQ ID NO 17
<211> LENGTH: 25
<212> TYPE: DNA
<213> ORGANISM: Artificial sequence
<220> FEATURE:
<223> OTHER INFORMATION: Description of Artificial Sequence: Synthetic
      primer

<400> SEQUENCE: 17
catcttcccg ccatctgatg agcag                                         25

<210> SEQ ID NO 18
<211> LENGTH: 2976
<212> TYPE: DNA
<213> ORGANISM: Artificial sequence
<220> FEATURE:
<223> OTHER INFORMATION: Description of Artificial Sequence: Synthetic
      gene fragment polynucleotide

<400> SEQUENCE: 18
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacggtacc gcgggcccgg    660
gatcccccgc ccccccgata tctaaataca ttcaaatatg tatccgctca tgagacaata    720
accctgataa atgcttcaat aatattgaaa aaggaagagt atgagtattc aacatttccg    780
tgtcgccctt attccctttt ttgcggcatt ttgccttcct gttttttgctc acccagaaac    840 gctggtgaaa gtaaaagatg ctgaagatca gttgggtgca cgagtgggtt acatcgaact    900
ggatctcaac agcggtaaga tccttgagag ttttcgcccc gaagaacgtt ttccaatgat    960
gagcactttt aaagttctgc tatgtggcgc ggtattatcc cgtattgacg ccgggcaaga   1020
gcaactcggt cgccgcatac actattctca gaatgacttg gttgagtact caccagtcac   1080
agaaaagcat cttacggatg gcatgacagt aagagaatta tgcagtgctg ccataaccat   1140
gagtgataac actgcggcca acttacttct gacaacgatc ggaggaccga aggagctaac   1200

```
cgcttttttg cacaacatgg gggatcatgt aactcgcctt gatcgttggg aaccggagct    1260
gaatgaagcc ataccaaacg acgagcgtga caccacgatg cctgtagcaa tggcaacaac    1320
gttgcgcaaa ctattaactg gcgaactact tactctagct tcccggcaac aattaataga    1380
ctggatggag gcggataaag ttgcaggacc acttctgcgc tcggcccttc cggctggctg    1440
gtttattgct gataaatctg gagccggtga gcgtgggtct cgcggtatca ttgcagcact    1500
ggggccagat ggtaagccct cccgtatcgt agttatctac acgacgggga gtcaggcaac    1560
tatggatgaa cgaaatagac agatcgctga gataggtgcc tcactgatta agcattggta    1620
actgtcagac caagtttact catatatact ttagattgat ttaaaacttc atttttaatt    1680
taaaaggatc taggtgaaga tcctttttga taatctcatg accaaaatcc cttaacgtga    1740
gttttcgttc cactgagcgt cagacccccgt agaaaagatc aaaggatctt cttgagatcc    1800 ttttttttctg cgcgtaatct gctgcttgca acaaaaaaaa ccaccgctac cagcggtggt    1860
ttgtttgccg gatcaagagc taccaactct ttttccgaag gtaactggct tcagcagagc    1920
gcagatacca atactgttc ttctagtgta gccgtagtta ggccaccact tcaagaactc    1980
tgtagcaccg cctacatacc tcgctctgct aatcctgtta ccagtggctg ctgccagtgg    2040
cgataagtcg tgtcttaccg ggttggactc aagacgatag ttaccggata aggcgcagcg    2100
gtcgggctga acgggggggtt cgtgcacaca gcccagcttg gagcgaacga cctacaccga    2160
actgagatac ctacagcgtg agctatgaga aagcgccacg cttcccgaag ggagaaaggc    2220
ggacaggtat ccggtaagcg gcagggtcgg aacaggagag cgcacgaggg agcttccagg    2280
gggaaacgcc tggtatcttt atagtcctgt cgggtttcgc cacctctgac ttgagcgtcg    2340
atttttgtga tgctcgtcag ggggggcggag cctatggaaa aacgccagca acgcggcctt    2400
tttacggttc ctggccgata tcacgtgcgc atcttcccgc catctgatga gcagttgaaa    2460
tctggaactg cctctgttgt gtgcctgctg aataacttct atcccagaga ggccaaagta    2520
cagtggaagg tggataacgc cctccaatcg ggtaactccc aggagagtgt cacagagcag    2580
gacagcaagg acagcaccta cagcctcagc agcaccctga cgctgagcaa agcagactac    2640
gagaaacaca aagtctacgc ctgcgaagtc acccatcagg gcctgagctc gcccgtcaca    2700
aagagcttca cagggggaga gtgttagagg gagaagtgcg gccaagtcga cttggccgac    2760
tctagatcat aatcagccat accacatttg tagaggtttt acttgcttta aaaaacctcc    2820
cacacctccc cctgaacctg aaacataaaa tgaatgcaat tgttgttgtt aacttgttta    2880
ttgcagctta taatggttac aaataaagca atagcatcac aaatttcaca aataaagcat    2940
ttttttcact gcattctagt tgtggtttgt ccaaac    2976
```

<210> SEQ ID NO 19
<211> LENGTH: 1222
<212> TYPE: DNA
<213> ORGANISM: Artificial sequence
<220> FEATURE:
<223> OTHER INFORMATION: Description of Artificial Sequence: Synthetic
      gene fragment polynucleotide

<400> SEQUENCE: 19

```
catcttcccg ccatctgatg agcagttgaa atctggaact gcctctgttg tgtgcctgct      60
gaataacttc tatcccagag aggccaaagt acagtggaag gtggataacg ccctccaatc     120
gggtaactcc caggagagtg tcacagagca ggacagcaag gacagcacct acagcctcag     180
cagcaccctg acgctgagca aagcagacta cgagaaacac aaagtctacg cctgcgaagt     240
```

```
cacccatcag ggcctgagct cgcccgtcac aaagagcttc aacagggag  agtgttagag    300 ggagaagtgc ggccaagtcg acttggccga ctctagatca taatcagcca taccacattt    360
gtagaggttt tacttgcttt aaaaaacctc ccacacctcc ccctgaacct gaaacataaa    420
atgaatgcaa ttgttgttgt taacttgttt attgcagctt ataatggtta caaataaagc    480
aatagcatca caaatttcac aaataaagca ttttttttcac tgcattctag ttgtggtttg   540
tccaaactag ttattaatag taatcaatta cggggtcatt agttcatagc ccatatatgg    600
agttccgcgt tacataactt acggtaaatg gcccgcctgg ctgaccgccc aacgacccccc  660 gcccattgac gtcaataatg acgtatgttc ccatagtaac gccaataggg actttccatt    720
gacgtcaatg ggtggagtat ttacggtaaa ctgcccactt ggcagtacat caagtgtatc   780
atatgccaag tacgcccccct attgacgtca atgacggtaa atggcccgcc tggcattatg   840
cccagtacat gaccttatgg gactttccta cttggcagta catctacgta ttagtcatcg   900
ctattaccat ggtgatgcgg ttttggcagt acatcaatgg gcgtggatag cggtttgact    960
cacggggatt tccaagtctc caccccattg acgtcaatgg gagtttgttt tggcaccaaa   1020
atcaacggga ctttccaaaa tgtcgtaaca actccgcccc attgacgcaa atgggcggta    1080
ggcgtgtacg gtgggaggtc tatataagca gagctggttt agtgaaccgt cagatccgct    1140
agcgctaccg gactcagatc tcgagctcaa gcttcgaatt ctgcagtcga cggtaccgcg    1200
ggcccgggat cccccccccc cc                                             1222

<210> SEQ ID NO 20
<211> LENGTH: 5
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(5)
<223> OTHER INFORMATION: a, c, t, g, unknown or other

<400> SEQUENCE: 20 nnnnn                                                                  5

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gggggggggg g                                                          11

<210> SEQ ID NO 22
<211> LENGTH: 9
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22 ccccccccc                                                              9

<210> SEQ ID NO 23
```

```
<211> LENGTH: 8
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23 gggggggg                                                              8

<210> SEQ ID NO 24
<211> LENGTH: 5
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24 ggggg                                                                 5

<210> SEQ ID NO 25
<211> LENGTH: 5
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25 ccccc                                                                 5
```

METHOD FOR SPECIFICALLY PRODUCING A JOINED DNA FRAGMENT COMPRISING A SEQUENCE DERIVED FROM A TARGET GENE

CROSS REFERENCE TO RELATED APPLICATIONS

This application claims benefit of priority to Japanese Patent Application No. 2009-205308 filed on Sep. 4, 2009, which is expressly incorporated herein by reference in its entirety.

The instant application contains a Sequence Listing which has been submitted electronically in ASCII format and is hereby incorporated by reference in its entirety. Said ASCII copy, created on Feb. 10, 2014, is named P6227US00_SL.txt and is 20,148 bytes in size.

TECHNICAL FIELD

The present invention relates to a method for specifically producing a joined DNA fragment containing a sequence derived from a target gene, and more particularly, to a method for specifically producing a target gene fragment for specific joining to another desired DNA fragment in the presence of nonspecifically amplified DNA fragments. More particularly, the present invention relates to: (1) a method for producing a "joined DNA fragment" by using a total of two types of DNA fragments comprised of a 3' end protruding double-stranded gene fragment containing the sequence of a target gene and a double-stranded joining DNA fragment having on the two termini thereof the inherent base sequences of the termini of the target gene, and causing the double stranded joining DNA fragments to specifically join to both termini of the target gene fragment; (2) a method for producing a "joined DNA fragment" by using a total of three types of DNA fragments, comprised of a 3' end protruding double-stranded gene fragment containing the sequence of a target gene, and two types of double-stranded DNA fragments, each having on one terminus thereof an inherent base sequence of one terminus of the target gene, respectively, and causing the double-stranded joining DNA fragments to specifically join to both termini of the target gene fragment; and (3) a method for producing a "single-end joined DNA fragment" by using a total of two types of DNA fragments comprised of a 3' end protruding double-stranded gene fragment containing the sequence of a target gene and a double-stranded joining DNA fragment having on one terminus thereof the inherent base sequence of one terminus of the target gene, and causing the double-stranded joining DNA fragment to specifically join to one terminus of the target gene fragment.

BACKGROUND ART

The term "DNA cloning" generally refers to the technique of binding a gene fragment to a vector having the ability to self-replicate, such as a plasmid, phage, or cosmid, introducing the product into a host such as Escherichia coli (E. coli), and causing the host to proliferate to produce the same gene cluster. Cloning and subcloning in E. coli is conducted by the method of binding a target gene fragment that has been amplified by a method such as polymerase chain reaction (PCR) with a vector having a replication origin and an antibiotic selective marker by using DNA ligase and introducing the product into E. coli cells. Subsequently, the cloned bacteria can be sorted by checking for resistance to the antibiotic.

Existing DNA cloning methods are limited by the fact that the DNA that is inserted and the vector must be cleaved with a restriction enzyme recognizing the same site in both, the fact that a restriction enzyme must be selected that does not cleave the interior of the inserted DNA or the vector, and the like.

In recent years, homologous recombination techniques and site-specific recombination techniques employing sequence-specific genetically modified enzymes that promote the recombination of DNA fragments by recognizing specific base sequences have been employed in the cloning of target gene fragments. They have also begun to be widely used to rapidly clone large quantities of genes and express proteins without processing with restriction enzymes or the like.

However, even when employing homologous recombination techniques, the steps of amplifying plasmids with microorganisms such as E. coli and purifying are still necessary. The operation is still tedious and lacks economy.

The joint polymerase chain reaction (jPCR) is known as a method of producing gene clusters having an identical base sequence by joining a target gene fragment with one or more DNA fragments having a specific function other than the target gene under conditions permitting the expression of the function (see Patent Reference 1 and Non-patent References 1 and 2). Here, the term "DNA fragments having a specific function other than the target gene" means a promoter sequence and a polyadenylation signal.

In the method described in Patent Reference 1, three DNA fragments independently containing a promoter sequence, target gene sequence, and polyadenylation signal are PCR amplified with RNA-DNA chimera primers. The amplified DNA fragments are processed with RNase to remove the RNA primer sites. The complementarity of the 3' protruding regions produced on the termini of the individual DNA fragments is utilized to combine the three DNA fragments using DNA ligase. PCR conducted using this product as a template then permits the production of a large quantity of joined DNA in which the three DNA fragments are functionally joined in the order of promoter sequence, target gene sequence, and polyadenylation signal (see Patent Reference 1).

Non-patent References 1 and 2 describe a method in which a promoter sequence, target gene sequence, and polyadenylation signal are independently amplified by using primers which have been produced by adding a sequence homologous with the terminal region of the DNA fragment that is to be joined to the 5' end of the primers used in gene amplification. By conducting jPCR with these three DNA fragments, it is then possible to produce joined DNA fragments in which the promoter sequence, target gene sequence, and polyadenylation signal are functionally joined (see FIG. 2 in Non-patent Reference 1 and FIG. 1 in Non-patent Reference 2).

The target gene fragment is normally prepared as a PCR product. However, when the binding specificity of the primers to the template is low in PCR, when multiple sequences similar to the primer sequences are present in the template, and the like, nonspecific amplification reactions take place. As a result, regions that are sandwiched with primer sequences at either end will end up producing nonspecifically amplified DNA fragments that are not in the target gene being cloned.

In conventional jPCR, sequences for joining are added to the primers used to amplify the various DNA fragments. A sequence hybridizing with a different DNA fragment is introduced onto the terminus of each DNA fragment being amplified with a given primer. Next, the amplified DNA fragments are mixed and jPCR is conducted to form "joined DNA fragments" in which two or more DNA fragments are bound.

However, in this method, fragments consisting of regions sandwiched between primer sequences in the PCR product obtained by the gene amplification reaction with sequences not derived from the target gene also form "joined DNA fragments" in the same manner as target gene fragments.

Even assuming that just target gene fragments are amplified by the gene amplification reaction, the primers employed in gene amplification remain in the reaction solution. When jPCR is conducted without removing them, the amplification of various DNA fragments that are constituent elements of the "joined DNA fragments" takes place preferentially over the amplification of the "joined DNA fragments," and "joined DNA fragments" containing sequences derived from the desired target gene tend not to form.

Accordingly, in the methods described in the above-cited patent reference and non-patent references, the PCR amplification product must be purified to a degree where it is possible to ignore the effects of contamination by DNA fragments containing non-target gene sequences and primers following PCR amplification of the target gene fragments.

As set forth above, to produce a "joined DNA fragment" combining two or more double-stranded DNA fragments by the above method, the DNA fragments containing the target gene sequence that are contained in the PCR amplification product must be purified to a degree where the effects on the joining reaction of contamination by DNA fragments containing non-target gene sequences and the primers used in target gene amplification can be ignored in a step conducted prior to joining one or more DNA fragments having specific functions other that of the target gene. However, when the length of the target gene fragment is similar to the length of a non-target gene fragment, separation of the target gene fragment is difficult. Thus, in such cases, it becomes impossible to obtain just "joined DNA fragments" containing the sequence derived from the desired target gene.

Accordingly, the object of the present invention is to provide a method permitting the specific production of a "joined DNA fragment" containing a sequence derived from a desired target gene by causing one or more double-stranded DNA fragments to bind to a PCR amplification product containing a target gene sequence without purifying the PCR amplification product.

MEANS OF SOLVING THE PROBLEM

The present inventors conducted extensive research. As a result, they succeeded in specifically obtaining the desired joined DNA fragment, and devised the first aspect of the present invention (described in claim 1 of the present invention), by:

in the course of joining a double-stranded gene fragment containing a target gene sequence and a double-stranded joining DNA fragment containing a joining DNA region for binding with the double-stranded gene fragment, (1) preparing the double-stranded gene fragment in the form of a 3' end protruding double-stranded gene fragment containing a target gene in the middle portion thereof, having associative regions on the two termini thereof, the two associative regions having base sequences that do not mutually associate, at least a portion of the base sequence of one or both of the regions being an inherent sequence contained in the target gene, with a protruding terminus of one or more nucleotides being present on the 3' ends of both of the associative regions;

(2) preparing a double-stranded joining DNA fragment, containing at least one joining DNA region in the middle portion thereof, and having associative regions on the two termini thereof, as the double-stranded DNA fragment; wherein (3-1) one of the associative regions of the 3' end protruding double-stranded gene fragment is comprised of a base sequence that is homologous with the associative region of one terminus of the double-stranded joining DNA fragment, with the sequence on the terminus to which the 3' protruding end has been added being the side that binds to the joining DNA region in one of the associative regions of the double-stranded joining DNA fragment;

(3-2) the terminus protruding from the one associative region of the 3' end protruding double-stranded gene fragment does not have a strand-elongating function in a DNA synthesis reaction;

(3-3) the other associative region of the 3' end protruding double-stranded gene fragment is comprised of a base sequence that is homologous with the associative region of the other terminus of the double stranded joining DNA fragment, with the sequence on the terminus to which the 3' protruding end has been added being the side that binds to the joining DNA region in the other of the associative regions of the double-stranded joining DNA fragment;

(3-4) the terminus protruding from the other associative region of the 3' end protruding double-stranded gene fragment does not have a strand-elongating function in the DNA synthesis reaction;

(4) subjecting the 3' end protruding double-stranded gene fragment and double-stranded joining DNA fragment to at least two cycles of a thermal denaturation, re-association, and DNA synthesis reaction to inhibit the nonspecific production of joining DNA fragments in which joining DNA regions join to both sides of a non-target gene, and to cause joining DNA regions to join to both ends of the target gene, even in the presence of primers used to amplify the two-stranded gene fragment in PCR and a gene fragment containing a non-target gene in a double-stranded gene fragment.

Denoting one of the associative regions as "region 1" and the other associative region as "region 2," the 3' end protruding double-stranded gene fragment has a sequence schematically denoted by region 1-target gene-region 2. The double-stranded joining DNA fragment has a sequence schematically denoted by region 2-joining DNA region-region 1. The joined DNA fragment has at least one sequence schematically denoted by region 2-joining DNA region-region 1-target gene-region 2-joining DNA region-region 1.

Further, when the joining DNA region has the sequence schematically denoted by region 2-joining DNA region 2-joining DNA region 1-region 1 containing two joining DNA regions 1 and 2, at least one sequence schematically denoted by region 2-joining DNA region 2-joining DNA region 1-region 1-target gene-region 2-joining DNA region 2-joining DNA region 1-region 1 will be present.

By dividing the double-stranded joining DNA fragment of the first aspect of the present invention set forth above into two double-stranded joining DNA fragments 1 and 2 having the sequences schematically denoted by region 1-double-stranded joining DNA region 1 and joining DNA region 2-region 2, respectively, the present inventors successfully specifically obtained the desired joined DNA fragment in which joining region 1 was joined on one side of the target gene and joining DNA region 2 was joined on the other side thereof, while inhibiting the nonspecific generation of joined DNA fragments in which joining DNA region 1 was joined to one side and joining DNA region 2 was joined to the other side of a non-target gene. The second aspect of the present invention (the invention described in claim 9) was devised on that basis.

The joined DNA fragment obtained here has the sequence schematically denoted by joining DNA region 1-region 1-target gene-region 2-joining DNA region 2.

Additionally, in the second aspect of the present invention, by dividing in two and having one of the double-stranded joining DNA fragments employ the sequence schematically denoted by region 1-joining DNA region 1 or joining DNA region 2-region 2, the present inventors successfully specifically obtained the desired single-side joined DNA fragment in which joining DNA region 1 or 2 was joined to one side of the target gene while inhibiting the nonspecific generation of joined DNA fragments in which joining DNA region 1 or 2 was joined to one side of a non-target gene. The third aspect of the present invention (the invention described in claim 16) was devised on that basis.

The present invention further includes the 3' end protruding double-stranded gene fragment, double-stranded joining DNA fragment, and combinations thereof that are employed in the first through third aspects of the present invention, as well as kits comprising the same.

The present invention is as set forth below.

[1]

A method for producing a joined DNA fragment in which joining DNA regions have been joined on both ends of a target gene, comprising:

(1) preparing, from a double-stranded gene fragment comprising a target gene sequence, a 3' end protruding double-stranded gene fragment containing a target gene in the middle portion thereof, having associative regions on the two termini thereof, the two associative regions having base sequences that do not mutually associate, at least a portion of the base sequence of one or both of the regions being an inherent base sequence contained in the target gene, with a protruding terminus of one or more nucleotides being present on the 3' ends of both of the associative regions;

(2) preparing a double-stranded joining DNA fragment, containing a joining DNA region in the middle portion thereof, and having associative regions on the two termini thereof; wherein (3-1) one of the associative regions of the 3' end protruding double-stranded gene fragment is comprised of a base sequence that is homologous with the associative region of one terminus of the double-stranded joining DNA fragment, with the sequence on the terminus to which the 3' protruding end has been added being the side that connects to the joining DNA region in one of the associative regions of the double-stranded joining DNA fragment;

(3-2) the terminus protruding from the one associative region of the 3' end protruding double-stranded gene fragment does not have a strand-elongating function in a DNA synthesis reaction;

(3-3) the other associative region of the 3' end protruding double-stranded gene fragment is comprised of a base sequence that is homologous with the associative region of the other terminus of the double-stranded joining DNA fragment, with the sequence on the terminus to which the 3' protruding end has been added being the side that connects to the joining DNA region in the other of the associative regions of the double-stranded joining DNA fragment;

(3-4) the terminus protruding from the other associative region of the 3' end protruding double-stranded gene fragment does not have a strand-elongating function in the DNA synthesis reaction; and (4) subjecting the 3' end protruding double-stranded gene fragment and double-stranded joining DNA fragment to at least two cycles of a thermal denaturation, re-association, and DNA synthesis reaction to obtain a joined DNA fragment.

[2]

The production method according to [1], wherein, denoting one of the associative regions as "region 1" and the other associative region as "region 2," the joined DNA fragment comprises at least one sequence schematically denoted by region 2-joining DNA region-region 1-target gene region-region 2-joining DNA region-region 1.

[3]

The production method according to [1], wherein the joining DNA region is comprised of two joining DNA regions in the form of region A and region B; one of the associative regions of the 3' end protruding double-stranded gene fragment, from the terminus side, comprises sequences P1 and T1; the other, from the terminus side, is comprised of sequences P2 and T2; at least one sequence T1 or sequence T2 comprises an inherent base sequence that is contained in a target gene sequence; one of the associative regions of the double-stranded joining DNA fragment comprises, from the terminus side, sequences VP1 and VT1; the other, from the terminus side, comprises sequences VP2 and VT2; sequences VP1 and VT1 comprise base sequences that are homologous with sequences P1 and T1, respectively; and sequences VP2 and VT2 have base sequences that are homologous with sequences P2 and T2, respectively.

[4]

The production method according to [3], wherein the 3' end protruding double-stranded gene fragment is denoted by P1-T1-target gene-T2-P2; the double-stranded joining DNA fragment is denoted by VT2-VP2-sequence B-sequence A-VP1-VT1; the joined DNA fragment is a DNA fragment comprising at least one unit of VT2-VP2(T2-P2)-sequence B-sequence A-VP1-VT1(P1-T1)-target gene-VT2-VP2(T2-P2)-sequence B-sequence A-VP1-VT1(P1-T1); where VT2-VP2(T2-P2) means VT2-VP2 that is homologous with T2-P2; and where VP1-VT1(P1-T1) means VT1-VP1 that is homologous with T1-P1.

[5]

The production method according to [3] or [4], wherein the sequence without a strand-elongating function in the reaction synthesizing the DNA with a protruding end on the 3' end of sequence P2 is a sequence that is not homologous with the sequence adjacent to VP2 of sequence B, and the sequence without a strand-elongating function in the reaction synthesizing the DNA with a protruding end on the 3' end of sequence P1 is a sequence that is not homologous with the sequence adjacent to VP1 of sequence A.

The production method according to any one of [1] to [4], wherein the protruding ends are sequences containing a dideoxynucleotide(s) on the 3' ends thereof.

[7]

A method for producing a DNA fragment comprising at least a portion of at least one joining DNA region and the entire sequence of a target gene, comprising:

conducting PCR, with a joined DNA fragment produced by the method according to any one of [1] to [6] as template, using a forward primer and a reverse primer functioning in different joining DNA regions contained in a joined DNA fragment to amplify at least a portion of at least one joining DNA region and the entire sequence of a target gene contained in the joined DNA fragment.

[8]

A method for producing a DNA fragment, comprising conducting PCR employing a forward primer contained on the 3' end a portion of the base sequence of sequence A toward a target gene and employing a reverse primer contained on the 3' end a portion of the base sequence of sequence B toward the target gene with the joined DNA fragment produced by the method according to [3] as template to obtain a DNA fragment in which sequence A, the sequence of the target gene, and sequence B are joined.

[9]

A method for producing a joined DNA fragment in which a joining DNA region 1 has been joined on one side of a target gene and a joining DNA region 2 has been joined on the other side thereof, comprising:
(1) preparing, from a double-stranded gene fragment comprising a target gene sequence, a 3' end protruding double-stranded gene fragment containing a target gene in the middle portion thereof, having associative regions on the two termini thereof, the two associative regions having base sequences that do not mutually associate, at least a portion of the base sequence of one or both of the regions being an inherent base sequence contained in the target gene, with a protruding terminus of one or more nucleotides being present on the 3' ends of both of the associative regions;
(2) preparing a double-stranded joining DNA fragment 1 that comprises a joining DNA region 1 and a terminal associative region and a double-stranded joining DNA fragment 2 that comprises a joining DNA region 2 and a terminal associative region; wherein
(3-1) one of the associative regions of the 3' end protruding double-stranded gene fragments is comprised of a base sequence that is homologous with the associative region of the double-stranded joining DNA fragment 1, but with the sequence on the side of the terminus on which the 3' protruding end is added being the side that connects with the joining DNA region in the associative region of double-stranded joining DNA fragment 1;
(3-2) the terminus protruding from one of the associative regions of the 3' end protruding double-stranded gene fragment does not have a strand-elongating function in a DNA synthesis reaction;
(3-3) the other associative region of the 3' end protruding double-stranded gene fragment is comprised of a base sequence that is homologous with the associative region of the terminus of double-stranded joining DNA fragment 2, with the sequence of the terminus to which the 3' protruding end has been added being the side that connects to the joining DNA region in the associative region of the double-stranded joining DNA fragment 2;
(3-4) the terminus protruding from the other associative region of the 3' end protruding double-stranded gene fragment does not have a strand-elongating function in the DNA synthesis reaction; and
(4) subjecting the 3' end protruding double-stranded gene fragment and double-stranded joining DNA fragments 1 and 2 to at least two cycles of a thermal denaturation, re-association, and DNA synthesis reaction to obtain a joined DNA fragment.

[10]

The production method according to [9], wherein joining DNA region 1 contains sequence A and joining DNA region 2 contains sequence B, one of the associative regions of the 3' protruding double-stranded gene fragment comprises, from the terminus side, sequences P1 and T1, and the other comprises, from the terminus side, sequences P2 and T2, where at least one of sequence T1 and sequence T2 comprises an inherent base sequence containing the target gene sequence, the associative region of double-stranded joining DNA fragment 1 comprises, from the terminus side, sequences VT1 and VP1, the associative region of double-stranded joining DNA fragment 2 comprises, from the terminus side, sequences VT2 and VP2, sequences VP1 and VT1 comprise base sequences that are homologous with sequences P1 and T1, respectively, and sequences VP2 and VT2 comprise base sequences that are homologous with sequences P2 and T2, respectively.

[11]

The production method according to [10], wherein the 3' end protruding double-stranded gene fragment is denoted by P1-T1-target gene-T2-P2, double-stranded joining DNA fragment 1 is denoted by the sequence A-VP1-VT1, double-stranded joining DNA fragment 2 is denoted by VT2-VP2-sequence B, the joined DNA fragment comprises at least one unit of sequence A-VP1-VT1(P1-T1)-target gene-VT2-VP2 (T2-P2)-sequence B, where VT2-VP2(T2-P2) means VT2-VP2 that is homologous with T2-P2 and VP1-VT1(P1-T1) means VT1-VP1 that is homologous with T1-P1.

[12]

The production method according to [10] or [11], wherein the sequence without a strand-elongating function in the reaction synthesizing the DNA with a protruding end on the 3' end of sequence P2 is a sequence that is not homologous with the sequence adjacent to VP2 of sequence B, and the sequence without a strand-elongating function in the reaction synthesizing the DNA with a protruding end on the 3' end of sequence P1 is a sequence that is not homologous with the sequence adjacent to VP1 of sequence A.

[13]

The production method according to any one of [9] to [11], wherein the protruding ends are sequences containing a dideoxynucleotide(s) on the 3' ends thereof.

[14]

A method for producing a DNA fragment comprising at least a portion of at least one joining DNA region and the entire sequence of a target gene, comprising:
conducting PCR, with the joined DNA prepared by the method according to any one of [9] to [13] as template, using a forward primer and a reverse primer functioning in different joining DNA regions contained in a joined DNA fragment to amplify at least a portion of at least one joining DNA region and the entire sequence of a target gene contained in the joined DNA fragment.

[15]

A method for producing a DNA fragment, comprising conducting PCR employing a forward primer contained on the 3' end a portion of the base sequence of sequence A toward a target gene and employing a reverse primer contained on the 3' end a portion of the base sequence of sequence B toward the target gene using the joined DNA fragment produced by the method according to [10] as template to obtain a DNA fragment in which sequence A, the sequence of the target gene, and sequence B are joined.

[16]

A method for producing a single-side joined DNA fragment in which a joining DNA region has been joined on one side of a target gene, comprising:
(1) preparing, from a double-stranded gene fragment comprising a target gene sequence, a 3' end protruding double-stranded gene fragment comprising an associative region on the side of one terminus of the target gene sequence, with at least a portion of the base sequence of this region being an inherent base sequence contained in the target gene sequence, and there being a protruding terminus of one or more nucleotides on the 3' end of the associative region;

(2) preparing a double-stranded joining DNA fragment comprising a joining DNA region and having a terminal associative region; wherein (3-1) one of the associative regions of the 3' end protruding double-stranded gene fragments is comprised of a base sequence that is homologous with the associative region of the double-stranded joining DNA fragment, but with the sequence on the side of the terminus on which the 3' protruding end is added being the side that connects with the joining DNA region in the associative region of the double-stranded joining DNA fragment;

(3-2) the terminus protruding from one of the associative regions of the 3' end protruding double-stranded gene fragment does not have a strand-elongating function in a DNA synthesis reaction; and (4) subjecting the 3' end protruding double-stranded gene fragment and double-stranded joining DNA fragment to one cycle of a thermal denaturation, re-association, and DNA synthesis reaction to obtain a hetero double-stranded DNA product, and then employing the hetero double-stranded DNA product as template to conduct a polymerase chain reaction and obtain a single-sided joined DNA fragment.

[17]

The production method according to [16], wherein the joining DNA region comprises sequence A; the associative region of the 3' end protruding double-stranded gene fragment comprises, from the terminus side, sequences P1 and T1; at least one of sequence T1 and sequence T2 comprises an inherent base sequence contained in the target gene sequence; the associative region of the double-stranded joining DNA fragment comprises, from the terminal side, sequences VT1 and VP1; sequences VP1 and VT1 have base sequences that are homologous with sequences P1 and T1, respectively; and a primer contained on the 3' end so as to cause a portion of the target gene of the hetero double-stranded DNA product to orient toward the protruding terminus side of the target gene and a primer contained on the 3' end so as to cause a portion of sequence A of the hetero double-stranded DNA product to orient toward the target gene side are employed in the polymerase chain reaction utilizing the hetero two-stranded DNA product as template.

[18]

The production method according to [17], wherein the 3' end protruding double-stranded gene fragment is denoted by P1-T1-target gene; the double-stranded joining DNA fragment is denoted by sequence A-VP1-VT1; the single-side joined DNA fragment is a DNA fragment comprising at least one sequence A-VP1-VT1(P1-T1)-target gene; and VP1-VT1(P1-T1) means VT1-VP1 that is homologous with T1-P1.

[19]

The production method according to [17] or [18], wherein the sequence not having a strand-elongating function in the DNA synthesis reaction of the protruding end on the 3' end of sequence P1 is a sequence that is not homologous when adjacent to VP1 of sequence A.

[20]

The production method according to any one of [16] to [18], wherein the protruding terminus is a sequence containing a dideoxynucleotide on the 3' end thereof.

[21]

The production method according to any one of [3], [4], [10], or [11], further comprising causing deoxynucleotide terminal transferase to act upon the polydeoxynucleotide and double-stranded DNA fragment containing the sequence of the target gene to obtain a 3' end protruding double-stranded gene fragment comprising the sequence of the target gene (wherein the double-stranded DNA fragment containing the target gene sequence comprises sequence P1 and sequence P2 on the ends thereof, sequence T1 is present within a portion of sequence P1, sequence T2 is present within a portion of sequence P2, and one or both of sequences T1 and T2 comprise a base sequence that is inherent to the target gene).

[22]

The production method according to [17] or [18], further comprising causing deoxynucleotide terminal transferase to act upon the polydeoxynucleotide and double-stranded DNA fragment containing the sequence of the target gene to obtain a 3' end protruding double-stranded gene fragment comprising the sequence of the target gene (wherein sequence P1 is present on one terminus of the double-stranded DNA fragment containing the target gene sequence and sequence T1 is present within a portion of sequence P1, and sequence T1 comprises a base sequence that is inherent to the target gene).

[23]

The production method according to [3], [4], [10], or [11], wherein one or both of sequence T1 and sequence T2 comprise a base sequence that is inherent to the target gene.

[24]

The production method according to [3], [4], [10], or [11], wherein one or both of sequence P1 and sequence P2 comprise a base sequence that is inherent to the target gene.

[25]

The production method according to [3], [4], [10], [11], [17], or [18], wherein each of sequences P1 and P2 is comprised of 10 or more bases.

[26]

The production method of any one of [1] to [25], wherein the target gene is an antibody gene or a T cell receptor gene, the 3' end protruding double-stranded gene fragment contains a sequence derived from an antibody gene or T cell receptor gene, and region VP1 and region VT1 in the double-stranded joining DNA fragment comprising sequence A or the double-stranded joining DNA comprise sequences that are, or are not, derived from an antibody gene or a T cell receptor gene.

[27]

The production method according to [26], wherein the target gene is an antibody gene or a T cell receptor gene, the 3' end protruding double-stranded gene fragment contains a sequence that is derived from the antibody gene or T cell receptor gene, and region VP2 and region VT2 in the double-stranded joining DNA fragment having sequence B or the double-stranded joining DNA fragment are sequences that are, or are not, derived from antibody genes or T cell receptor genes.

[28]

A method for producing an antibody or T cell receptor employing joined DNA prepared by the method according to [26] or [27].

[29]

A 3' end protruding double-stranded gene fragment from a double-stranded gene fragment containing a target gene sequence, comprising a target gene sequence in the middle portion thereof, comprising associative regions on the two termini thereof, the two associative regions comprising mutually non-associative base sequences, at least a portion of the base sequence of one or both of the regions being an inherent base sequence contained in the target gene sequence, and both of the associative regions having protruding termini of one or more nucleotides on the 3' ends thereof.

[30]
A double-stranded joining DNA fragment comprising a joining DNA region in the middle portion thereof and comprising associative regions on the two termini sides thereof.

[31]
An assembly, employed in a method of preparing a joined DNA fragment in which joining DNA regions are joined to both sides of a target gene, comprising:
(1) a 3' end protruding double-stranded gene fragment from a double-stranded gene fragment containing a target gene sequence, comprising a target gene sequence in the middle portion thereof, comprising associative regions on the two termini thereof, the two associative regions comprising mutually non-associative base sequences, at least a portion of the base sequence of one or both of the regions being an inherent base sequence contained in the target gene sequence, and both of the associative regions having protruding termini of one or more nucleotides on the 3' ends thereof; and
(2) double-stranded joining DNA fragments comprising a joining DNA region in the middle portion thereof, and having associative regions on the two terminus sides thereof, respectgively.

[32]
The assembly according to [31], wherein:
(3-1) one of the associative regions of the 3' end protruding double-stranded gene fragment is comprised of a base sequence that is homologous with the associative region of one terminus of the double-stranded joining DNA fragment, with the sequence on the terminus to which the 3' protruding end has been added being the side that connects to the joining DNA region in one of the associative regions of the double-stranded joining DNA fragment;
(3-2) the terminus protruding from the one associative region of the 3' end protruding double-stranded gene fragment does not have a strand-elongating function in a DNA synthesis reaction;
(3-3) the other associative region of the 3' end protruding double-stranded gene fragment is comprised of a base sequence that is homologous with the associative region of the other terminus of the double stranded joining DNA fragment, with the sequence on the terminus to which the 3' protruding end has been added being the side that connects to the joining DNA region in the other of the associative regions of the double-stranded joining DNA fragment; and
(3-4) the terminus protruding from the other associative region of the 3' end protruding double-stranded gene fragment does not have a strand-elongating function in the DNA synthesis reaction.

[33]
A double-stranded joining DNA fragment 1 comprising a joining DNA region 1 and having an associative region on the terminus, or a double-stranded joining DNA fragment 2 comprising a joining region 2 and having an associative region on the terminus.

[34]
An assembly, employed in a method of preparing a joined DNA fragment in which a joining DNA region 1 has been joined to one side of a target gene and a joining DNA region 2 has been joined to the other side thereof, comprising:
(1) a 3' end protruding double-stranded gene fragment containing a target gene in the middle portion thereof, having associative regions on the two termini thereof, the two associative regions having base sequences that do not mutually associate, at least a portion of the base sequence of one or both of the regions being an inherent base sequence contained in the target gene, with protruding termini of one or more nucleotides being present on the 3' ends of both of the associative regions, that is derived from a double-stranded gene fragment comprising a target gene sequence; and
(2) a double-stranded joining DNA fragment 1, comprising a terminal associative region and containing a joining DNA region 1 and a double-stranded joining DNA fragment 2, comprising a terminal associative region and containing a joining DNA region 2.

[35] The assembly according to (3-4), wherein:
(3-1) one of the associative regions of the 3' end protruding double-stranded gene fragments is comprised of a base sequence that is homologous with the associative region of double-stranded joining DNA fragment 1, but with the sequence on the side of the terminus on which the 3' protruding end is added being the side that connects with the joining DNA region in the associative region of double-stranded joining DNA fragment 1;
(3-2) the terminus protruding from one of the associative regions of the 3' end protruding double-stranded gene fragment does not have a strand-elongating function in a DNA synthesis reaction;
(3-3) the other associative region of the 3' end protruding double-stranded gene fragment is comprised of a base sequence that is homologous with the associative region of the terminus of double-stranded joining DNA fragment 2, with the sequence of the terminus to which the 3' protruding end has been added being the side that connects to the joining DNA region in the associative region of the double-stranded joining DNA fragment; and
(3-4) the terminus protruding from the other associative region of the 3' end protruding double-stranded gene fragment does not have a strand-elongating function in the DNA synthesis reaction.

[36]
A 3' end protruding double-stranded gene fragment derived from a double-stranded gene fragment, comprising a target gene sequence, and comprising an associative region on the side of one terminus of the target gene sequence, with at least a portion of the base sequence of this region being an inherent base sequence contained in the target gene sequence, and with a protruding terminus of one or more nucleotides being present on the 3' end of the associative region.

[37]
A double-stranded joining DNA fragment comprising a joining DNA region and having an associative region on the terminus side thereof.

[38]
An assembly employed in a method of preparing a single-side joined DNA fragment in which a joining DNA region has been joined on one side of a target gene, comprising:
(1) a 3' end protruding double-stranded gene fragment, derived from a double-stranded gene fragment comprising a target gene sequence, comprising an associative region on the side of one terminus of the target gene sequence, with at least a portion of the base sequence of this region being an inherent base sequence contained in the target gene sequence, and with a protruding terminus of one or more nucleotides being present on the 3' end of the associative region, and
(2) a double-stranded joining DNA fragment comprising a joining DNA region and having a terminal associative region.

[39]

The assembly according to [38], wherein:

(3-1) one of the associative regions of the 3' end protruding double-stranded gene fragments is comprised of a base sequence that is homologous with the associative region of the double-stranded joining DNA fragment, but with the sequence on the side of the terminus on which the 3' protruding end is added being the side that connects with the joining DNA region in the associative region of the double-stranded joining DNA fragment; and (3-2) the terminus protruding from one of the associative regions of the 3' end protruding double-stranded gene fragment does not have a strand-elongating function in a DNA synthesis reaction.

[40]

The double-stranded joining DNA fragment or assembly of any one of [30] to [35] or [37] to [39], wherein the joining DNA region is at least one sequence selected from the group consisting of introns, exons, fluorescent protein genes, and tag sequences such as His tags, promoter sequences, enhancer sequences, and polyadenylation signal that are capable of controlling the expression of various genes within bacterial and animal cells.

[41]

A kit employed in a method of preparing a joined DNA fragment in which joining DNA regions have been joined to both sides of a target gene, comprising the 3' end protruding double-stranded gene fragment according to [29], the double-stranded joining DNA fragment according to [30], or the assembly according to [31] or [32].

[42]

A kit employed in a method of preparing a joined DNA fragment in which a joining DNA region 1 has been joined to one side of a target gene and a joining DNA region 2 has been joined to the other side thereof, comprising the 3' end protruding double-stranded gene fragment according to [29], the double-stranded joining DNA fragment according to [33], or the assembly according to [34] or [35].

[43]

A kit employed in a method of preparing a single-sided joined DNA fragment in which a joining DNA region has been joined to one side of a target gene, comprising the 3' end protruding double-stranded gene fragment according to [36], the double-stranded joining DNA fragment according to [37], or the assembly according to [38] or [39].

[44]

The kit according to any one of [41] to [43], wherein the joining DNA region is at least one sequence selected from the group consisting of introns, exons, fluorescent protein genes, and tag sequences such as His tags, promoter sequences, enhancer sequences, and polyadenylation signal that are capable of controlling the expression of various genes within bacterial and animal cells.

EFFECT OF THE INVENTION

The method of the present invention makes it possible to specifically join target gene amplification products to joining DNA fragments in the presence of gene amplification products obtained by nonspecific amplification. The method of the present invention permits the specific preparation of joined DNA fragments in which, for example, a sequence A and a sequence B contained in a joining DNA fragment are functionally joined in the order of sequence A-target gene sequence-sequence B, regardless of whether the DNA fragment containing the target gene sequence has been purified.

Further, the present invention permits the expression of a target gene sequence by employing a promoter sequence as sequence A and a polyadenylation signal as sequence (B) and introducing a joined DNA fragment in which these have been functionally joined in the order of sequence A-target gene sequence-sequence B into a host cell. As will be described in detail further below, when the unit of double-stranded DNA having a sequence in which these sequences have been functionally joined in this order is comprised of a double-stranded DNA fragment with the minimum structure required for expression of the target gene sequence, such as a sequence in which a promoter sequence and a polyadenylation signal have been functionally joined, it will sometimes be referred to as an expression unit in the present invention.

Since this expression unit, in contrast to circular vectors prepared using *E. coli*, is a linear double-stranded DNA fragment synthesized in vitro, no harmful substances derived from bacteria, such as endotoxins, gets mixed. As a result, a host cell is used in a state unaffected by harmful substances, making it possible to specifically produce the protein coding for the target gene in large quantities.

BRIEF DESCRIPTION OF DRAWINGS

FIG. 9 is a drawing confirming, by agarose gel electrophoresis, amplified DNA obtained by subjecting a polymer of human γ-chain gene expression units, produced by joining 3' end polynucleotide added target gene fragments 1 with human γ-chain gene double-stranded joining DNA fragments, to PCR using mismatch primer or normal primer. Lane 1: amplification of human γ-chain gene expression unit using primers E and F. Lane 2: amplification of human γ-chain gene expression unit using primers G and H.

FIG. 10 is a descriptive drawing of the base sequence of target gene fragment 1.

FIG. 11 is a descriptive drawing of the base sequence of non-target gene fragment 2.

FIG. 12 is a descriptive drawing of the base sequence of a human γ-chain gene double-stranded joining DNA fragment.

MODES OF CARRYING OUT THE INVENTION

[Definition of Terms]

Figure 1:
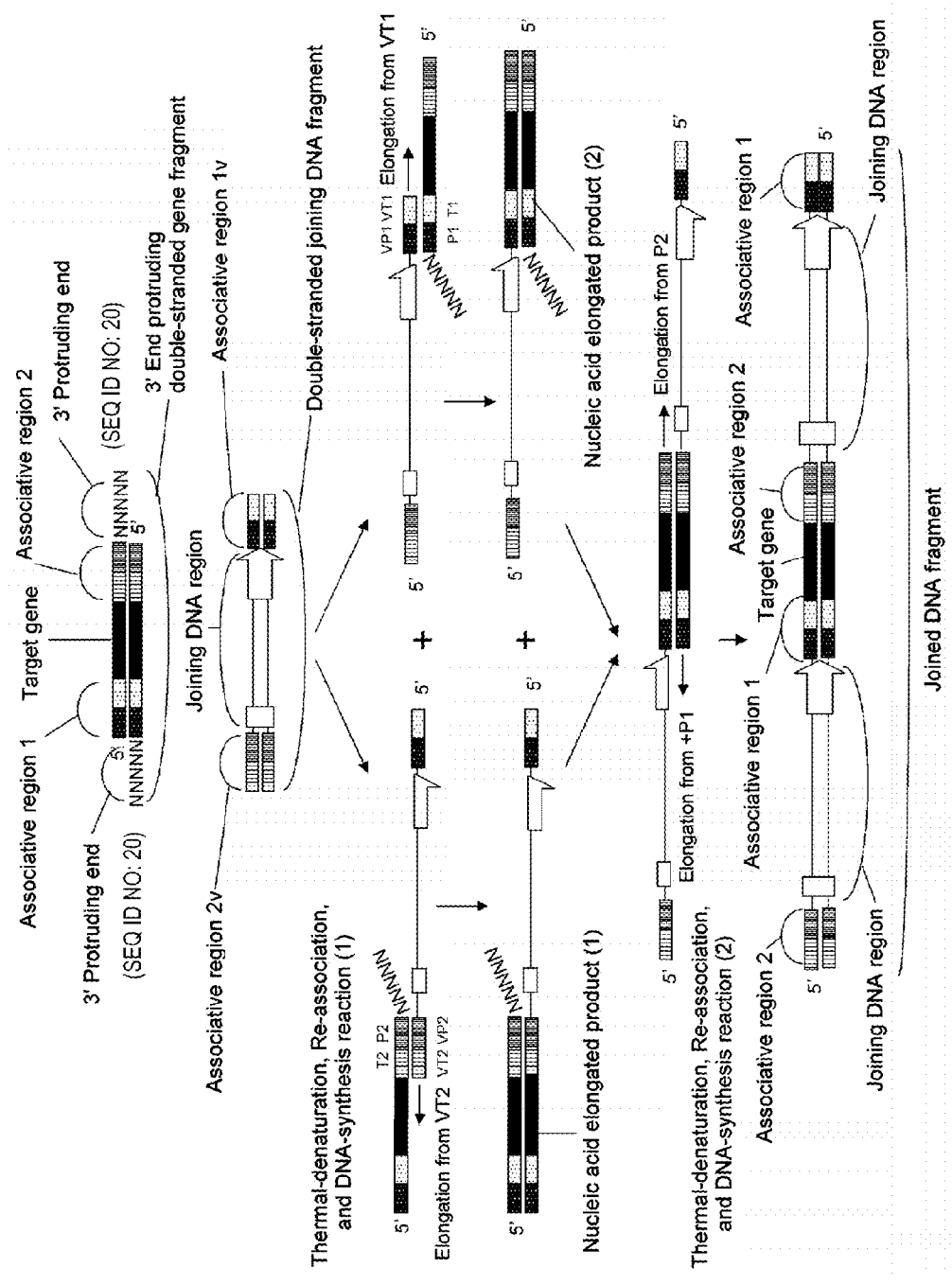
FIG. 1 is a reaction scheme describing the first aspect of the present invention.

In the present specification, the following terms have the meanings indicated below.

A "target gene sequence" is the sequence of a gene, within a joined DNA fragment in which double-stranded joining DNA fragments have been joined, that is to be specifically obtained in the method of the present invention. Examples of target gene sequences are given further below.

A "double-stranded gene fragment" is a double-stranded gene fragment comprising a target gene sequence.

A "3' end protruding double-stranded gene fragment" is a gene fragment having protruding termini at both of the 3' ends of a double-stranded gene fragment.

A "double-stranded joining DNA fragment" is a DNA fragment that is joined to a target gene sequence in order to obtain a joined DNA fragment in the method of the present invention.

An "associative region" means a region that is capable of associating with one of the two "associative regions" present in the double-stranded joining DNA fragment in the re-association (annealing) in the "thermal-denaturation, re-association, and DNA-synthesis reaction" set forth further below.

An "inherent base sequence contained in the target gene sequence" means a base sequence that is contained in the target gene sequence and is originally present in the target gene.

A "joined DNA fragment" means a double-stranded joined DNA fragment in which joining DNA regions have been joined to both ends of a target gene.

A "single-side joined DNA fragment" means a double-stranded joined DNA fragment in which a joining DNA region has been joined to one end of the target gene.

A "joined unit" means "sequence A-target gene-sequence B".

A "joined unit polymer" means a DNA fragment in which a plurality of joined units have been linked.

A "sense strand" means either one of the single strands of DNA in double-stranded DNA, and the term "antisense strand" means the other single strand of DNA in the double-stranded DNA when one of the single strands of DNA is the "sense strand".

A "region" means a portion comprised of the sequence of the sense strand and the sequence of the antisense strand corresponding to a specific site.

Terms other than the above that are defined in the specification below are employed as defined.

[First Aspect of the Present Invention]

The first aspect of the present invention is described in detail below.

The first aspect of the present invention is a method for producing a "joined DNA fragment", in which joining DNA regions have been joined to both sides of a target gene, from a "3' end protruding double-stranded gene fragment" and a "double-stranded joining DNA fragment".

The "3' End Protruding Double-stranded Gene Fragment"

In the first aspect of the present invention, (1) a "3' end protruding double-stranded gene fragment" is prepared from a double-stranded gene fragment comprising a target gene sequence. As shown in the top portion of FIG. 1, the "3' end protruding double-stranded gene fragment" comprises a target gene sequence in the middle portion thereof, having associative regions (associative region 1 and associative region 2) on the two termini thereof.

The "target gene sequence" is not specifically limited in the present invention. The "target gene sequence" can be, for example, the sequence of an antibody gene, with the sequence positioned on one terminus of the antibody gene sequence being a sequence derived from a constant region of the antibody gene. In addition to antibody gene sequences, the "target gene sequence" can be a T cell receptor gene, splicing variant, or the like, in the form of a DNA sequence consisting of a primer region and an area adjacent to it with an inner sequence that is stable but which has variable internal sites.

An "associative region" is a region that can associate with one of the two "associative regions" present on a double-strand joining DNA fragment during re-association (annealing) in the "thermal denaturation, re-association, and DNA synthesis reaction" described further below. The association relation of the "associative region" of the 3' end protruding double-stranded gene fragment and the "associative region" of the double-stranded joining DNA fragment will be described further below.

The two associative regions on the termini of the "3' end protruding double-stranded gene fragment" have base sequences that do not mutually associate. The term "base sequences that do not mutually associate" means base sequences in which neither the sense strand nor antisense strand of the "associative region" of one will associate with either the sense strand or antisense strand of the "associative region" of the other.

Further, either one or both of the "associative regions" of the 3' end protruding double-stranded gene fragment are inherent base sequences at least one portion of the base sequence of each is contained in the target gene sequence. The term "inherent base sequence contained in the target gene sequence" is a base sequence, originally present in the target gene, that is contained in the target gene sequence. The inherent base sequence contained in the target gene sequence that is contained in the "associative regions" is a sequence in which the base sequence that is contained in the double-stranded gene fragment containing the target gene sequence is retained intact in the course of preparing the "3' end protruding double-stranded gene fragment" from the double-stranded gene fragment containing the target gene sequence. Target gene sequences, in addition to the above base sequences of the "associative regions," are also retained in the "3' end protruding double-stranded gene fragment." In other words, the base sequence of the "associative regions" can be said to be part of the target gene sequence. When causing the target gene sequence that is the ultimate goal to express the protein that is coded for by the target gene sequence in the "joined DNA fragment" produced by the method of the first aspect of the present invention through additional steps (which will be described further below), there are cases where portions coded for by the "inherent base sequence contained in the target gene sequence" becomes part of the protein that is expressed.

The 3' end protruding double-stranded gene fragment has protruding termini comprising one or more nucleotides on the 3' ends of the two associative regions. These protruding termini are comprised of single-stranded nucleotides, one terminus of which joins to the 3' end of the "associative region" and the other terminus of which, that is, the 3' end, is in an unconnected, free state.

The relation of (3-2) or (3-4) below exists for protruding ends between the associative regions present in the double-stranded joining DNA fragment.

(3-2) The terminus protruding from one of the associative regions of the 3' end protruding double-stranded gene fragment does not have a chain-elongating function in the DNA synthesis reaction.

(3-4) The terminus protruding from the other associative region of the 3' end protruding double-stranded gene fragment does not have a chain-elongating function in the DNA synthesis reaction.

In the present invention, a sequence "that does not have a chain-elongating function in the DNA synthesis reaction" means a sequence that does not hybridize with the opposing single strand, and as a result, strand elongation does not occur in a DNA synthesis reaction employing the opposing single strand as template. For example, when both are DNA, a sequence in which at least one nucleotide of the opposing single strand is not complementary is a sequence that "does not have a chain-elongating function in a DNA synthesis reaction." However, the hybridizing conditions are the re-association conditions in the first cycle of thermal denaturation, re-association, and DNA synthesis reaction. The conditions of the first cycle of re-association will be described further below. A nucleotide sequence having a structure such that the next nucleotide cannot be added to the 3' end thereof in a DNA synthesis reaction, such as dideoxynucleotide, is a sequence "not having a chain-elongating function in a DNA synthesis reaction."

Since associative regions that are present on the protruding termini and on double-stranded joining DNA fragments satisfy the relations of (3-2) and (3-4) above, even in cases where non-target 3' end protruding double-stranded gene fragments containing non-target genes in the region corresponding to the target gene and where the primers used to amplify by PCR the double-stranded gene fragment that is the source of the 3' end protruding double-stranded gene fragment are also present around the 3' end protruding double-stranded gene fragment prepared by PCR, in the two cycles of thermal denaturation, re-association, and DNA synthesis reaction that are conducted, it is possible to inhibit the production of non-target joined DNA fragments in which joining DNA regions are joined to both sides of a non-target gene when using a non-target 3' end protruding double-stranded gene fragment as template. As a result, it is possible to inhibit the nonspecific production of non-target joined DNA in which joining DNA regions are joined to both sides of a non-target gene. A more specific description will be given below.

The "Double-stranded Joining DNA Fragments"

(2) In the present invention, double-stranded joining DNA fragments are prepared that have associative regions on both terminus sides and contain joining DNA regions in the center portions thereof. As indicated in the second item from the top in FIG. 1, the double-stranded joining DNA fragments have associative regions (associative region 1 and associative region 2) on both terminus sides of the joining DNA region.

Joining DNA regions are not specifically limited other than that they be DNA regions that are capable of imparting additional functions to the joined DNA fragment through being joined on both sides of the target gene. Examples of the joining DNA regions are introns, exons, fluorescent protein genes, and tag sequences such as His tags and promoter sequences, enhancer sequences, and polyadenylation signal that are capable of controlling the expression of various genes within bacterial and animal cells.

As set forth above, when one of the associative regions is denoted as "region 1" and the other associative region is denoted as "region 2", the 3' end protruding double-stranded gene fragment has a sequence that is schematically denoted as region 2-target gene-region 1, the double-stranded joining DNA fragment has a sequence that is schematically denoted as region 2-joining DNA region-region 1, and the joined DNA fragment has at least one sequence schematically denoted as region 2-joining DNA region-region 1-target gene-region 2-joining DNA region-region 1. Accordingly, for example, when the joining DNA region is a fluorescent protein gene, the joined DNA fragment will contain at least one sequence denoted by region 2-fluorescent protein gene-region 1-target gene-region 2-fluorescent protein gene-region 1.

When causing the target gene to be expressed in a host cell to produce a protein coding for the target gene, double-stranded joining DNA fragments containing two joining DNA regions 1 and 2 in the form of a polyadenylation signal and a promoter are employed as joining DNA regions. In that case, the double-stranded joining DNA fragments have a structure that is schematically denoted as region 2-polyadenylation signal-promoter-region 1. When this double-stranded joining DNA fragment is employed, the joined DNA fragment will contain at least one sequence schematically denoted by region 2-polyadenylation signal-promoter-region 1-target gene-region 2-polyadenylation signal,-promoter-region 1.

The relation between the associative regions of the 3' end protruding double-stranded gene fragment and the associative regions of the double-stranded joining DNA fragment will be described next.

In the present description, the term "associative region" in a double-stranded gene fragment and a double-stranded joining DNA fragment means a region that permits a DNA (gene) fragment that has been separated into single strands to hybridize with a single-stranded gene (DNA) fragment having a complementary base sequence to form a double-strand in the re-association of the "denaturation, re-association, and DNA synthesis reaction" described further below and in the thermal denaturation preceding re-association. However, whether or not association is possible depends on both the length of the two single strands of DNA (gene) fragments of mutually complementary base sequences and on their base sequences. Thus, an "associative region" means a region that is capable of associating under re-association conditions where the length of the single-stranded associative region is 11 nucleotides or greater and the annealing temperature during re-association is 0 to 20° C. lower than the calculated Tm value.

In the first aspect of the present invention, the associative region of the 3' end protruding double-stranded gene fragment and the associative region of the double-stranded joining DNA fragment satisfy the relations stated in (3-1) and (3-3) below.

(3-1) One of the associative regions of the 3' end protruding double-stranded gene fragment (associative region 1 in FIG. 1) is comprised of a base sequence that is homologous with the associative region of one of the termini of the double-stranded joining DNA fragment (associative region 1v in FIG. 1). However, the terminus side that connects with the 3' protruding terminus is the side that connects with the joining DNA region in the associative region of the double-stranded joining DNA fragment. That is, one of the associative regions (associative region 1) of the 3' end protruding double-stranded gene fragment and one of the terminal associative regions (associative region 1v) of the double-stranded joining DNA fragment are comprised of homologous base sequences. However, the terminus side of one of the associative regions of the 3' end protruding double-stranded gene fragment is positioned on the side (the inside) that connects with the joining DNA region in one of the terminal associative regions of the double-stranded joining DNA fragment.

(3-3) The other associative region of the 3' end protruding double-stranded gene fragment (associative region 2 in FIG. 1) is comprised of a base sequence that is homologous with the associative region of the other terminus of the double-stranded joining DNA fragment (associative region 2v in FIG. 1). However, the sequence of the terminus on the side on which the 3' protruding end is added is the side that connects with the joining DNA region in one of the associative regions of the double-stranded joining DNA fragment. Similar to (3-1) above, the other associative region (associative region 2) of the 3' end protruding double-stranded gene fragment and the other terminal associative region (associative region 2v) of the double-stranded joining DNA fragment are comprised of homologous base sequences. However, the terminus side of the other associative region of the 3' end protruding double-stranded gene fragment is positioned on the side (the inside) that connects with the joining DNA region in the other terminal associative region of the double-stranded joining DNA fragment.

In the first aspect of the present invention, since the associative region of the 3' end protruding double-stranded gene fragment and the associative region of the double-stranded joining DNA fragment satisfy the relations indicated in (3-1) and (3-3), the two cycles of thermal denaturation, re-association, and DNA synthesis reaction that are conducted cause the two ends of the target gene to become sandwiched between region 2-joining DNA region-region 1, yielding a joined DNA fragment having at least one sequence schematically denoted by region 2-joining DNA region-region 1-target gene-region 2-joining DNA region-region 1. A more specific description is given in specific examples further below.

"Denaturation, Re-association, and the DNA Synthesis Reaction"

The first aspect of the present invention includes (4) using the above 3' end protruding double-stranded gene fragment and double-stranded joining DNA fragment to conduct two cycles of denaturation, re-association, and a DNA synthesis reaction to obtain the above joined DNA fragment. FIG. 1 shows an example of conducting two cycles of denaturation, re-association, and a DNA synthesis reaction. The detailed conditions of the denaturation, re-association, and DNA synthesis reaction are given further below. As shown in the lowermost section of FIG. 1, the joined DNA fragment that is produced by this method, when one of the associative regions (associative region 1) is denoted as "region 1" and the other associative region (associative region 2) is denoted as "region 2", is a DNA fragment having at least one sequence schematically denoted by region 2-joining DNA region-region 1-target gene-region 2-joining DNA region-region 1.

"Embodiment of carrying out the first aspect"

The embodiment of carrying out the first aspect of the present invention will be described in greater detail with reference to FIG. 2. In the implementation embodiment shown in FIG. 2:

(i) One of the associative regions 1 of the 3' end protruding double-stranded gene fragment comprises, from the terminus side, sequences P1 and T1, and the other associative region 2 comprises, from the terminus side, sequences P2 and T2. At least sequence T1 or sequence T2 comprises an inherent base sequence contained in the target gene. Desirably, both sequences T1 and T2 comprise an inherent base sequence contained in the target gene. Further, the 3' end protruding double-stranded gene fragment has a sequence NNNNN of one or more nucleotides as a protruding terminus on the 3' end of sequence P2 of one of the strands, and has a sequence of NNNNN of one or more nucleotides as a protruding terminus on the 3' end of the sequence P1 of the other strand. NNNNN means a sequence of one or more nucleotides, and not the presence of five nucleotides.

(ii) The joining DNA region of the double-stranded joining DNA fragment contains sequence A and sequence B as joining DNA regions.

(iii) One of the associative regions 1v of the double-stranded joining DNA fragment comprises, from the terminus side, sequences VT1 and VP1. The other associative region 2v comprises, from the terminus side, sequences VT2 and VP2. Sequences VP1 and VT1 and sequences P1 and T1, respectively, have homologous base sequences. Sequences VP2 and VT2 and sequences P2 and T2, respectively, have homologous base sequences.

In the above specific mode:

The 3' end protruding double-stranded gene fragment is denoted by P1-T1-target gene-T2-P2 (where the 3' end protruding terminus is not denoted; when the 3' end protruding terminus is denoted as NNNNN, it can be denoted as NNNNN-P1-T1-target gene-T2-P2-NNNNN). Further, the double-stranded joining DNA fragment can be denoted as VT2-VP2-sequence B-sequence A-VP1-VT1. The joined DNA fragment is a DNA fragment having at least one sequence denoted by VT2-VP2-sequence B-sequence A-VP1-VT1-target gene-VT2-VP2-sequence B-sequence A-VP1-VT1. VT2-VP2 and T2-P2 are homologous sequences, and VP1-VT1 and P1-T1 are homologous sequences. Thus, the joined DNA fragment can also be said to be a DNA fragment having at least one sequence denoted by T2-P2-sequence B-sequence A-P1-T1-target gene-T2-P2-sequence B-sequence A-P1-T1.

<The 3' End Protruding Double-stranded Gene Fragment in the Embodiment>

The 3' end protruding double-stranded gene fragment will be described in greater detail.

Sequences P1 and P2 are not specifically limited other than that they be sequences and lengths specifically hybridizing with the primers that are needed for priming. The length, for example, is 10 bases or more, desirably 10 to 100 bases, preferably 15 to 50 bases, and more preferably, 15 to 30 bases. One or both of regions P1 and P2 can be an inherent base sequence of the target gene. The whole sequences of one or both of regions P1 and P2 can be a sequence that is a portion of the sequence of the target gene. As set forth further below, regions P1 and P2 are comprised of base sequences that are homologous with double-stranded joining DNA fragment regions VP1 and VP2, respectively.

The 3' end protruding double-stranded gene fragment has a sequence T1 at the inside of sequence P1 and a sequence T2 at the inside of sequence P2. One or both of T1 and T2 have inherent base sequences of the target gene. Sequences such as spacer sequences can be present between sequence P1 and sequence T1, between sequence P2 and sequence T2, between sequence T1 and the sequence of the target gene when sequence T2 comprises an inherent sequence of the target gene, and between sequence T2 and the sequence of the target gene when sequence T1 comprises an inherent sequence of the target gene to an extent that does not hinder the formation of double strands of the individual strands of the 3' end protruding double-stranded gene fragment and the individual strands of VT2-VP2-sequence B-sequence A-VP1-VT1 in denaturation, re-association, and the DNA synthesis reaction. Details of sequence T1 and sequence T2 will be explained below.

The 3' protruding terminus of the 3' end protruding double-stranded gene fragment, for example, is a sequence comprised of at least one nucleotide differing from the sequence of the double-stranded joining DNA fragment provided on the 3' termini of sequence P1 and sequence P2. As set forth above, the 3' protruding terminus is provided to prevent nucleic acid elongation beginning at the two 3' termini of the various strands of the 3' end protruding double-stranded gene fragments in the denaturation, re-association, and DNA synthesis reactions with VT2-VP2-sequence B-sequence A-VP1-VT1.

Accordingly, the nucleotide or nucleotide strand NNNNN provided on the 3' terminus of the strand denoted as the antisense strand of the 3' end protruding double-stranded gene fragment is not specifically limited other than that it be a non-complementary nucleotide or a nucleotide strand including at least one portion that is a non-complementary sequence with the sequence of the 5'-side (sequence A side) of sequence VP1 of the strand denoted as the sense strand of double-stranded joining DNA fragment VT2-VP2-sequence B-sequence A-VP1-VT1. The length is, for example, one base or more, desirably 2 to 100 bases, and preferably, 5 to 50 bases.

Similarly, the nucleotide or nucleotide strand NNNNN provided on the 3' terminus of the strand denoted as the sense strand of the 3' end protruding double-stranded gene fragment is not specifically limited other than that it be a non-complementary sequence or a nucleotide strand including at least one portion that is a non-complementary sequence with the sequence joined with the 5' side (sequence B side) of the region VP2 of the antisense strand of double-stranded joining DNA fragment VT2-VP2-sequence B-sequence A-VP1-VT1. The length is, for example, one base or more, desirably 2 to 100 bases, and preferably, 5 to 50 bases.

The nucleotide, or the nucleotide on the 3' end of the nucleotide strand, provided on the 3' protruding terminus of sequence P1 (P2), can be a compound capable of inhibiting the DNA-elongating reaction from the 3' end of the sequence P1 (P2). In that case, the nucleotide, or the nucleotide strand NNNNN, provided on the 3' terminus of sequence P1 can be a nucleotide that is complementary to the sequence of the 5'-side (sequence A side) of the sequence VP1 of the strand denoted as the sense strand of double-stranded joining DNA fragment VT2-VP2-sequence B-sequence A-VP1-VT1. Similarly, the nucleotide or nucleotide strand NNNNN provided on the 3' terminus of sequence P2 can be a nucleotide that is complementary to the sequence of the 5'-side (sequence A side) of sequence VP2 of the strand that is denoted as the antisense strand of double-stranded joining DNA fragment VT2-VP2-sequence B-sequence A-VP1-VT1.

The method of preparing the 3' end protruding double-stranded gene fragment is not specifically limited. For example, it can be prepared by PCR using the target gene as template. Below, in an example where a double-stranded DNA fragment comprising a portion of a variable region and a constant region of an immunoglobulin gene is employed as the target gene fragment will be described according to FIG. 13. (Part of) the sequence of the primer 2 shown in FIG. 13 corresponds to the sequence T1 of a target double-stranded DNA fragment comprising a 3' protruding terminus. Primers 4 and 3 correspond to sequences P1 and P2 of the double-stranded DNA fragment comprising a 3' protruding terminus. Further, the sequence derived from the constant region joined to the upstream side of primer 3 corresponds to the sequence T2 of the 3' end protruding double-stranded gene fragment.

First, magnetic beads are used to recover mRNA coding for the target gene. Next, a reverse transcription reaction employing reverse transcriptase is used to synthesize cDNA. Next, terminal deoxynucleotidyl transferase is used to add poly (dG) to the 3' terminus of the cDNA that has been synthesized. Next, the immunoglobulin cDNA (synthesized on magnetic beads) with poly(dG) added to the 3' terminus thereof is employed as template and primer 1 (immunoglobulin gene constant region) and primer 2 (for associating with poly(dG) to synthesize DNA) are used to conduct the first cycle of PCR.

After completing one cycle of PCR, the product is diluted by about 100-fold, for example, and employed as template in a second cycle of PCR. Primers 4 and 3 are employed. Primer 4 is designed so that the sequence on its 3' terminus side overlaps with the 5'-terminus side of primer 2 employed in the first PCR cycle, causing primer 4 to connect to that region. Primer 3 is positioned in a constant region, and is designed to position itself inside primer 1 employed in the first PCR cycle. However, primer 3 can have a sequence that partially overlaps with primer 1, or can have a sequence that does not overlap with primer 1. If the DNA fragment containing a constant region of immunoglobulin in the first PCR cycle is amplified and by using primers 3 and 4, it is possible to amplify DNA containing a constant region of immunoglobulin, that is, a double-stranded DNA fragment that comprises a constant region of immunoglobulin as a target gene sequence. This is a method of PCR known as rapid amplification of cDNA ends (RACE). The primer 4+2 sequence is an artificial sequence synthesized with primers 2 and 4 in two PCR cycles, and does not comprise a characteristic (inherent) sequence in the template sequence.

In the second cycle of PCR, primer 4 is specifically connected (because it has the sequence of primer 2) to the 3' end region of the DNA fragment amplified in the first cycle of PCR and primer 3 is connected to the immunoglobulin constant region further inside primer 1. As a result, specific amplification is conducted. In this case, the 4+2 sequence will necessarily be present on one side of the PCR product. However, in reality, since the primers employed combine with non-target DNA with similar base sequences, non-specific PCR products also sometimes end up being synthesized. For example, when primer 4 nonspecifically connects to another DNA fragment, the sequence of primer 4 will be present on the terminus of the DNA fragment that is synthesized, but the sequence of primer 2, that is, sequence T1, will not be present to the inside.

If primer 3 connects to a non-target gene having a similar base sequence and DNA amplification is conducted, the sequence of the constant region, that is, sequence T2, will not be present in the DNA fragment. The sequence that is formed with primer 3 is one that is specific (inherent) to the template.

The PCR products obtained in the second cycle of PCR, that is, the method of providing at least one nucleotide on the 3' protruding terminus of the double-stranded DNA fragment containing the sequence of the target gene (antibody gene) is not specifically limited. An example is the method of subjecting a double-stranded DNA fragment containing the sequence of a target gene and a polydeoxynucleotide to the action of deoxynucleotide terminal transferase to obtain a double-stranded DNA fragment having a 3' protruding terminus. Using this method, it is possible to obtain a 3' end protruding double-stranded gene fragment with at least one nucleotide on each 3' terminus.

<The Double-stranded Joining DNA Fragment in the Embodiment>

The "double-stranded joining DNA fragment" (VT2-VP2-sequence B-sequence A-VP1-VT1) is a double-stranded joining DNA fragment that comprises a sequence A and a sequence B, comprises a region VP1 comprised of a base sequence homologous with sequence P1 on the terminus side of sequence A, comprises a region VP2 comprised of a base sequence homologous with sequence P2 on the terminus side of sequence B, comprises on the terminus side of region VP1 a region VT1 comprised of a base sequence homologous with a portion of sequence T1 to the inside of sequence P1 in the 3' end protruding double-stranded gene fragment, and comprises on the terminus side of region VP2 a region VT2 comprised of a base sequence homologous with a portion of sequence T2 to the inside of sequence P2 in the 3' end protruding double-stranded gene fragment. However, at least sequence T1 or sequence T2 in the 3' end protruding double-stranded gene fragment comprises a base sequence that is inherent to the target gene. The sequence of the protruding terminus on the 3' end of sequence P2 in the 3' end protruding double-stranded gene fragment is a sequence that is nonhomologous with sequence B of one of the strands of the double-stranded joining DNA fragment or the sequence containing the dideoxynucleotide. The sequence of the protruding terminus on the 3' end of sequence P1 in the 3' end protruding double-stranded gene fragment is a sequence that is nonhomologous with sequence A of the other stand of the double-stranded joining DNA fragment or the sequence containing the dideoxynucleotide. A "region" as referred to in the present description is comprised of a sequence on the sense strand and the sequence on the antisense strand at the corresponding spot.

As will be understood from the schemes shown in FIGS. 2 and 3, sequences T1 and T2 of the 3' end protruding double-stranded gene fragment play an internal sequencing role for VT1 and VT2 in the VT2-VP2-sequence B-sequence A-VP1-VT1, which is the "double-stranded joining DNA fragment." They promote the selective re-association of the 3' end protruding double-stranded gene fragment containing the target gene sequence and VT2-VP2-sequence B-sequence A-VP1-VT1, and the subsequence DNA synthesis reaction. Here, the term "internal sequence" indicates a sequence that is peculiar to the target gene sequence, that is an inside sequence (T1 and T2) of P1 and P2 having a sequence homologous with the amplification primer sequence positioned on the terminus of the target gene sequence, and that is homologous with VT1 and VT2 of the double-stranded joining DNA fragment. Thus, the non-target gene fragment is schematically denoted as P1-non-target gene fragment-P2, P1-T1-non-target gene fragment-P2, or P1-non-target gene fragment-T2-P2. The term "internal sequencing role" refers to a sequence playing the roles of promoting the specific re-association of the double-stranded joining DNA fragment and the double-stranded gene fragment and the subsequent DNA synthesis reaction, and inhibiting the re-association with non-target double-stranded DNA fragments and the subsequent DNA synthesis reaction.

Sequence T1 of the 3' end protruding double-stranded gene fragment, region VT1 of VT2-VP2-sequence B-sequence A-VP1-VT1, sequence T2 of the 3' end protruding double-stranded gene fragment, and region VT2 of VT2-VP2-sequence B-sequence A-VP1-VT1 are not specifically limited so long as they are comprised of mutually homologous base sequences. The length of VT1 and VT2 is, for example, one or more bases, desirably 2 to 100 bases, and preferably 5 to 50 bases. Sequence P1+T1, sequence P2+T2, region VP1+VT1, and region VP2+VT2 desirably have Tm values of 60° C. or higher, preferably from about 68° C. to 70° C.

Sequence A of VT2-VP2-seugence B-sequence A-VP1-VT1 is not specifically limited. For example, it can be an upstream sequence of the target gene fragment, introns, exons, fluorescent protein genes, and various tag sequences such as His tags, as well as promoters, enhancers, and the like that can control the expression of various genes within bacterial and animal cells. Sequence B of VT2-VP2-seugence B-sequence A-VP1-VT1 is not specifically limited. For example, it can be a downstream sequence of the target gene fragment, introns, exons, fluorescent protein genes, and various tag sequences such as His tags, or a polyadenylation signal and the like.

When employing a promoter sequence and polyadenylation signal as sequence A and sequence B, respectively, to the extent that the expression of the target gene in the host cell is not impeded, it is possible for sequences such as spacer sequences to be present between the various sequences, upstream of sequence A, and downstream of sequence B.

The length between sequence A and sequence B in the gene joining double-stranded DNA fragment is not specifically limited. Neither is the length between sequence A and region VP1 nor the length between sequence B and region VP2 specifically limited. To the extent that annealing of the double-stranded DNA fragment having a 3' protruding terminus is not hindered, it is possible for a sequence such as a spacer sequence of suitable length to be present between regions VP1 and VT1 and between regions VP2 and VT2.

The method of producing a "double-stranded joining DNA fragment" in the form of VT2-VP2-sequence B-sequence A-VP1-VT1 is not specifically limited. It can be produced by a combination of known methods. An example of a method of producing VT2-VP2-sequence B-sequence A-VP1-VT1 will be specifically described below according to FIG. 14.

A vector (pCMV-EGFP) having sites recognized by restriction enzyme 1 (BamHI) and restriction enzyme 2 (NotI) was treated with restriction enzyme I. A linker (poly (dG/dC)-EcoRV linker), sequentially containing the known sequence (poly(dG/dC)) and a site recognized by the restriction enzyme 3 (EcoRV), was inserted at a site recognized by restriction enzyme I. Next, the linker-inserted vector obtained was treated with restriction enzymes 2 and 3 and the sequence from the site recognized by restriction enzyme 3 to the site recognized by restriction enzyme 2 was replaced with a partial sequence (human immunoglobulin constant region obtained from human peripheral blood lymphocyte cDNA by PCR) of the target gene having an upstream restriction enzyme 3 cutting plane and a downstream restriction enzyme 2 cutting plane. An ampicillin resistance gene and a replication starting point were inserted at the restriction enzyme 3 site of the vector obtained. Next, the kanamycin resistance gene and replication starting point were removed from the vector to obtain a vector into which human immunoglobulin heavy chain gene joining double-stranded DNA fragment had been inserted (pMiniCMV-hIgG). Using this vector as template, PCR was conducted with primer containing a poly(dG/dC) region and a partial target gene sequence (immunoglobulin constant region) to obtain VT2-VP2-sequence B-sequence A-VP1-VT1 in the form of a human immunoglobulin heavy chain gene joining double-stranded DNA fragment.

In this case, the poly(dG/dC) corresponded to region VT1, the portion of the human immunoglobulin constant region corresponded to region VT2, the CMV promoter corresponded to sequence A, and the remaining portion of the immunoglobulin constant region and the polyadenylation signal corresponded to sequence B. At least a portion of the sequence between the multicloning site (MCS) and the poly (dG/dC) corresponded to region VP1, and at least a portion of the sequence of the human immunoglobulin constant region corresponded to region VP2.

(1) Thermal Denaturation, Re-association, and a DNA Synthesis Reaction (1)

A cycle of thermal denaturation, re-association, and a DNA synthesis reaction will be described. In FIG. 2, it is denoted as thermal denaturation, re-association, and DNA synthesis (1).

A sample containing a "3' end protruding double-stranded gene fragment" denoted by P1-T1-target gene-T2-P2 and a "double-stranded joining DNA fragment" denoted by VT2-VP2-sequence B-sequence A-VP1-VT1 was subjected to thermal denaturation, re-association, and a DNA synthesis reaction. First, re-association (annealing) following thermal denaturation formed a stable double strand between the region P1+T1 of one of the strands (antisense strand) of the "3' end protruding double-stranded gene fragment and the region VP1+VT1 of one of the strands (sense strand) of the "double-stranded joining DNA fragment." Similarly, a stable double strand was formed between region P2+T2 of the sense strand of the "3' end protruding double-stranded gene fragment" and the region VP2+VT2 of the antisense strand of the "double-stranded joining DNA fragment." The two double strands thus obtained were then subjected to a DNA synthesis reaction based on DNA polymerase. The DNA synthesis reaction (nucleic acid chain-elongating reaction) elongated the nucleic acid with the region VT1 of the sense strand of VT2-VP2-sequence B-sequence A-VP1-VT1 as starting point, synthesizing a strand-elongation product (2). It also elongated the nucleic acid with the region VT2 of the antisense strand VT2-VP2-sequence B-sequence A-VP1-VT1 as starting point, synthesizing a strand elongation product (1).

Figure 3:
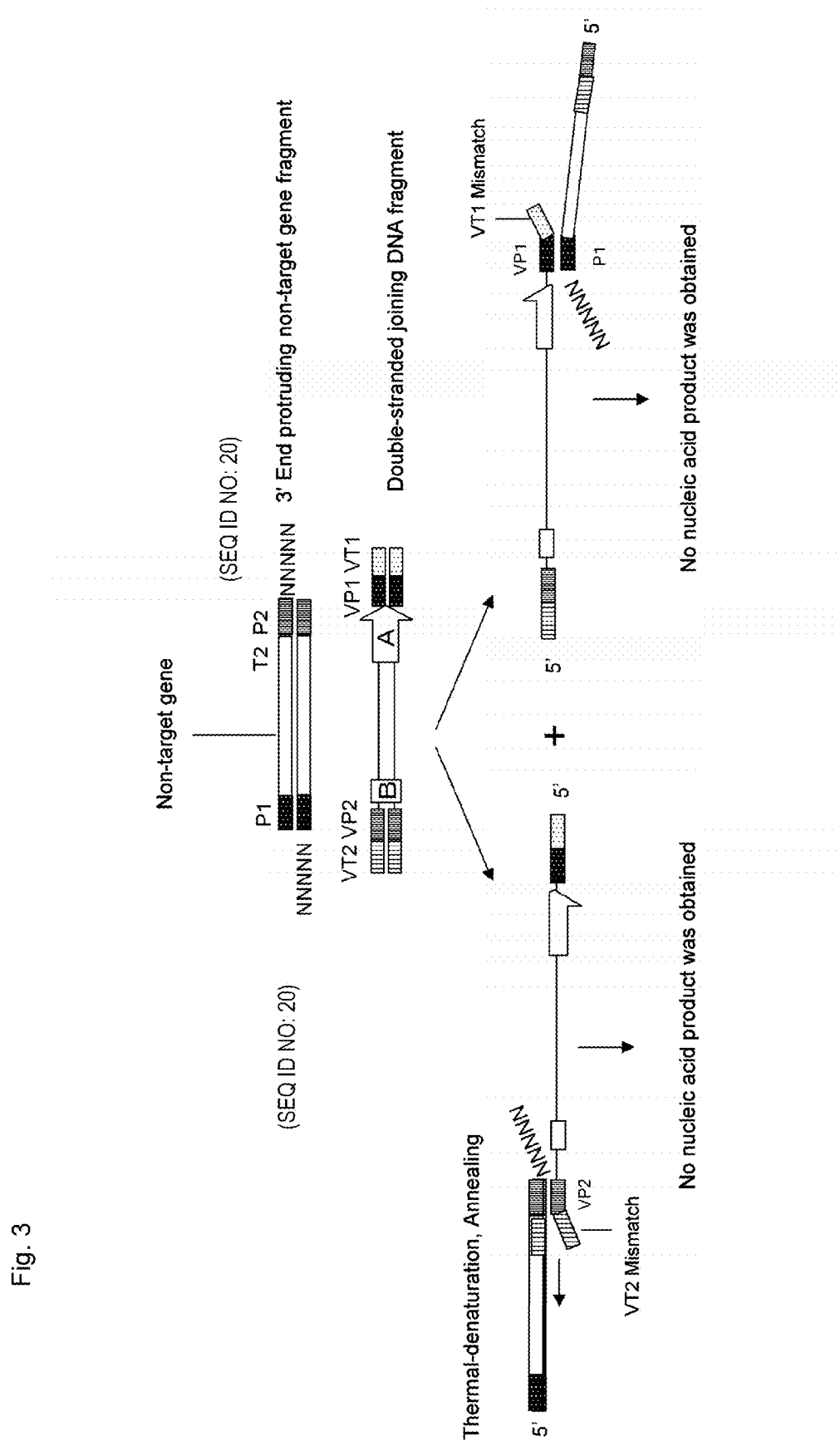
FIG. 3 is a reaction scheme describing the case where a nucleic acid elongation product is not produced and a joined DNA fragment cannot be obtained in thermal denaturation, re-association, and a DNA synthesis reaction in a first embodiment of carrying out the first aspect of the present invention.

Since the VT2-VP2-sequence B-sequence A-VP1-VT1 contained region VT1 and/or VT2 comprised of a base sequence that was homologous with internal sequence T1 and/or T2, which were inherent sequences of the 3' end protruding double-stranded gene fragment, it was possible to conduct selective re-association with DNA fragments having 3' protruding termini and the subsequent DNA synthesis reaction. However, when preparing a 3' end protruding double-stranded gene fragment, primer 4 shown in FIG. 13 connected nonselectively to DNA fragments containing the sequences of non-target genes, producing double-stranded DNA fragments in which no sequence T1 was present to the inside of sequence P1. Further, primer 3 connected to non-target genes having a similar base sequence, producing double-stranded DNA fragments in which no sequence T2 was present to the inside of sequence P2. When the VT2-VP2-sequence B-sequence A-VP1-VP2 and double-stranded DNA fragments in which no sequence T1 was present to the inside of sequence P1 and no sequence T2 was present to the inside of sequence P2 were subjected to a DNA synthesis reaction following thermal denaturation and re-association, the reaction did not proceed and no joined product was obtained, as shown in FIG. 3.

Further, there are 3' end protruding termini denoted by NNNNN on the two 3' ends of regions P1 and P2 in the "3' end protruding double-stranded gene fragments". These protruding termini (single-strand nucleotides) do not have a strand-extending function in the DNA synthesis reaction. That is, in the scheme producing nucleic acid elongation product (1) on the left side of FIG. 2, the NNNNN following the T2-P2 of the sense strand of the 3' end protruding double-stranded gene fragment does not hybridize with the sequence adjacent to VP2 lying between VP2 and sequence B or the sequence adjacent to the VP2 of sequence B following VT2-VP2 of the opposite strand on the associated one (the antisense strand of the double-stranded joining DNA fragment). Since the NNNNN following T2-P2 does not hybridize with the sequence adjacent to the VP2 of sequence B following VT2-VP2, no nucleic acid elongation with regions P1 and P2 as starting points is observed. Similarly, in the scheme shown in nucleic acid elongation product (2) on the right side of FIG. 2, since the NNNNN following the T1-P1 of the antisense strand of the 3' end protruding double-stranded gene fragment does not hybridize with the sequence adjacent to VP1 lying between VP1 and sequence A or the sequence adjacent to the VP1 of sequence A following the VT1-VP1 of the sense strand of the double-stranded joining DNA fragment, no nucleic acid elongation with regions P1 and P2 as starting points is observed.

The conditions of the thermal denaturation of the first cycle can be identical to the conditions normally adopted in PCR. For example, thermal denaturation can be conducted for 20 to 60 seconds at 90 to 98° C. The conditions of the re-association of the first cycle can be identical to the conditions normally adopted in PCR. For example, re-association can be conducted for from 30 seconds to 6 minutes at 60 to 72° C. The DNA synthesis reaction of the first cycle can be conducted under the same conditions as those normally adopted in PCR. For example, it can be conducted for from 30 seconds to 6 minutes at 68 to 72° C. Depending on the optimal temperature of enzymatic activity for the DNA polymerase employed, annealing and nucleic acid elongation can be conducted at the same temperature and implemented as a single step.

The first cycle of thermal denaturation, re-association, and DNA synthesis reaction yields a reaction product containing nucleic acid elongation products (1) and (2). Although not shown in FIG. 2, these reaction products may contain fragments incorporating non-target genes, as shown in FIG. 3.

(2) Thermal Denaturation, Re-association, and DNA Synthesis Reaction (2)

The second cycle of thermal denaturation, re-association, and DNA synthesis reaction will be described. In FIG. 2, this is denoted as thermal denaturation, re-association, and DNA synthesis (2).

The first cycle reaction product is thermally denatured and then re-associated (annealed). As a result, since one of the strands of nucleic acid elongation products (1) and (2) does not have a 3' end protruding sequence in the form of NNNNN on the "3' end protruding double-stranded gene fragment", and the sequence other than NNNNN of the "3' end protruding double-stranded gene fragment" is homologous, this portion forms a double strand. Next, by means of a DNA synthesis reaction, this double strand serves each other as a template and the nucleic acid elongates from the 3' termini of both strands, yielding a joined DNA fragment (VT2-VP2 -sequence B-sequence A-target gene-sequence B-sequence A-VP1-VT1) in which a double-stranded joining DNA fragment is joined to each end of the target gene. Additionally, since the single-stranded DNA fragments from nucleic acid elongation products (1) and (2) having NNNNN 3' end protruding sequences have NNNNN sequences on the 3' ends thereof, they cannot form double strands in re-association (annealing). As a result, nucleic acid elongation products with these single-stranded DNA fragments as templates do not form.

The second cycle of thermal denaturation, re-association, and DNA synthesis reaction yields the above joined DNA fragment (VT2-VP2-sequence B-sequence A-target gene-sequence B-sequence A-VP1-VT1). Although not shown, the single-strand DNA fragments with 3' end protruding sequences in the form ofNNNNN that have not employed as templates of nucleic acid elongation productions (1) and (2) are contained (remain) in this reaction product in addition to the nonspecific DNA fragments produced by the first cycle of thermal denaturation, re-association, and DNA synthesis reaction.

As set forth further below, sequence A-target gene-sequence B is the joined unit in the joined DNA fragment (VT2-VP2-sequence B-sequence A-target gene-sequence B-sequence A-VP1-VT1).

(3) Thermal Denaturation, Re-association, and DNA Synthesis Reaction (3)

Although not shown in FIG. 2, in the first aspect of the present invention, a third cycle of thermal denaturation, re-association, and DNA synthesis reaction can be conducted following the second cycle of thermal denaturation, re-association, and DNA synthesis reaction.

In the third cycle of thermal denaturation, re-association, and DNA synthesis reaction, the homologous regions of any two of the single strands produced by denaturation of the VT2-VP2-sequence B-sequence A-target gene-sequence B-sequence A-VP1-VT1 that is the nucleic acid synthesis product of the second cycle hybridize, and this hybridized double strand serves as template in conducting nucleic acid elongation in a DNA synthesis reaction to obtain a double-stranded DNA fragment containing two joined units comprised of the "sequence A-target gene-sequence B" in the nucleic acid synthesis product of the second cycle.

In the fourth and subsequent cycles, this operation is repeated to obtain a polymer of joined units containing three or more of these joined units (sometimes referred to as a "joined unit polymer" hereinafter). Accordingly, in the joining reaction of the third and subsequent cycles, regardless of whether the double-stranded joining DNA fragments, the target gene fragments, or both are depleted, the DNA synthesis substrate is present in the reaction solution, and so long as the activity of the DNA polymerase is maintained, amplification of the joined units takes place. That is, from the third cycle on, when the target gene and joining DNA fragment remain, reactions corresponding to those in the first and second cycles take place, and the polymerization reaction proceeds simultaneously. However, when the target gene and joining DNA fragment do not remain, the repeating units of the polymerization products re-associate while shifting, amplifying the joined units. As a result, more efficient production of joined units is achieved than by the method of producing joined units in which sequence A-target gene-sequence B are joined in that order using the target gene fragment, sequence A-VP1-VT1, and VT2-VP2-sequence B as set forth below.

Mismatch primers can be incorporated into the system of thermal denaturation, re-association, and DNA synthesis reaction in addition to the "3' end protruding double-stranded gene fragment" and double-stranded joining DNA fragment (VT2-VP2-sequence B-sequence A-VP1-VT1) to specifically amplify joined units from the joined unit polymer, as set forth further below. In that case, so that the mismatch primers do not prime the various single strands of the double-stranded joining DNA fragments that have been denatured, re-association (annealing) is desirably conducted at an elevated temperature (for example, 65 to 72° C.). Further, the mismatch primers can be incorporated into the reaction system and nucleic acid elongation can be conducted at the same temperature as annealing. In that case, the thermal denaturation, re-association, and DNA synthesis reaction can be conducted as follows, by way of example: thermal denaturation: 20 to 60 seconds at 90 to 98° C.; re-association and DNA synthesis reaction: 30 seconds to 6 minutes at 65 to 72° C. Two to 10 cycles of this cycle can be conducted. Desirably, thermal denaturation is conducted for 30 to 50 seconds at 93 to 95° C. and re-association and the DNA synthesis reaction are conducted for 1 to 5 minutes at 68 to 70° C., with 4 to 8 cycles being conducted. Here, the term "cycle" means one cycle of thermal denaturation, re-association, and DNA synthesis reaction.

The joined DNA fragment that is obtained by such a reaction is a polymer that contains multiple linearly joined units of sequence A-target gene-sequence B depending on the number of cycles of thermal denaturation, re-association, and DNA synthesis reaction. In addition to the joined unit, this polymer contains sequence A-VP1, VT1 and VT2-VP2-sequence B on the termini thereof.

[The Step of Preparing the Joined Unit]

The joined DNA fragment that is obtained as a nucleic acid synthesis product in the first aspect of the present invention will contain one joined unit, depending on the number of cycles of thermal denaturation, re-association, and DNA synthesis reaction. If three or more cycles of thermal denaturation, re-association, and DNA synthesis reaction are conducted, a joined unit polymer with multiple joined units will be obtained. The ultimate object of the present invention is to obtain a joined unit denoted by sequence A-target gene-sequence B. Accordingly, the first aspect of the present invention desirably further comprises a step of preparing joined units comprised of sequence A-target gene-sequence B from the joined unit polymer.

The step of preparing a joined unit is not specifically limited. For example, a method employing a restriction enzyme to specifically cut the joined unit polymer upstream and downstream of the joined unit, a method of selectively amplifying the joined unit employing the joined unit polymer as template, or the like can be employed. The method of employing a restriction enzyme can be implemented by introducing restriction enzyme cleaving sequences into the sequence outside sequence B and outside sequence A of the sequence A-target gene-sequence B in the joined unit polymer.

The method of selectively amplifying the joined unit using the joined unit polymer as template can be implemented, for example, by PCR using a mismatch forward primer containing on the 3' end thereof the sequence A of the sense strand of the double-stranded joining DNA fragment (VT2-VP2-sequence B-sequence A-VP1-VT1), or a sequence identical to a sequence upstream from it, and a mismatch reverse primer containing on the 3' end thereof sequence B, or a sequence complementary to a sequence downstream from it. FIG. 4 shows the PCR scheme for selectively amplifying the joined unit using these mismatch primers. As shown in FIG. 4, the use of mismatch primers permits the efficient selective amplification of joined units separated from the joined unit polymer. Sequences that are not homologous to the double-stranded joining DNA fragments serving as template will be added to the two termini of joined units synthesized by at least two cycles of PCR using the joined unit polymer as template and employing a mismatch forward primer and mismatch reverse primer.

The conditions of the PCR employing mismatch primers are not specifically limited. Commonly known PCR conditions can be employed. However, for example, implementation of about 25 to 50 cycles of reactions for 20 to 60 seconds at 90 to 98° C., 20 to 60 seconds at 55 to 65 seconds, and 3 to five minutes at 70 to 74° C. is possible.

Figure 4:
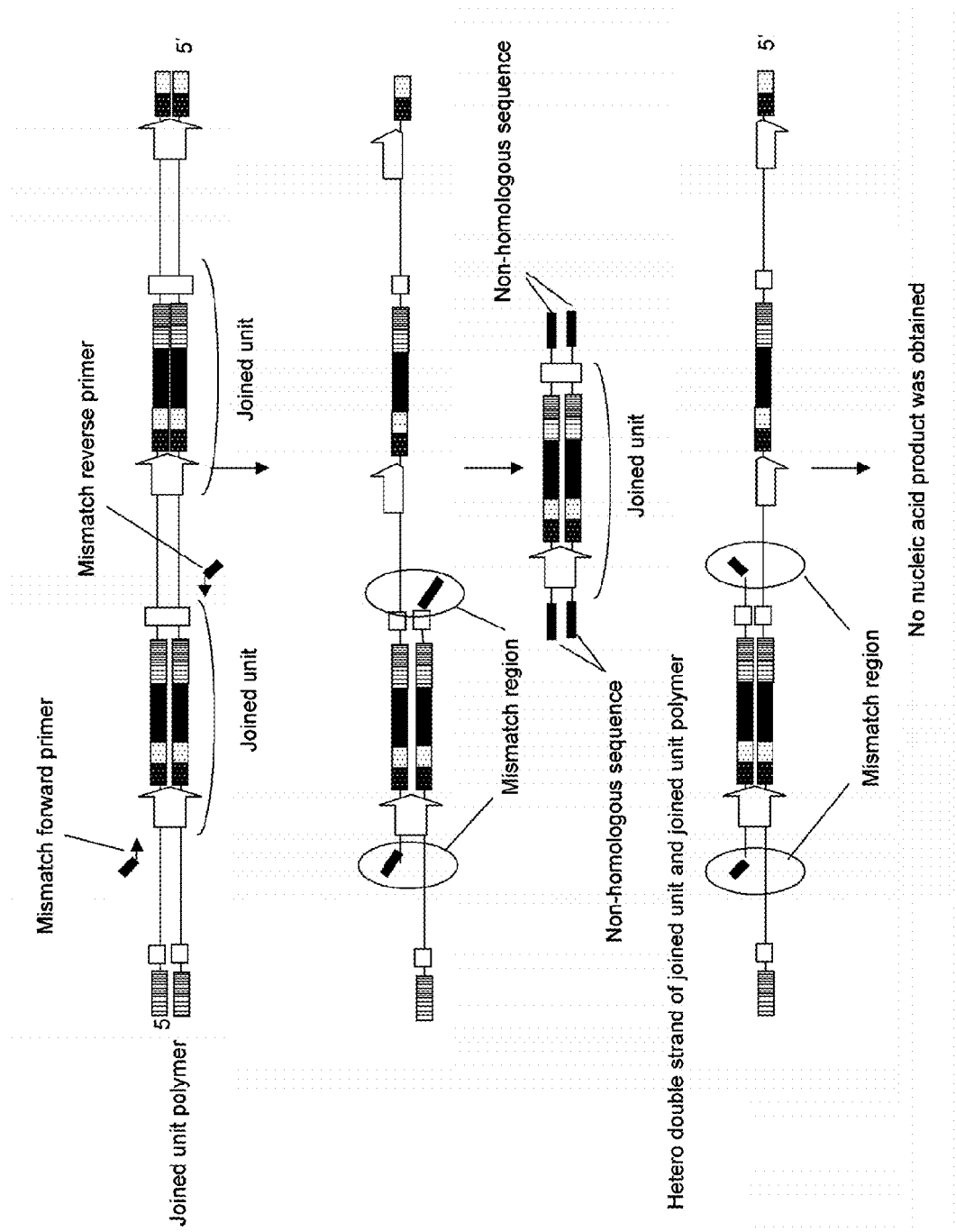
FIG. 4 is a reaction scheme describing a method of obtaining a desired double-stranded DNA fragment from a joined DNA fragment obtained according to an embodiment of carrying out the first aspect of the present invention.
Figure 5:
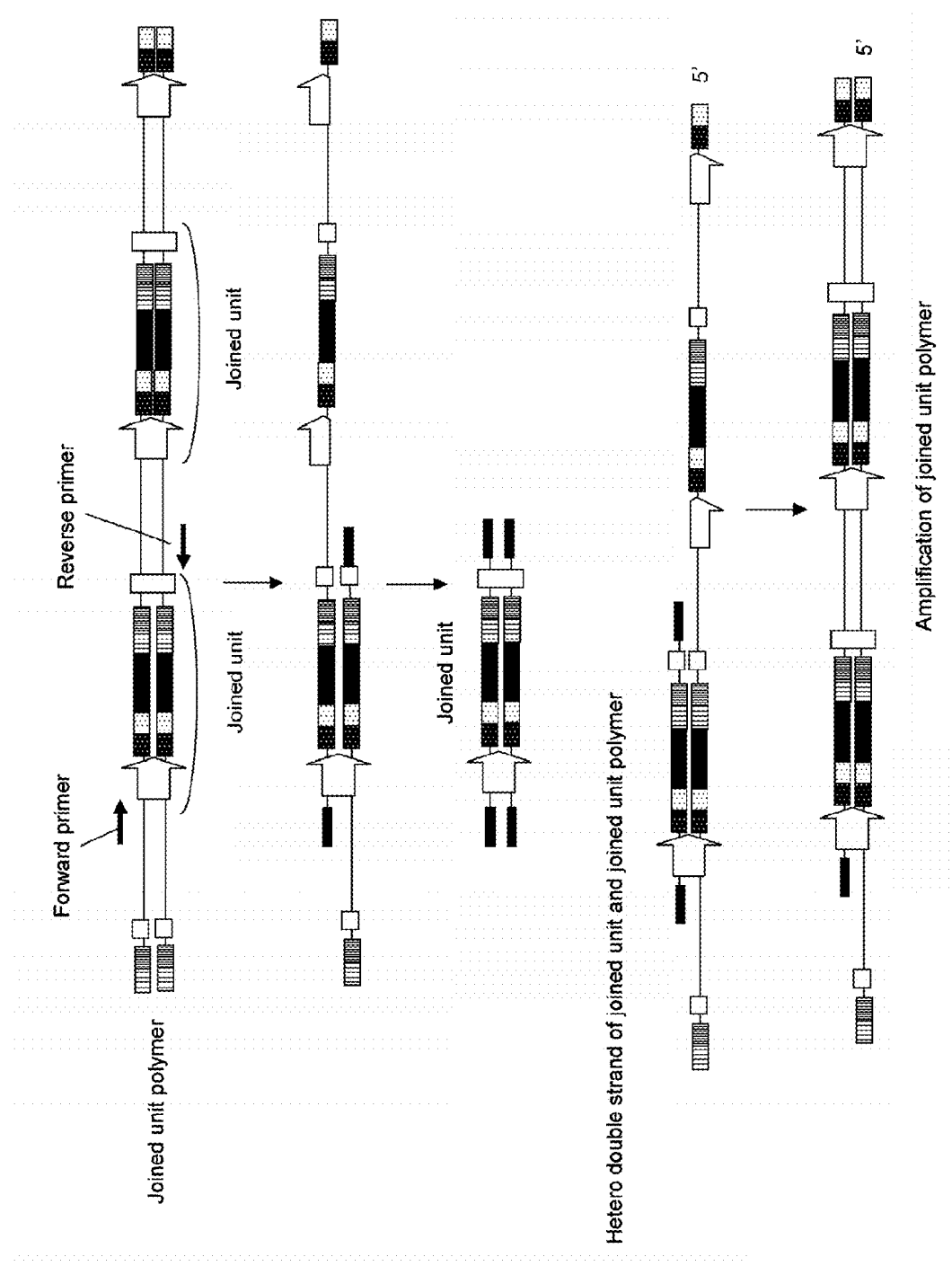
FIG. 5 is a reaction scheme describing the case where a desired double-stranded DNA fragment cannot be obtained by a method of obtaining a desired double-stranded DNA fragment from a joined DNA fragment obtained according to an embodiment of carrying out the first aspect of the present invention.
Figure 6:
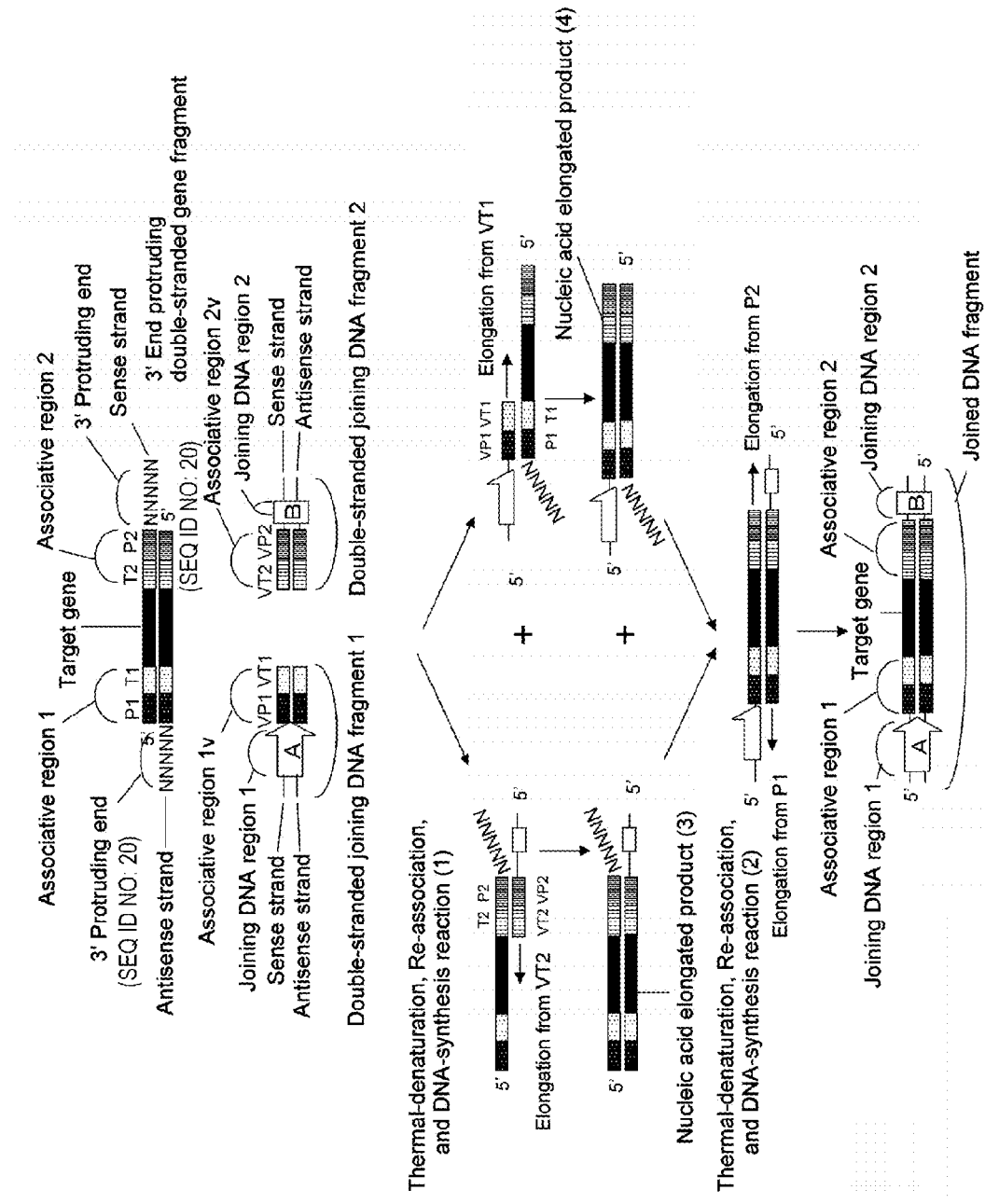
FIG. 6 is a reaction scheme describing an embodiment of carrying out the second aspect of the present invention.
Figure 7:
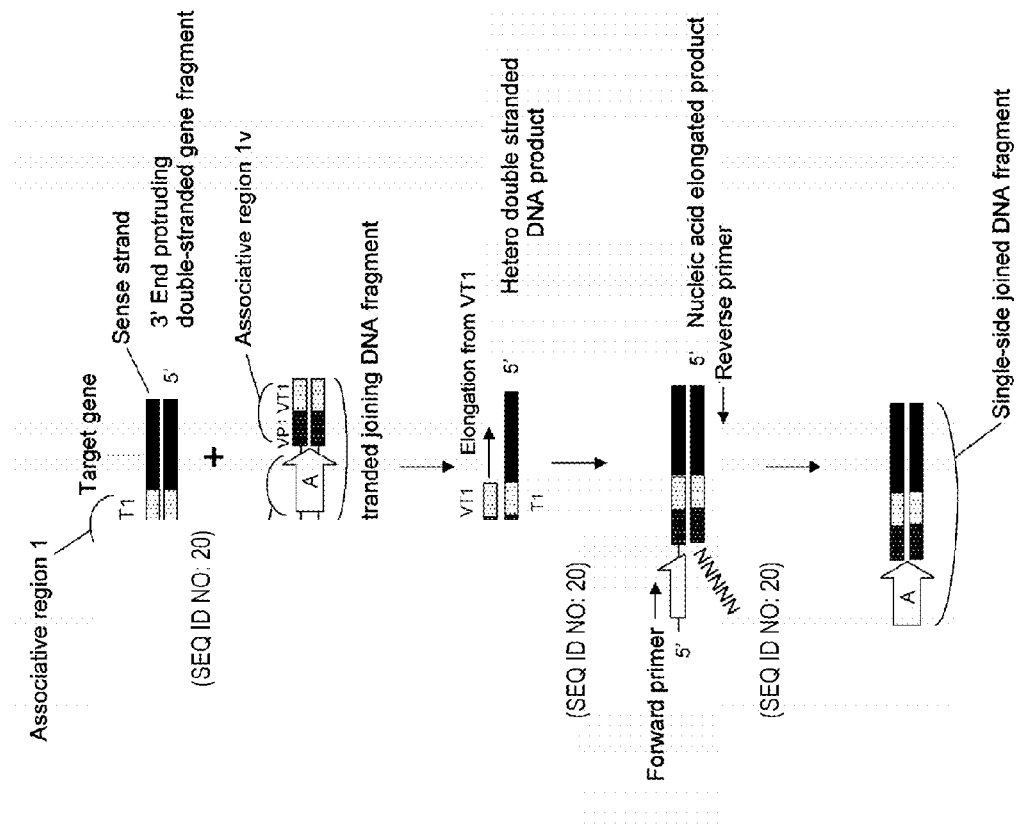
FIG. 7 is a reaction scheme describing an embodiment of carrying out the third aspect of the present invention.
Figure 8:
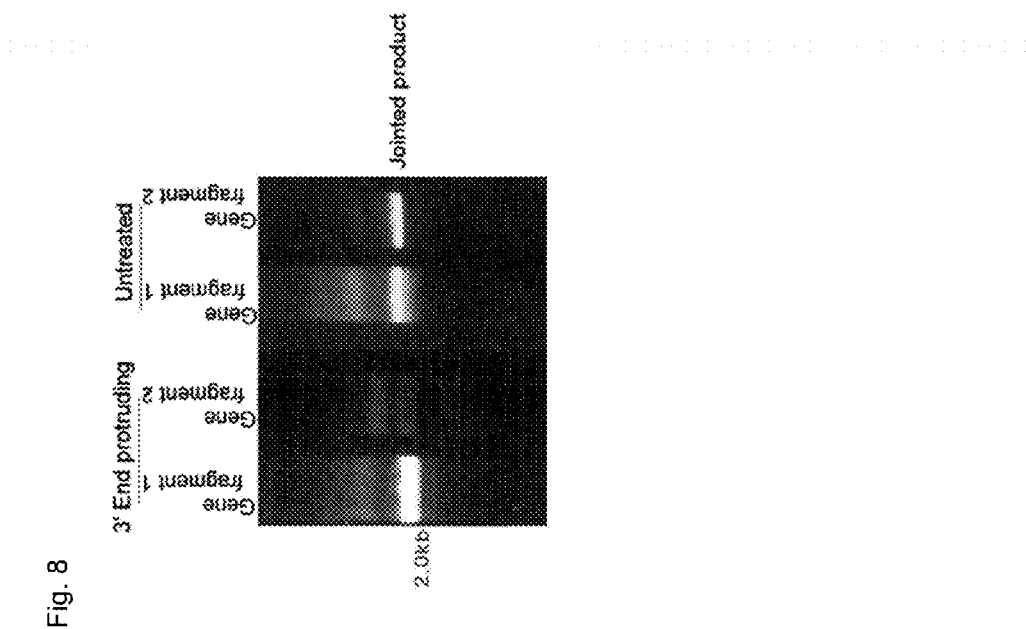
FIG. 8 is a drawing confirming, by agarose gel electrophoresis, an amplification product obtained by subjecting a human -chain gene double-stranded joining DNA fragment and a mixture of target and non-target gene fragments to the selective joining method. Lane 1: Joined unit (human γ-chain gene expression unit) comprised of a promoter-human γ-chain gene-polyadenylation signal obtained by joining a 3' end polynucleotide-added target gene fragment 1 to a human γ-chain gene double-stranded joining DNA fragment. Lane 2: Joined unit obtained by joining a 3' end polynucleotide added non-target gene fragment 2 to a human γ-chain gene double-stranded joining DNA fragment. Lane 3: a human γ-chain gene expression unit obtained by joining a target gene fragment 1 to a human γ-chain gene double-stranded joining DNA fragment. Lane 4: a joined unit obtained by joining a non-target gene fragment 2 to a human γ-chain gene double-stranded joining DNA fragment.

FIG. 5 shows the scheme of PCR employing primers not having mismatch regions on the 5' side thereof. As indicated in FIG. 5, when the Omer employed is not a mismatch primer, the joined unit polymer is amplified along with the joined unit, making it difficult to selectively amplify the joined unit alone. That is, joined units synthesized by at least two cycles of PCR using a forward primer and a reverse primer with the joined unit polymer as template will be homologous with the joined unit polymer serving as template. In the third and subsequent cycles of PCR, two forms of reaction advance in parallel. One is a reaction in which the forward primer and reverse primer anneal to the joined units that have been synthesized, amplifying the joined units. The other is a reaction in which the joined units anneal to the joined unit polymer, forming hetero double-stranded DNA, and amplifying the joined unit polymer. When the latter reaction takes place with precedence over the former reaction, it becomes difficult to efficiently amplify the joined unit. By contrast, as shown in FIG. 4, joined units that have been synthesized from joined unit polymer using mismatch primers have sequences that are not homologous with the template on the two termini sides thereof. Thus, even when they anneal to the joined unit polymer and form hetero double-stranded DNA fragments, no DNA elongation reaction takes place. As a result, the joined unit polymer is not amplified.

[Second Aspect of the Present Invention]

The second aspect of the present invention is a method in which the double-stranded joining DNA fragment of the first aspect of the present invention is employed by dividing it into two double-stranded joining DNA fragments 1 and 2 having the sequences schematically denoted by joining DNA region 1-region 1 and region 2-joining DNA region 2, respectively. This method inhibits the nonspecific production of joint DNA fragments in which joining DNA region 1 is joined to one side of a non-target gene and joining DNA region 2 is joined to the other side thereof and specifically yields a targeted joined DNA fragment in which joining DNA region 1 is joined to one side of the target gene and joining DNA region 2 is jointed to the other side thereof. The joined DNA fragment that is obtained has the sequence schematically denoted by joining DNA region 1-region 1-target gene-region 2-joining DNA region 2. In the second aspect of the present invention, the "3' end protruding double-stranded gene fragment" is identical to that in the first aspect of the present invention.

The double-stranded joining DNA fragments employed in the second aspect of the present invention are two double-stranded joining DNA fragments having the sequences of a double-stranded joining DNA fragment 1 schematically denoted by joining DNA region 1-region 1 and a double-stranded joining DNA fragment 2 schematically denoted by region 2-joining DNA region 2. An embodiment in which the sequence schematically denoted by joining DNA region 1-region 1 is sequence A-VP1-VT1 and the sequence denoted by region 2-joining DNA region 2 is VT2-VP2-sequence B will be described below.

In the present embodiment, a 3' end protruding double-stranded gene fragment, sequence A-VP1-VT1(double-stranded joining DNA fragment 1), and VT2-VP2-sequence B (double-stranded joining DNA fragment 2) are subjected to at least two cycles of thermal denaturation, re-association, and a DNA synthesis reaction to obtain a nucleic acid synthesis product in the form of a joined DNA fragment having one joined unit consisting of sequence A-target gene-sequence B.

This method will be described according to the scheme of FIG. 6. The 3' end protruding double-stranded gene fragment and the at least two cycles of thermal denaturation, re-association, and DNA synthesis reaction are identical to those described in the embodiment of the first aspect of the present invention set forth above.

Sequence A-VP1-VT1 sequentially comprises a sequence A, a region VP1, and a region VT1. Regions VT1 is present on one of the termini. Region VP1 and region VT1 are respectively comprised of a base sequence homologous with sequence P1 and a base sequence homologous with sequence T1 of the 3' end protruding double-stranded gene fragment. VT2-VP2-sequence B sequentially comprises a region VT2, a region VP2, and a sequence B. Region VT2 is on one terminus. Region VP2 and region VT2 are respectively comprised of a base sequence homologous with sequence P2 and a base sequence homologous with sequence T2 of the 3' end protruding double-stranded gene fragment.

<Sequence A-VP1-VT1>

Sequence A-VP1-VT1 sequentially comprises a sequence A, a region VP1, and a region VT1. However, region VT1 is positioned on one terminus of the double-stranded joining DNA fragment. For the sequence A and regions VP1 and VT1 in sequence A-VP1-VT1, reference can be made to the description in the embodiment of the first aspect above. Sequences such as spacer sequences can be present upstream from sequence A, between sequence A and region VP1, and between regions VP1 and VT1 in sequence A-VP1-VT1 to the extent that annealing to the double-stranded DNA fragment having the 3' protruding terminus is not impeded when subjected to thermal denaturation, re-association, and a DNA synthesis reaction. Sequence A-VP1-VT1 is not specifically limited. For example, sequence A-VP1-VT1 can be obtained by separation using a restriction enzyme treatment from a plasmid containing sequence A-VP1-VT1 as an insert. Further, sequence A-VP1-VT1 can be obtained by employing a template in the form of a plasmid containing a gene joining double-stranded DNA fragment A as an insert and conducting PCR with a forward plasmid containing a sequence identical to a portion of the sequence upstream from sequence A and a reverse plasmid containing a sequence complementary to a portion of the sequence on one of the terminus sides of region VT1.

<VT2-VP2-sequence B>

VT2-VP2-sequence B sequentially comprises a sequence B, a region VP2, and a region VT2. However, region VT2 is positioned on one of the termini of VT2-VP2-sequence B. With regard to sequence B and regions VP2 and VT2 in VT2-VP2-sequence B, reference can be made to the description of the embodiment of the first aspect above. Sequences such as spacer sequences can be present upstream from sequence B, between sequence B and region VP2, and between regions VP2 and VT2 in sequence VT2-VP2-sequence B to the extent that annealing to the double-stranded DNA fragment having the 3' protruding terminus is not impeded when subjected to thermal denaturation, re-association, and a DNA synthesis reaction. VT2-VP2 -sequence B is not specifically limited. For example, VT2-VP2-sequence B can be obtained by separation using a restriction enzyme treatment from a plasmid containing VT2-VP2-sequence B as an insert. Further, VT2-VP2-sequence B can be obtained by employing a template in the form of a plasmid containing VT2-VP2-sequence B as an insert and conducting PCR with a forward plasmid containing a sequence identical to a portion of the sequence upstream from sequence B and a reverse plasmid containing a sequence complementary to a portion of the sequence on one of the terminus sides of region VT2.

(1) Thermal Denaturation, Re-association, and DNA Synthesis Reaction (1)

In the first cycle of thermal denaturation, re-association, and DNA synthesis reaction, a 3' end protruding double-stranded gene fragment, sequence A-VP1-VT1, and VT2-VP2-sequence B are used to conduct thermal denaturation, re-association, and a DNA synthesis reaction. The annealing following thermal denaturation forms a stable double strand between the sequence P1+T1 of the antisense strand of the 3' end protruding double-stranded gene fragment and the region VP1-VT1 of one of the strands (sense strand) of sequence A-VP1-VT1. Similarly, a stable double strand is formed between the sequence P2-T2 of the sense strand of the 3' end protruding double-stranded gene fragment and the region VP2-VT2 of one strand (the antisense strand) of VT2-VP2-sequence B. The subsequent DNA synthesis reaction employing DNA polymerase synthesizes a nucleic acid elongation product (4) in which nucleic acid is elongated with the region VT1 of sequence A-VP1-VT1 as starting point. A nucleic acid elongation product (3) in which the nucleic acid is elongated with region VT2 of VT2-VP2-sequence B as starting point is also synthesized. Since at least one nucleotide is added to the 3' ends of sequences P1 and P2 in the 3' end protruding double-stranded gene fragment, the nucleic acid does not elongate with sequences P1 and P2 as starting points for the reasons set forth above.

(2) Thermal Denaturation, Re-association, and DNA Synthesis Reaction (2)

In the second cycle of thermal denaturation, re-association, and DNA synthesis reaction, the annealing following thermal denaturation causes a double strand to form between nucleic acid elongation products (3) and (4). The subsequent DNA synthesis reaction, with each strand serving as a template for the other, causes the nucleic acid to elongate from the 3' terminus of each, yielding a nucleic acid synthesis product in the form of a joined DNA fragment containing one joined unit in which sequence A-target gene-sequence B are sequentially connected.

(3) Thermal Denaturation, Re-association, and DNA Synthesis Reaction (Third and Subsequent Cycles)

Although not shown in the scheme of FIG. 6, three or more cycles of thermal denaturation, re-association, and DNA synthesis reaction can be implemented. By implementing three or more cycles of thermal denaturation, re-association, and DNA synthesis reaction, the joined DNA fragment containing one joined unit of sequentially connected sequence A-target gene-sequence B can be obtained as a nucleic acid synthesis product. In the second aspect of the present invention, since a sequence in which sequence B and sequence A are joined, such as VT2-VP2-sequence B-sequence A-VP1-VP2, is not employed as a double-stranded joining DNA fragment in the manner of the first aspect of the present invention, no joined unit polymer containing multiple joined units connected in the sequence of sequence A-target gene-sequence B is synthesized.

<The Joined Unit Comprised of Sequence A-target Gene-sequence B>

In the second aspect of the present invention, in the same manner as in the first aspect of the present invention, it is desirable to provide a step of preparing a joined unit comprised of sequence A-target gene-sequence B from the joined DNA fragment obtained as a nucleic acid synthesis product. The step of preparing a joined unit is not specifically limited. By way of example, it can be implemented as a method employing a restriction enzyme to specifically recognize sites upstream and downstream of sequence A and sequence B, or a method of selectively amplifying the joined unit.

When the joined unit that has been separated by the above method from the joined DNA fragment is introduced into a host cell as an expression unit and the host cell is caused to selectively express the protein that is coded for by the target gene, a promoter sequence can be employed in sequence A and a polyadenylation signal can be employed in sequence B. When preparing an expression unit, to the extent that expression of the target gene is not impeded in the host cell, sequences such as spacer sequences can be present between the various sequences, upstream of sequence A, and downstream of sequence B.

[The Third Aspect of the Present Invention]

The third aspect of the present invention is a method employing one of two double-stranded joining DNA fragments obtained by division in two in the second aspect of the present invention as set forth above, and a sequence schematically denoted as region 1-joining DNA region 1 or joining DNA region 2-region 2. In this method, the nonspecific production of a single-sided joined DNA fragment in which joining DNA region 1 or 2 is joined on one side of a non-target gene is inhibited, making it possible to specifically obtain a targeted single-sided joined DNA fragment in which joining DNA region 1 or 2 is joined to one side of the target gene. The "3' end protruding double-stranded gene fragment" employed in the third aspect of the present invention can have a protruding terminus and an associative region on both terminus sides of a target sequence in the same manner as in the first aspect of the present invention. It can also be a 3' end protruding double-stranded gene fragment in which the associative region is present on just one terminus side of the target gene sequence, at least a portion of this region is an inherent base sequence that is contained in the target gene sequence, and a protruding terminus of one or more nucleotides is present on the 3' end of the associative region. Since a protruding terminus and associative region are employed on just one terminus side of the 3' end protruding double-stranded gene fragment in the third aspect of the present invention, the latter 3' end protruding double-stranded gene fragment is desirably employed.

The double-stranded joining DNA fragments employed in the third aspect of the present invention are two fragments having a sequence schematically denoted as region 1-joining DNA region 1 and a sequence schematically denoted as joining DNA region 2-region 2. The sequence that is schematically denoted as region 1-joining DNA region 1 will be described in an embodiment in the form of sequence A-VP1-VT1. An embodiment in which the sequence denoted by joining DNA region 2-region 2 is VT2-VP2-sequence B can be implemented in the same manner as the embodiment in which the sequence schematically denoted by region 1-joining DNA region 1 is sequence A-VP1-VT1.

The embodiment of the third aspect of the present invention provides a method of selectively joining a double-stranded joining DNA fragment comprising sequence A (sequence A-VP1-VT1) to one of the terminus sides of a target gene fragment. In this method, the above 3' end protruding double-stranded gene fragment (where the 3' protruding terminus can be the 3' terminus side of sequence P1 of one of the strands) and a DNA fragment comprising sequence A are employed. A mixture of 3' end protruding double-stranded gene fragments and double-stranded joining DNA fragments comprising sequence A is thermally denatured, re-associated, and subjected to a nucleic acid synthesis reaction. These operations yield a hetero double-stranded DNA product comprised of two associated strands, one of which is single-stranded DNA (the antisense strand of the double-stranded DNA fragment) having a sequence of one or more nucleotides as a protruding terminus on the 3' end of sequence P1 of one strand and having a sequence derived from sequence P2 on the 5' end thereof, and single-stranded DNA (the sense strand of the double-stranded joining DNA) having a sequence derived from sequence A on the 5' end side of the other strand and a sequence derived from sequence VT1 on the 3' end thereof. Next, this hetero double-stranded DNA product is employed as template to conduct a polymerase chain reaction with a reverse primer having the 5'-terminus side sequence of the antisense strand of the double-stranded gene fragment and a forward primer having the 5'-terminus side sense strand of the double-stranded joining DNA fragment. That yields a double-stranded DNA fragment (single-sided joined DNA fragment) in which sequence A and the target gene sequence are joined (see the scheme of FIG. 7).

The thermal denaturation, re-association, and DNA synthesis reaction are identical to those described in the embodiment of the first aspect of the present invention set forth above. Sequence A-VP1-VT1 is identical to that described in the embodiment of the second aspect of the present invention set forth above.

The embodiment in which the sequence denoted by joining DNA region 2-region 2 is VT2-VP2-sequence B can be implemented in the same manner as the embodiment in which the sequence schematically denoted as region 1-joining DNA region 1 is sequence A-VP1-VT1. VT2-VP2-sequence B is identical to that described in the embodiment of the second aspect of the present invention set forth above.

In the method for producing a joined DNA fragment of the present invention, as set forth above, the target gene can be an antibody gene or a T cell receptor gene, the 3' end protruding double-stranded gene fragment can contain a sequence derived from the antibody or T cell receptor gene, and the region VP1 and region VT1 in the double-stranded joining DNA fragment or double-stranded joining DNA fragment comprising sequence A can comprise sequences that are, or are not, derived from an antibody gene or a T cell receptor gene. Further, the target gene can be an antibody gene or a T cell receptor gene, the 3' end protruding double-stranded gene fragment can contain a sequence derived from the antibody gene or T cell receptor gene, and region VP2 and region VT2 in the double-stranded joining DNA fragment or the double-stranded joining DNA fragment comprising sequence B can be sequences that are, or are not, derived from an antibody gene or a T cell receptor gene. The present invention includes a method for producing an antibody or a T cell receptor using a joined DNA fragment produced using such a target gene.

The method for producing an antibody or a T cell receptor using a joined DNA fragment in which the target gene is an antibody gene or a T cell receptor gene can be implemented by the usual methods. For example, a joined DNA fragment containing the target gene can be introduced into a host cell, and the host cell can be cultured and caused to produce the antibody or the like.

The present invention as set forth above includes the 3' end protruding double-stranded gene fragment, double-stranded joining DNA fragment, and assembly thereof that are employed in the first through third aspects of the present invention, as well as a kit comprising the same. The 3' end protruding double-stranded gene fragment and double-stranded joining DNA fragment employed in the first through third aspects of the present invention are as set forth above. Further, the assembly comprises an assembly of the 3' end protruding double-stranded gene fragment and the double-stranded joining DNA fragment employed in the first aspect, an assembly of the 3' end protruding double-stranded gene fragment and the double-stranded joining DNA fragment employed in the second aspect, and an assembly of the 3' end protruding double-stranded gene fragment and the double-stranded joining DNA fragment employed in the third aspect.

From the perspective of producing well a joined DNA fragment in which the joining DNA fragment is joined to both sides of the target gene in the assembly of the 3' end protruding double-stranded gene fragment and double-stranded joining DNA fragment employed in the first aspect, it is desirable for:

(3-1) one of the associative regions of the 3' end protruding double-stranded gene fragment to be comprised of a base sequence that is homologous with the associative region of one terminus of the double-stranded joining DNA fragment, with the sequence on the terminus to which the 3' protruding end has been added being the side that connects to the joining DNA region in one of the associative regions of the double-stranded joining DNA fragment;

(3-2) the terminus protruding from one of the associative regions of the 3' end protruding double-stranded gene fragment to not have a strand-elongating function in a DNA synthesis reaction;

(3-3) for the other associative region of the 3' end protruding double-stranded gene fragment to be comprised of a base sequence that is homologous with the associative region of the other terminus of the double stranded joining DNA fragment, with the sequence on the terminus to which the 3' protruding end has been added to be the side that connects to the joining DNA region in the other associative region of the double-stranded joining DNA fragment; and (3-4) for the terminus protruding from the other associative region of the 3' end protruding double-stranded gene fragment to not have a strand-elongating function in the DNA synthesis reaction.

From the perspective of producing well a joined DNA fragment in which joining DNA region 1 is properly joined to one side of the target gene and joining DNA region 2 is properly joined to the other side thereof in the assembly of the 3' end protruding double-stranded gene fragment and the double-stranded joining DNA fragments employed in the second aspect, it is desirable for:

(3-1) one of the associative regions of the 3' end protruding double-stranded gene fragment to be comprised of a base sequence that is homologous with the associative region of double-stranded joining DNA fragment 1, with the sequence on the terminus to which the 3' protruding end has been added being the side that connects to the joining DNA region in the associative region of double-stranded joining DNA fragment 1;

(3-2) the terminus protruding from the one associative region of the 3' end protruding double-stranded gene fragment to not have a strand-elongating function in a DNA synthesis reaction;

(3-3) the other associative region of the 3' end protruding double-stranded gene fragment to be comprised of a base sequence that is homologous with the associative region of the other terminus of double stranded joining DNA fragment 2, with the sequence on the terminus to which the 3' protruding end has been added being the side that connects to the joining DNA region in the associative region of double-stranded joining DNA fragment 2; and (3-4) the terminus protruding from the other associative region of the 3' end protruding double-stranded gene fragment to not have a strand-elongating function in the DNA synthesis reaction.

From the perspective of producing well a single-sided joined DNA fragment in which the joining DNA fragment is joined to one side of the target gene in the assembly of the 3' end protruding double-stranded gene fragment and double-stranded joining DNA fragment employed in the third aspect, it is desirable for:

(3-1) one of the associative regions of the 3' end protruding double-stranded gene fragments to be comprised of a base sequence that is homologous with the associative region of the double-stranded joining DNA fragment, but with the sequence on the side of the terminus on which the 3' protruding end has been added being the side that connects with the joining DNA region in the associative region of the double-stranded joining DNA fragment; and (3-2) the terminus protruding from one of the associative regions of the 3' end protruding double-stranded gene fragment to not have a strand-elongating function in a DNA synthesis reaction.

The kit of the present invention is comprised of the 3' end protruding double-stranded gene fragment and double-stranded joining DNA fragment employed in the first aspect of the present invention, or an assembly thereof; the 3' end protruding double-stranded gene fragment and double-stranded joining DNA fragments employed in the second aspect of the present invention, or an assembly thereof; or the 3' end protruding double-stranded gene fragment and double-stranded joining DNA fragment employed in the third aspect of the present invention, or an assembly thereof. In addition to the above, the kit of the present invention can also contain the buffer solution, DNA polym erase, and other DNA synthesis enzymes or enzyme-containing buffer solutions that are employed to obtain a joined DNA fragment by conducting thermal denaturation, re-association, and a DNA synthesis reaction using the 3' end protruding double-stranded gene fragment and double-stranded joining DNA fragment, as well as a kit instruction manual.

The present invention will be described in greater detail below through embodiments. However, the present invention is not limited to the embodiments.

[Embodiments]

EXAMPLE 1

1. The specific transfer of an unpurified target gene fragment into an expression unit Target gene fragment 1 (see FIG. 10) was a 683 bp DNA fragment comprising a variable region and part of a constant region of the human immunoglobulin γ-chain. At its two ends, it comprised the sequences of primer A: 5'-CTTCGAATTCT-GCAGTCGACGGTACCGCGGGCCCGGGA-3' and primer B: 5'-AGCCGGGAAGGTGTGCACGCCGCTG-3'. The poly(dC) sequence was present within primer A and an immunoglobulin γ-chain constant region-derived sequence was present within primer B as internal sequences. The positions of primers A and B used in amplification are indicated by arrows in FIG. 10.

Non-target gene fragment 2 (see FIG. 11) is a 628 bp DNA fragment derived from GPF and the sequences of primer A and primer B, used for PCR amplification, were present on the two ends thereof. No internal sequence is present within the both primers but the sequence derived from GPF gene.

PCR was conducted with primers A and B using plasmid pUC119 inserted with target gene fragment 1 and non-target gene fragment 2 as template to amplify target gene fragment 1 and non-target gene fragment 2, respectively. The PCR was conducted as 30 cycles of reactions at 94° C., 30 s and 68° C., 40 s using Takara Bio PrimeSTAR thermo-resistant DNA polymerase, adding 2 ng of template plasmid DNA, 10 μmol of each primer, and 10 nmol of dNTP, in a 50 μL reaction system.

2. Pcr product 3' end nucleotide addition reaction

Following PCR, the reaction solution was separately poured into 1 μL tubes. To these were added 10 units of terminal deoxynucleotidyl transferase, and the mixture was reacted for 30 minutes at 37° C. Subsequently, heating was conducted for 5 minutes at 94° C. to stop the enzyme reaction. This reaction added polynucleotide to the two 3' ends of the DNA fragment. As a negative control, reactions were conducted with target gene fragment 1 and non-target gene fragment 2, respectively, without adding terminal deoxynucleotidyl transferase.

3. Preparing a human γ-chain gene joining double-stranded dna fragment pMiniCMV-hIgG is a plasmid with a total length of 3,533 bp comprising CMV promoter, multicloning sites, a poly(dC/dG) sequence, a pUC119 replication starting point, an ampicillin resistance gene, a human immunoglobulin γ-chain constant region, and an SV40 polyadenylation signal.

The pMiniCMV-hIgG was cleaved with EcoRV and the product was used as a template to conduct PCR with primer C 5'-GGGGGGGGGGGGGGGGGGGATCCCGG-3' and primer D 5'-CGTGGAACTCAGGCGCCCTGACCAG-3' to prepare a human γ-chain gene joining double-stranded DNA fragment. The PCR amplification reaction was conducted as 30 cycles of 94° C., 40s; 60° C., 40 s; 72° C., 5 min. using PrimeSTAR DNA polymerase from Takara Bio. The amplified DNA fragments were purified by the spin column method and adjusted to a concentration of 10 ng/μL. On one end of the human γ-chain gene joining double-stranded DNA fragment had just the human immunoglobulin γ-chain amplified by the 5'-RACE PCR method and a region for forming a specific complementary strand in the form of an internal sequence derived from a human immunoglobulin γ-chain constant region, and downstream from it, a sequence forming a complementary strand with the primer B sequence employed in gene amplification (see FIG. 12).

Figure 13:
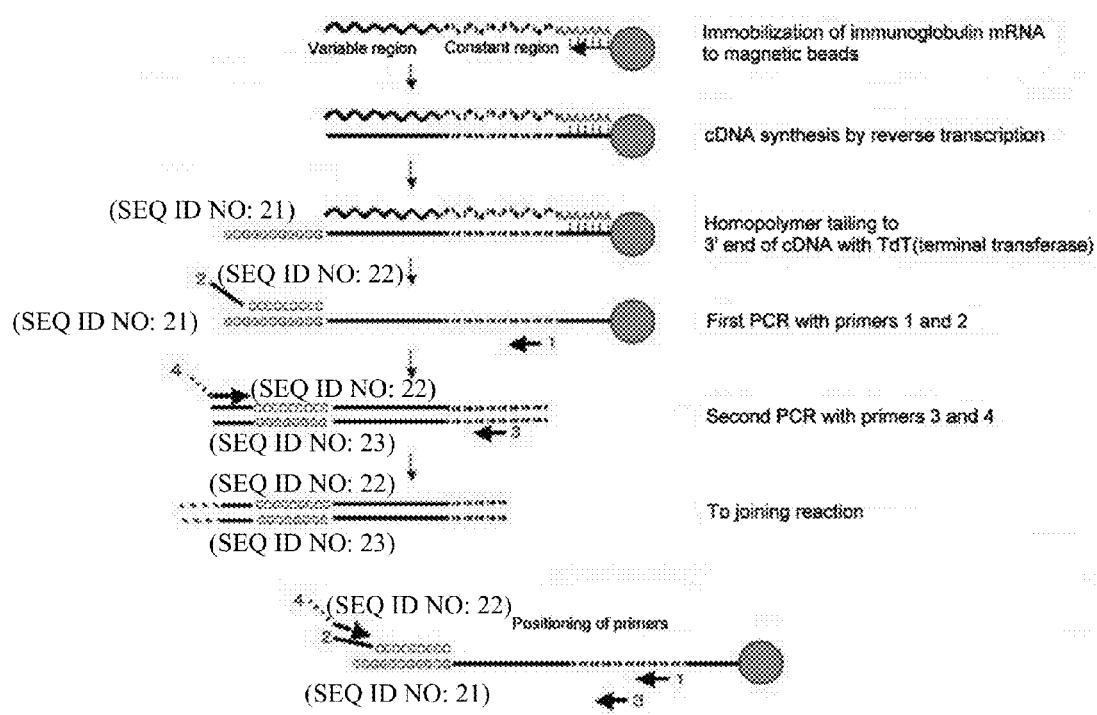
FIG. 13 is a descriptive drawing of the cDNA synthesis (immunoglobulin variable region amplification method) using magnetic beads.
Figure 14:
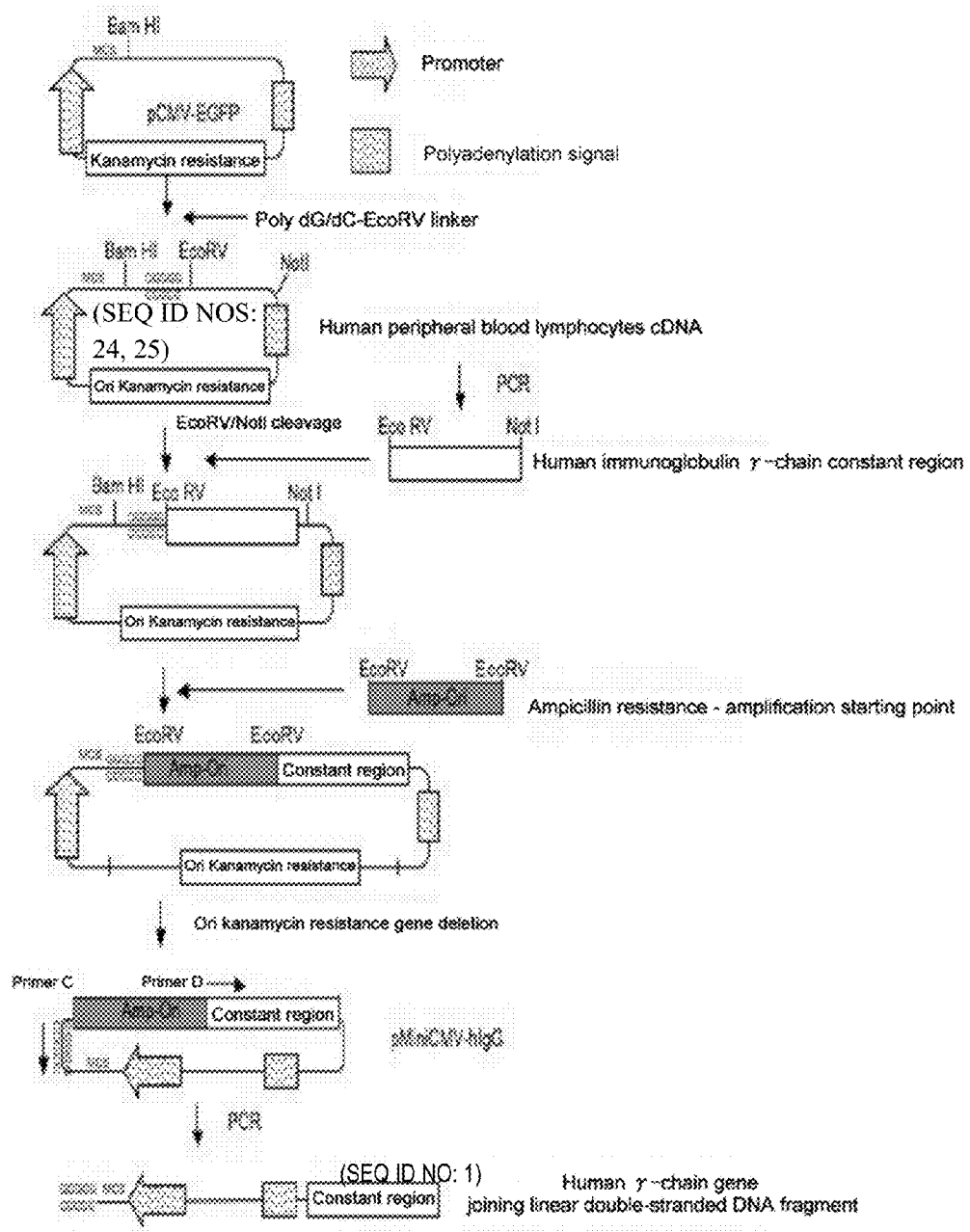
FIG. 14 is a typical drawing of a method of preparing a human γ-chain gene double-stranded joining DNA fragment.

On the other end thereof was present just the 5'-RACE amplification product derived from cDNA to which a poly(dC) sequence had been added by reaction with terminal deoxynucleotidyl transferase and a region for specifically forming a complementary strand in the form of a poly(dC/dG) sequence, and upstream from it, a sequence for forming a strand complementary with the primer A sequence employed in the 5'-RACE PCR method (see FIG. 13). Although a complementary strand consisting of the entire hatched portion in FIG. 12 could be formed with target gene fragment 1, only a complementary strand consisting of the sequences forming complementary strands with primer B and primer A in the hatched portion in FIG. 12 could be formed with non-target gene fragment 2.

4. Amplification of the human γ-chain gene expression unit

To 3' end polynucleotide-added DNA fragments 1 and 2 prepared above were added 10 ng of human γ-chain gene joining double-stranded DNA fragment, 10 μmol of primer, and 10 nmol of dNTP. Five cycles of 94° C., 40 s and 70° C., 4 minute reactions followed by 30 cycles of 94° C., 40 s; 60° C., 40 s; 72° C., 4 min. reactions were conducted in 25 μL of a reaction solution containing PrimeSTAR thermo-resistant DNA polymerase made by Takara Bio. Among the primers employed, primer E: 5'-AGAGAAGATCTTAG TTATTAAT-AGTAATCAATTACGG-3' had a mismatch sequence on the 5' end thereof and annealed in the upstream vicinity of the CMV promoter of the human γ-chain gene joining double-stranded DNA fragment. Primer F: 5'-AAGGAAGATCTG-GACAAACCACAA-CTAGAATGCAGTG-3' had a mismatch sequence on the 5' end thereof and annealed in the downstream vicinity of the SV40 polyadenylation signal of the human γ-chain gene joining double-stranded DNA fragment.

Similarly, to target gene fragment 1 and non-target gene fragment 2—prepared as negative controls by not adding 3' end polynucleotide—were added 10 ng of human γ-chain gene joining double-stranded DNA fragment, 10 μmol of primers E and F, and 10 nmol of dNTP. Five cycles of 94° C., 40 s and 70° C., 4 minute reactions followed by 30 cycles of 94° C., 40 s; 60° C., 40 s; 72° C., 4 min. reactions were conducted in 25 μL of a reaction solution containing PrimeSTAR thermo-resistant DNA polymerase made by Takara Bio. A 2 μL quantity was collected from each of the PCR reaction solutions and the amplification of expression units was confirmed by agarose gel electrophoresis (see FIG. 1).

As a result, 3' end polynucleotide-added target gene fragment 1 was specifically transferred to an expression unit and the amplification of a PCR product of about 2.5 kb was confirmed. By contrast, 3' end polynucleotide-added non-target gene fragment 2 was not transferred to an expression unit. Further, in target gene fragment 1 that had not been subjected to a 3' end polynucleotide addition reaction, there was a transfer to an expression unit, but non-target gene fragment 2 was also joined to human γ-chain gene joining double-stranded DNA fragment. These results revealed that the use of a gene joining double-stranded DNA fragment having an internal sequence from the target gene fragment and a gene fragment that had been subjected to a 3' end polynucleotide addition reaction permitted the transfer to an expression unit without purifying the DNA fragment containing a portion of the constant region and the variable region of human immunoglobulin being targeted.

EXAMPLE 2

Amplification of an efficient joined unit (expression unit) employing 5' end mismatch primer A joined double-stranded DNA polymer was synthesized by adding the human γ-chain gene joining DNA fragment prepared in 3 to the 3' end polynucleotide-added target gene DNA fragment 1 prepared in 2 of Example 1 and conducting five cycles of 94° C., 40 s; 70° C., 4 min. reactions. To this were added primers E and F, or primers G and H, and 30 cycles of 94° C., 40 s; 60° C., 40 s, and 72° C., 4 min. reactions were conducted in an attempt to amplify the expression unit. Primer G: 5'-TAGTTATTAATAGTAATCAATTACGG-3' and primer H: 5'-TGGACAAACCACAACTAGAATG-CAGTG-3' had 100% homology with the human γ-chain gene double-stranded joining DNA fragment employed as template.

Figure 2:
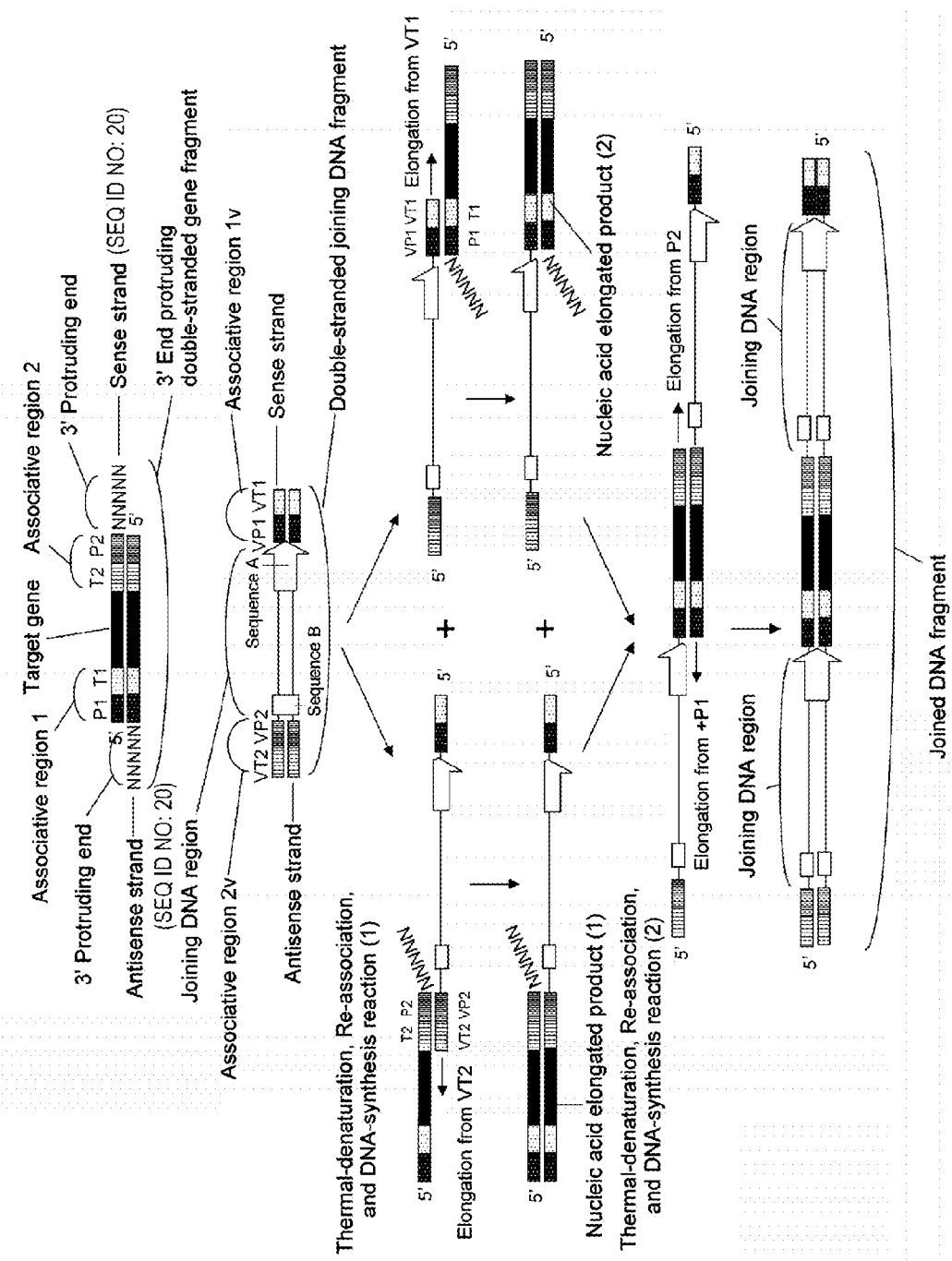
FIG. 2 is a reaction scheme describing an embodiment of carrying out the first aspect of the present invention.

When primers G and H were employed in PCR, in addition to amplification of the targeted expression unit, amplification of joined unit polymer was observed (see FIG. 2). By contrast, when primers E and F were employed, which had mismatch sequences on the 5' ends thereof, efficient expression unit amplification was observed.

EXAMPLE 3

Unpurified human γ and κ-chain immunoglobulin gene fragments amplified from human peripheral blood plasma cells and human γ and κ-chain gene joining DNA fragments were employed to prepare human immunoglobulin expression units. These were introduced into cultured cells to prepare human antibodies.

Amplification of Human Immunoglobulin γ and κ-Chain Variable Region Gene Fragments by 1.5'-RACE PCR A single plasma cell prepared from human peripheral blood was isolated in each of two tubes. To each was added 3 μL of cell lysate containing 3 μg of magnetic beads (Dynabeads) to which was connected oligo(dT25) (100 mM Tris HCl (pH 7.5), 500 mM LiCl, 1% dodecyl sulfuric acid Li (LiDS), and 5 mM dithiothreitol), and the mRNA in the cells was bound to the magnetic beads. Next, the beads were washed once in 3 μL mRNA cleaning solution A (10 mM TrisHCl (pH 7.5), 0.15 M LiCl, 0.1% LiDS) followed by 3 μL of mRNA cleaning solution B (75 mM KCl, 3 mM MgCl2, 0.1% TritonX, 0.5 mM dNTP, 5 mM DTT, 2 units of RNase inhibitor), after which cDNA synthesis was conducted. To the magnetic beads that had been cleaned were added 3 μL of cDNA synthesis solution (50 mM TrisHCl (pH 8.3), 75 mM KCl, 3 mM MgCl2, 0.1% TritonX-100, 0.5 mM dNTP, 5 mM DTT, 2 units of RNase inhibitor, 10 units of SuperScript III Reverse transcriptase (Invitrogen)) and the mixture was reacted for one hour at 50° C. Next, magnetic beads were washed with 3 μL of 3' tailing cleaning solution (50 mM potassium phosphate (pH 7.0), 0.5 mM dGTP, 0.1% TritonX-100, 4 mM magnesium chloride), another 3 μL of 3' tailing reaction solution (50 mM potassium phosphate (pH 7.0), 0.5 mM dGTP, 0.1% TritonX-100, 4 mM magnesium chloride, and 10 U of terminal deoxynucleotidyl transferase) was added, and the mixture was reacted for 30 minutes at 37° C.

Magnetic beads were washed in 3 μL of TE solution (10 mM TrisHCl (pH 7.5), 1 mM EDTA, 0.1% TritonX-100) and human immunoglobulin γ-chain and κ-chain genes were amplified by 5'-RACE PCR. In the first cycle of PCR, 25 μL of PCR solution (containing 10 μmol of each of primers I, J, and K, 10 nmol of dNTP, and 1 U of Takara Bio PrimeSTAR thermo-resistant DNA polymerase) was added to the magnetic beads and 35 cycles of 94° C., 30 s; 68° C., 40 s reactions were conducted. The sequence of primer I was 5'-CGGTAC-CGCGGGC-CCGGGATCCCCCCCCCCCCCDN-3'.
Annealing was conducted with poly(G) that had been added to the 3' end of cDNA by TdT. The sequence of primer J was 5'-ACGCTGCTGAGGGAGTAGAGTCCTGAG-3'. It was derived from the constant region of the human immunoglobulin γ-chain gene. The sequence of primer K was 5'-CTTTG-GCCTCTCTGGGATAGAAGTT-3'. It was derived from the constant region of the human immunoglobulin κ-chain gene.

Following the reaction, 225 μL of water was added to the PCR solution, 1 μL of the 10-fold diluted solution was employed as template, and an amplification reaction of the variable region of the human immunoglobulin γ-chain gene was conducted with primer A and primer B under the same conditions as the first cycle of PCR. Similarly, using primer A and primer L, 5'-ACAACAGAGGCAGTTCCA-GATTTCAACTGC-3', an amplification reaction of the variable region of the human immunoglobulin κ-chain gene was conducted.

Figure 15:
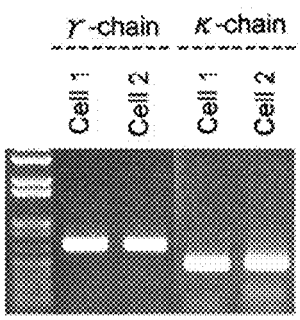
FIG. 15 is a drawing showing the results of amplification of γ-chain and κ-chain variable regions by human plasma cells 1 and 2 in Example 3.

As a result, amplification of the variable region and part of the constant region of the γ-chain of about 800 bp and amplification of the variable region and part of the constant region of about 600 bp from the two plasma cells (cell 1 and cell 2) employed in the experiment were observed (see FIG. 15).

2. The PCR Product 3' End Polynucleotide Addition Reaction

1. To 1 µL of each of the PCR products prepared in 1. were added 10 units of terminal deoxynucleotidal transferase, the mixtures were reacted for 30 minutes at 37° C., and heating was conducted for 5 minutes at 94° C. to stop the enzymatic reaction.

Figure 16:
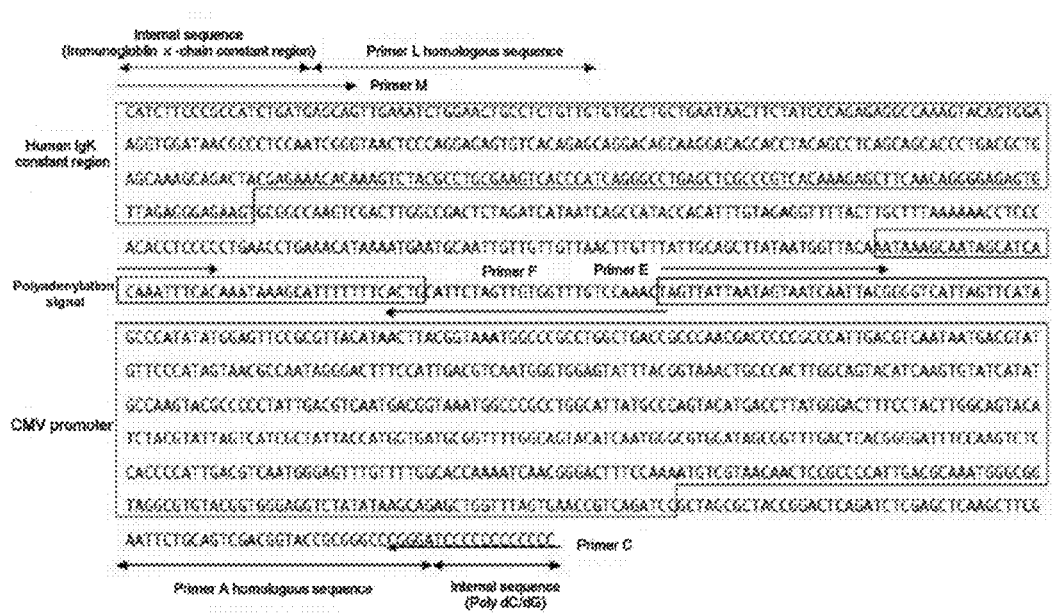
FIG. 16 is a descriptive drawing of the base sequence of a human κ-chain gene double-stranded joining DNA fragment.

3. Preparation of Human γ-Chain Gene and κ-Chain Gene Joining Double-Stranded DNA Fragments The human γ-chain gene joining double-stranded DNA fragment prepared in Example 1 was employed.

pMiniCMV-hIgK is a plasmid 2,976 bp in total length having a CMV promoter, a multicloning site, a poly(dC/dG) sequence, a pUC119 replication starting point, an ampicillin resistance gene, a human immunoglobulin κ-chain constant region, and an SV40 polyadenylation signal.

pMiniCMV-hIgK was cleaved with EcoRV and employed as template to prepare a human κ-chain gene joining DNA fragment (see FIG. 16) by PCR employing primer C and primer M: 5'-CATCTTCCCGCCATCTGATGAGCAG-3'. The PCR consisted of 30 cycles of 94° C., 40 s; 60° C., 40 s; 72° C. 5 min. amplification reactions employing PrimeSTAR DNA polymerase from Takara Bio. The amplified DNA fragment was purified by the spin column method and adjusted to a concentration of 10 ng/µL.

4. Amplification of Human γ-Chain and κ-Chain Expression Units

To the above-prepared 3' end polynucleotide-added human γ-chain gene solution were added 10 ng of the human γ-chain gene joining double-stranded DNA fragment prepared in 3., 10 µmol of primer, and 10 nmol dNTP. In a 25 µL reaction solution employing PrimeSTAR thermo resistant DNA polymerase from Takara Bio, five cycles of 94° C., 40 s; 70° C., 4 min. reactions followed by 30 cycles of 94° C., 40 s; 60° C., 40 s, and 72° C., 4 min. reactions were conducted. Employed primers were primer E and primer F.

Similarly, to the above-prepared 3' end polynucleotide-added human κ-chain gene solution were added 10 ng of the human κ-chain gene joining double-stranded DNA fragment prepared in 3., 10 µmol of primer, and 10 nmol dNTP. In a 25 µL reaction solution employing PrimeSTAR thermo resistant DNA polymerase from Takara Bio, five cycles of 94° C., 40 s; 70° C., 4 min. reactions followed by 30 cycles of 94° C., 40 s; 60° C., 40 s, and 72° C., 4 min. reactions were conducted. Employed primers were primer E and primer F.

Figure 17:
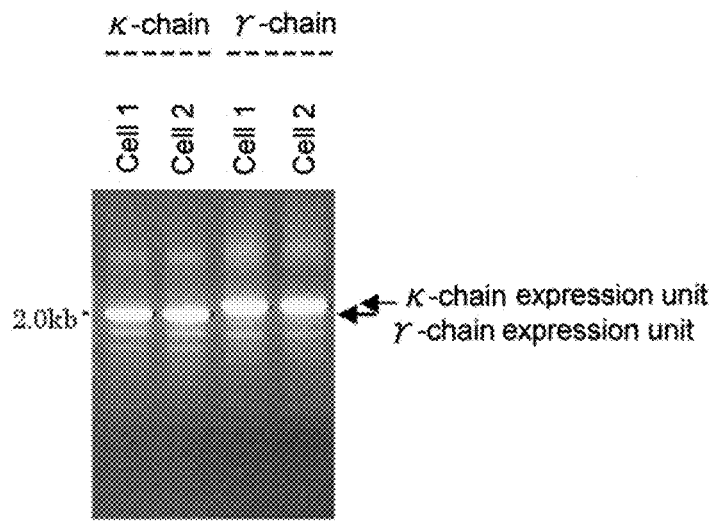
FIG. 17 is a drawing showing the results of changing amplified γ-chain and κ-chain variable regions to expression units in Example 3.

The DNA fragment that had been amplified was purified by precipitation in ethanol and dissolved in 25 µL of PBS. A 1 µL quantity of each DNA fragment obtained was collected and agarose gel electrophoresis was used to confirm the transfer to expression units of the K and γ-chain immunoglobulin gene fragments obtained from cell 1 and cell 2 (see FIG. 17).

Figure 18:
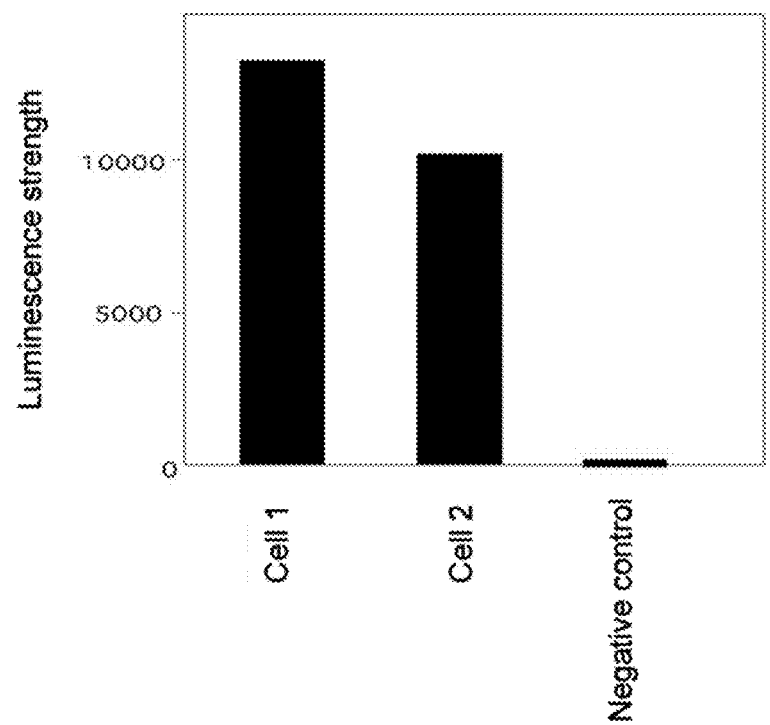
FIG. 18 is a drawing showing the results of measurement of recombinant human immunoglobulin secreted into a cell culture by the ELAISA method in Example 3.

5. Expression of Anti-GFP Antibody by Introduction of Human Immunoglobulin Expression Units into Cultured Cells To a 5 µL quantity (about 0.25 µg) of each of the human κ and γ-chain expression units prepared in 4. were added 90 µL of DMEM medium and 2 µL of FuGENE HD transfection reagent. The mixtures were left standing for 20 minutes at room temperature, after which the genes were transfected into 293FT cells that had been cultured in a 24-well culture dish. The cells were cultured for three days, after which the medium supernatant was recovered and the production of human antibodies was measured by the sandwich ELISA method (see FIG. 18). ELISA was conducted by immobilizing 1 µg of ovine anti-human antibody on the bottom surface of a 96-well plate, adding 100 µL of cell supernatant, and conducting an antigen-antibody reaction for 3 hours. The recombinant human antibody that bound to the plate was detected using ovine anti-human antibody bound to horseradish peroxidase. As a result, recombinant human antibody was detected in the culture supernatant of 293FT cells that had been transfected with human γ and human κ-chain gene expression units derived from cell 1 (column 1) and the human γ and human κ-chain gene expression units derived from cell 2 (column 2). No recombinant human antibody was detected in the supernatant of the cells into which no gene had been introduced as a negative control (column 3).

The relation between the various DNA fragments employed in the embodiments and SEQ. ID NO: 1 in the SEQUENCE LISTING is as follows.

```
SEQUENCE LISTING SEQ. ID NO: 1:
Target gene fragment 1
CTTCGAATTCTGCAGTCGACGGTACCGCGGGCCCGGGATCCCCCCCCCC

CGACATAACAACCAGAATCCTCCTCTAAAGAAGCACCTGGGAGCACAGCTC

ATCACCATGGACTGGACCTGGAGGTTCCTCTTTGTGGTGGCAGCAGCTACA

GGTGTCCAGTCCCAGGTCCAGCTGGTGCAATCTGGGGCTGAGGTGAAGAA

GCCTGGGTCCTCGGTGAAGATCTCCTGCAAGGCTTCTGGAGGCACCTTCAG

CAGCTATACTTTCACCTGGGTGCGACAGGCCCCTGGACAAGGGCTTGAGTG

GATGGGAAGGATCATCCCCAATGTCGGTATAGCAAACTACGCACAGAAGTT

CCAGGGCAGAGTCACGCTTATCGCGGACAAATTCACGAATTCAACGTACAT

GGAGCTGAGCAGCCTGAGATCTGATGACACGGCCGTTTATTTTTGTGCCGG

AGACCCCTCGGGCCACTCACATGACTACTGGGGCCAAGGAACCCTGGTCA

CCGTCTCCTCAGCTTCCACCAAGGGCCCATCCGTCTTCCCCCTGGCGCCCT

GCTCCAGGAGCACCTCCGAGAGCACAGCCGCCCTGGGCTGCCTGGTCAAG

GACTACTTCCCCGAACCGGTGACGGTGTCGTGGAACTCAGGCGCCCTGAC

CAGCGGCGTGCACACCTTCCCGGCT

SEQUENCE LISTING SEQ. ID NO: 2:
Primer A

SEQUENCE LISTING SEQ. ID NO: 3:
Primer B

SEQUENCE LISTING SEQ. ID NO: 4:
Non-target gene fragment 2
CTTCGAATTCTGCAGTCGACGGTACCGCGGGCCCGGGATCCACCGGTCGC

CACCATGGTGAGCAAGGGCGAGGAGCTGTTCACCGGGGTGGTGCCCATCC

TGGTCGAGCTGGACGGCGACGTAAACGGCCACAAGTTCAGCGTGTCCGGC

GAGGGCGAGGGCGATGCCACCTACGGCAAGCTGACCCTGAAGTTCATCTG

CACCACCGGCAAGCTGCCCGTGCCCTGGCCCACCCTCGTGACCACCCTGA

CCTACGGCGTGCAGTGCTTCAGCCGCTACCCCGACCACATGAAGCAGCAC

GACTTCTTCAAGTCCGCCATGCCCGAAGGCTACGTCCAGGAGCGCACCATC

TTCTTCAAGGACGACGGCAACTACAAGACCCGCGCCGAGGTGAAGTTCGAG

GGCGACACCCTGGTGAACCGCATCGAGCTGAAGGGCATCGACTTCAAGGA

GGACGGCAACATCCTGGGGCACAAGCTGGAGTACAACTACAACAGCCACAA
```

-continued
CGTCTATATCATGGCCGACAAGCAGAAGAACGGCATCAAGGTGAACTTCAA

GATCCGCCACAACATCGAGGACGGCAGCGTGCAGCTCGCCGACCACTACC

AGCGGCGTGCACACCTTCCCGGCT

SEQUENCE LISTING SEQ. ID NO: 5:
pMiniCMV-hIgG
TAGTTATTAATAGTAATCAATTACGGGGTCATTAGTTCATAGCCCATATA

TGGAGTTCCGCGTTACATAACTTACGGTAAATGGCCCGCCTGGCTGACCG

CCCAACGACCCCCGCCCATTGACGTCAATAATGACGTATGTTCCCATAGT

AACGCCAATAGGGACTTTCCATTGACGTCAATGGGTGGAGTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTGATGCGGTTTTGGCAGTACATCAATGGGCGTGGA

TAGCGGTTTGACTCACGGGGATTTCCAAGTCTCCACCCCATTGACGTCAA

TGGGAGTTTGTTTTGGCACCAAAATCAACGGGACTTTCCAAAATGTCGTA

ACAACTCCGCCCCATTGACGCAAATGGGCGGTAGGCGTGTACGGTGGGAG

GTCTATATAAGCAGAGCTGGTTTAGTGAACCGTCAGATCCGCTAGCGCTA

CCCGGACTCAGATCTCGAGCTCAAGCTTCGAATTCTGCAGTCGACGGTACC

GCGGGCCCGGGATCCCCCCCCCCCCGATATCTAAATACATTCAAATATG

TATCCGCTCATGAGACAATAACCCTGATAAATGCTTCAATAATATTGAAA

AAGGAAGAGTATGAGTATTCAACATTTCCGTGTCGCCCTTATTCCCTTTT

TTGCGGCATTTTGCCTTCCTGTTTTTGCTCACCCAGAAACGCTGGTGAAA

GTAAAAGATGCTGAAGATCAGTTGGGTGCACGAGTGGGTTACATCGAACT

GGATCTCAACAGCGGTAAGATCCTTGAGAGTTTTCGCCCCGAAGAACGTT

TTCCAATGATGAGCACTTTTAAAGTTCTGCTATGTGGCGCGGTATTATCC

CGTATTGACGCCGGGCAAGAGCAACTCGGTCGCCGCATACACTATTCTCA

GAATGACTTGGTTGAGTACTCACCAGTCACAGAAAAGCATCTTACGGATG

GCATGACAGTAAGAGAATTATGCAGTGCTGCCATAACCATGAGTGATAAC

ACTGCGGCCAACTTACTTCTGACAACGATCGGAGGACCGAAGGAGCTAAC

CGCTTTTTTGCACAACATGGGGGATCATGTAACTCGCCTTGATCGTTGGG

AACCGGAGCTGAATGAAGCCATACCAAACGACGAGCGTGACACCACGATG

CCTGTAGCAATGGCAACAACGTTGCGCAAACTATTAACTGGCGAACTACT

TACTCTAGCTTCCCGGCAACAATTAATAGACTGGATGGAGGCGGATAAAG

TTGCAGGACCACTTCTGCGCTCGGCCCTTCCGGCTGGCTGGTTTATTGCT

GATAAATCTGGAGCCGGTGAGCGTGGGTCTCGCGGTATCATTGCAGCACT

GGGGCCAGATGGTAAGCCCTCCCGTATCGTAGTTATCTACACGACGGGGA

GTCAGGCAACTATGGATGAACGAAATAGACAGATCGCTGAGATAGGTGCC

TCACTGATTAAGCATTGGTAACTGTCAGACCAAGTTTACTCATATATACT

TTAGATTGATTTAAAACTTCATTTTTAATTTAAAAGGATCTAGGTGAAGA

TCCTTTTTGATAATCTCATGACCAAAATCCCTTAACGTGAGTTTTCGTTC

CACTGAGCGTCAGACCCCGTAGAAAAGATCAAAGGATCTTCTTGAGATCC

TTTTTTTCTGCGCGTAATCTGCTGCTTGCAAACAAAAAAACCACCGCTAC

CAGCGGTGGTTTGTTTGCCGGATCAAGAGCTACCAACTCTTTTTCCGAAG

GTAACTGGCTTCAGCAGAGCGCAGATACCAAATACTGTTCTTCTAGTGTA

GCCGTAGTTAGGCCACCACTTCAAGAACTCTGTAGCACCGCCTACATACC

TCGCTCTGCTAATCCTGTTACCAGTGGCTGCTGCCAGTGGCGATAAGTCG

TGTCTTACCGGGTTGGACTCAAGACGATAGTTACCGGATAAGGCGCAGCG

GTCGGGCTGAACGGGGGGTTCGTGCACACAGCCCAGCTTGGAGCGAACGA

CCTACACCGAACTGAGATACCTACAGCGTGAGCTATGAGAAAGCGCCACG

CTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTT

ATAGTCCTGTCGGGTTTCGCCACCTCTGACTTGAGCGTCGATTTTTGTGA

TGCTCGTCAGGGGGCGGAGCCTATGGAAAAACGCCAGCAACGCGGCCTT

TTTACGGTTCCTGGCCGATATCACGTGGAACTCAGGCGCCCTGACCAGCG

GCGTGCACACCTTCCCGGCTGTCCTACAGTCCTCAGGACTCTACTCCCTC

AGCAGCGTGGTGACCGTGCCCTCCAGCAGCTTGGGCACCCAGACCTACAC

CTGCAACGTGAATCACAAGCCCAGCAACACCAAGGTGGACAAGAGAGTTG

AGCCCAAATCTTGTGACAAAACTCACACATGCCCACCGTGCCCAGCACCT

GAACTCCTGGGGGGACCGTCAGTCTTCCTCTTCCCCCCAAAACCCAAGGA

CACCCTCATGATCTCCCGGACCCCTGAGGTCACATGCGTGGTGGTGGACG

TGAGCCACGAAGACCCTGAGGTCAAGTTCAACTGGTACGTGGACGGCGTG

GAGGTGCATAATGCCAAGACAAAGCCGCGGGAGGAGCAGTACAACAGCAC

GTACCGTGTGGTCAGCGTCCTCACCGTCCTGCACCAGGACTGGCTGAATG

GCAAGGAGTACAAGTGCAAGGTCTCCAACAAAGCCCTCCCAGCCCCCATC

GAGAAAACCATCTCCAAAGCCAAAGGGCAGCCCCGAGAACCACAGGTGTA

CACCCTGCCCCCATCCCGGGATGAGCTGACCAAGAACCAGGTCAGCCTGA

CCTGCCTGGTCAAAGGCTTCTATCCCAGCGACATCGCCGTGGAGTGGGAG

AGCAATGGGCAGCCGGAGAACAACTACAAGACCACGCCTCCCGTGCTGGA

CTCCGACGGCTCCTTCTTCCTCTACAGCAAGCTCACCGTGGACAAGAGCA

GGTGGCAGCAGGGGAACGTCTTCTCATGCTCCGTGATGCATGAGGGTCTG

CACAACCACTACACGCAGAAGAGCCTCTCCCTGTCTCCGGGTAAATGAGT

GCGACGGCGGCCGCGACTCTAGATCATAATCAGCCATACCACATTTGTAG

AGGTTTTACTTGCTTTAAAAAACCTCCCACACCTCCCCCTGAACCTGAAA

CATAAAATGAATGCAATTGTTGTTGTTAACTTGTTTATTGCAGCTTATAA

TGGTTACAAATAAAGCAATAGCATCACAAATTTCACAAATAAAGCATTTT

TTTCACTGCATTCTAGTTGTGGTTTGTCCAAAC

SEQUENCE LISTING SEQ. ID NO: 6:
Primer C

SEQUENCE LISTING SEQ. ID NO: 7:
Primer D

SEQUENCE LISTING SEQ. ID NO: 8:
Human γ-chain gene joining double-
stranded DNA fragment
CGTGGAACTCAGGCGCCCTGACCAGCGGCGTGCACACCTTCCCGGCTGTC

CTACAGTCCTCAGGACTCTACTCCCTCAGCAGCGTGGTGACCGTGCCCTCC

-continued

AGCAGCTTGGGCACCCAGACCTACACCTGCAACGTGAATCACAAGCCCAGC

AACACCAAGGTGGACAAGAGAGTTGAGCCCAAATCTTGTGACAAAACTCAC

ACATGCCCACCGTGCCCAGCACCTGAACTCCTGGGGGGACCGTCAGTCTT

CCTCTTCCCCCCAAAACCCAAGGACACCCTCATGATCTCCCGGACCCCTGA

GGTCACATGCGTGGTGGTGGACGTGAGCCACGAAGACCCTGAGGTCAAGT

TCAACTGGTACGTGGACGGCGTGGAGGTGCATAATGCCAAGACAAAGCCG

CGGGAGGAGCAGTACAACAGCACGTACCGTGTGGTCAGCGTCCTCACCGT

CCTGCACCAGGACTGGCTGAATGGCAAGGAGTACAAGTGCAAGGTCTCCAA

CAAAGCCCTCCCAGCCCCCATCGAGAAAACCATCTCCAAAGCCAAAGGGCA

GCCCCGAGAACCACAGGTGTACACCCTGCCCCCATCCCGGGATGAGCTGA

CCAAGAACCAGGTCAGCCTGACCTGCCTGGTCAAAGGCTTCTATCCCAGCG

ACATCGCCGTGGAGTGGGAGAGCAATGGGCAGCCGGAGAACAACTACAAG

ACCACGCCTCCCGTGCTGGACTCCGACGGCTCCTTCTTCCTCTACAGCAAG

CTCACCGTGGACAAGAGCAGGTGGCAGCAGGGGAACGTCTTCTCATGCTC

CGTGATGCATGAGGGTCTGCACAACCACTACACGCAGAAGAGCCTCTCCC

TGTCTCCGGGTAAATGAGTGCGACGGCGGCCAAGTCGACTTGGCCGACTC

TAGATCATAATCAGCCATACCACATTTGTAGAGGTTTTACTTGCTTTAAA

AAACCTCCCACACCTCCCCCTGAACCTGAAACATAAAATGAATGCAATTG

TTGTTGTTAACTTGTTTATTGCAGCTTATAATGGTTACAAATAAAGCAAT

AGCATCACAAATTTCACAAATAAAGCATTTTTTTCACTGCATTCTAGTTG

TGGTTTGTCCAAACTAGTTATTAATAGTAATCAATTACGGGGTCATTAGT

TCATAGCCCATATATGGAGTTCCGCGTTACATAACTTACGGTAAATGGCC

CGCCTGGCTGACCGCCCAACGACCCCGCCCATTGACGTCAATAATGACG

TATGTTCCCATAGTAACGCCAATAGGGACTTTCCATTGACGTCAATGGGT

GGAGTATTTACGGTAAACTGCCCACTTGGCAGTACATCAAGTGTATCATA

TGCCAAGTACGCCCCCTATTGACGTCAATGACGGTAAATGGCCCGCCTGG

CATTATGCCCAGTACATGACCTTATGGGACTTTCCTACTTGGCAGTACAT

CTACGTATTAGTCATCGCTATTACCATGGTGATGCGGTTTTGGCAGTACA

TCAATGGGCGTGGATAGCGGTTTGACTCACGGGGATTTCCAAGTCTCCAC

CCCATTGACGTCAATGGGAGTTTGTTTTGGCACCAAAATCAACGGGACTT

TCCAAAATGTCGTAACAACTCCGCCCCATTGACGCAAATGGGCGGTAGGC

GTGTACGGTGGGAGGTCTATATAAGCAGAGCTGGTTTAGTGAACCGTCAG

ATCCGCTAGCGCTACCGGACTCAGATCTCGAGCTCAAGCTTCGAATTCTG

CAGTCGACGGTACCGCGGGCCCGGGATCCCCCCCCCCCC

SEQUENCE LISTING SEQ. ID NO: 9:
Primer E

SEQUENCE LISTING SEQ. ID NO: 10:
Primer F

SEQUENCE LISTING SEQ. ID NO: 11:
Primer G

SEQUENCE LISTING SEQ. ID NO: 12:
Primer H

SEQUENCE LISTING SEQ. ID NO: 13:
Primer I

SEQUENCE LISTING SEQ. ID NO: 14:
Primer J

SEQUENCE LISTING SEQ. ID NO: 15:
Primer K

SEQUENCE LISTING SEQ. ID NO: 16:
Primer L

SEQUENCE LISTING SEQ. ID NO: 17:
Primer M

SEQUENCE LISTING SEQ. ID NO: 18:
Primer pMiniCMV-hIgK

TAGTTATTAATAGTAATCAATTACGGGGTCATTAGTTCATAGCCCATATAT

GGAGTTCCGCGTTACATAACTTACGGTAAATGGCCCGCCTGGCTGACCGCC

CAACGACCCCGCCCATTGACGTCAATAATGACGTATGTTCCCATAGTAAC

GCCAATAGGGACTTTCCATTGACGTCAATGGGTGGAGTATTTACGGTAAAC

TGCCCACTTGGCAGTACATCAAGTGTATCATATGCCAAGTACGCCCCCTAT

TGACGTCAATGACGGTAAATGGCCCGCCTGGCATTATGCCCAGTACATGAC

CTTATGGGACTTTCCTACTTGGCAGTACATCTACGTATTAGTCATCGCTAT

TACCATGGTGATGCGGTTTTGGCAGTACATCAATGGGCGTGGATAGCGGTT

TGACTCACGGGGATTTCCAAGTCTCCACCCCATTGACGTCAATGGGAGTTT

GTTTTGGCACCAAAATCAACGGGACTTTCCAAAATGTCGTAACAACTCCGC

CCCATTGACGCAAATGGGCGGTAGGCGTGTACGGTGGGAGGTCTATATAAG

CAGAGCTGGTTTAGTGAACCGTCAGATCCGCTAGCGCTACCGGACTCAGAT

CTCGAGCTCAAGCTTCGAATTCTGCAGTCGACGGTACCGCGGGCCCGGGAT

CCCCCCCCCCCCGATATCTAAATACATTCAAATATGTATCCGCTCATGAG

ACAATAACCCTGATAAATGCTTCAATAATATTGAAAAAGGAAGAGTATGAG

TATTCAACATTTCCGTGTCGCCCTTATTCCCTTTTTTGCGGCATTTTGCCT

TCCTGTTTTTGCTCACCCAGAAACGCTGGTGAAAGTAAAAGATGCTGAAGA

TCAGTTGGGTGCACGAGTGGGTTACATCGAACTGGATCTCAACAGCGGTAA

GATCCTTGAGAGTTTTCGCCCCGAAGAACGTTTTCCAATGATGAGCACTTT

TAAAGTTCTGCTATGTGGCGCGGTATTATCCCGTATTGACGCCGGGCAAGA

GCAACTCGGTCGCCGCATACACTATTCTCAGAATGACTTGGTTGAGTACTC

ACCAGTCACAGAAAAGCATCTTACGGATGGCATGACAGTAAGAGAATTATG

CAGTGCTGCCATAACCATGAGTGATAACACTGCGGCCAACTTACTTCTGAC

AACGATCGGAGGACCGAAGGAGCTAACCGCTTTTTTGCACAACATGGGGGA

TCATGTAACTCGCCTTGATCGTTGGGAACCGGAGCTGAATGAAGCCATACC

AAACGACGAGCGTGACACCACGATGCCTGTAGCAATGGCAACAACGTTGCG

CAAACTATTAACTGGCGAACTACTTACTCTAGCTTCCCGGCAACAATTAAT

AGACTGGATGGAGGCGGATAAAGTTGCAGGACCACTTCTGCGCTCGGCCCT

TCCGGCTGGCTGGTTTATTGCTGATAAATCTGGAGCCGGTGAGCGTGGGTC

TCGCGGTATCATTGCAGCACTGGGGCCAGATGGTAAGCCCTCCCGTATCGT
AGTTATCTACACGACGGGGAGTCAGGCAACTATGGATGAACGAAATAGACA
GATCGCTGAGATAGGTGCCTCACTGATTAAGCATTGGTAACTGTCAGACCA
AGTTTACTCATATATACTTTAGATTGATTTAAAACTTCATTTTTAATTTAA
AAGGATCTAGGTGAAGATCCTTTTTGATAATCTCATGACCAAAATCCCTTA
ACGTGAGTTTTCGTTCCACTGAGCGTCAGACCCCGTAGAAAAGATCAAAGG
ATCTTCTTGAGATCCTTTTTTTCTGCGCGTAATCTGCTGCTTGCAAACAAA
AAAACCACCGCTACCAGCGGTGGTTTGTTTGCCGGATCAAGAGCTACCAAC
TCTTTTTCCGAAGGTAACTGGCTTCAGCAGAGCGCAGATACCAAATACTGT
TCTTCTAGTGTAGCCGTAGTTAGGCCACCACTTCAAGAACTCTGTAGCACC
GCCTACATACCTCGCTCTGCTAATCCTGTTACCAGTGGCTGCTGCCAGTGG
CGATAAGTCGTGTCTTACCGGGTTGGACTCAAGACGATAGTTACCGGATAA
GGCGCAGCGGTCGGGCTGAACGGGGGGTTCGTGCACACAGCCCAGCTTGGA
GCGAACGACCTACACCGAACTGAGATACCTACAGCGTGAGCTATGAGAAAG
CGCCACGCTTCCCGAAGGGAGAAAGGCGGACAGGTATCCGGTAAGCGGCAG
GGTCGGAACAGGAGAGCGCACGAGGGAGCTTCCAGGGGGAAACGCCTGGTA
TCTTTATAGTCCTGTCGGGTTTCGCCACCTCTGACTTGAGCGTCGATTTTT
GTGATGCTCGTCAGGGGGCGGAGCCTATGGAAAAACGCCAGCAACGCGGC
CTTTTTACGGTTCCTGGCCGATATCACGTGCGCATCTTCCCGCCATCTGAT
GAGCAGTTGAAATCTGGAACTGCCTCTGTTGTGTGCCTGCTGAATAACTTC
TATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTAC
AGCCTCAGCAGCACCCTGACGCTGAGCAAAGCAGACTACGAGAAACACAAA
GTCTACGCCTGCGAAGTCACCCATCAGGGCCTGAGCTCGCCCGTCACAAAG
AGCTTCAACAGGGGAGAGTGTTAGAGGGAGAAGTGCGGCCAAGTCGACTTG
GCCGACTCTAGATCATAATCAGCCATACCACATTTGTAGAGGTTTTACTTG
CTTTAAAAAACCTCCCACACCTCCCCCTGAACCTGAAACATAAAATGAATG
CAATTGTTGTTGTTAACTTGTTTATTGCAGCTTATAATGGTTACAAATAAA
GCAATAGCATCACAAATTTCACAAATAAAGCATTTTTTTCACTGCATTCTA
GTTGTGGTTTGTCCAAAC

SEQUENCE LISTING SEQ. ID NO: 19:
Human κ-chain gene joining double-stranded DNA
fragment
CATCTTCCCGCCATCTGATGAGCAGTTGAAATCTGGAACTGCCTCTGTTGT
GTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGA
CAGCAAGGACAGCACCTACAGCCTCAGCAGCACCCTGACGCTGAGCAAAGC
AGACTACGAGAAACACAAAGTCTACGCCTGCGAAGTCACCCATCAGGGCCT
GAGCTCGCCCGTCACAAAGAGCTTCAACAGGGGAGAGTGTTAGAGGGAGAA
GTGCGGCCAAGTCGACTTGGCCGACTCTAGATCATAATCAGCCATACCACA
TTTGTAGAGGTTTTACTTGCTTTAAAAAACCTCCCACACCTCCCCCTGAAC
CTGAAACATAAAATGAATGCAATTGTTGTTGTTAACTTGTTTATTGCAGCT
TATAATGGTTACAAATAAAGCAATAGCATCACAAATTTCACAAATAAAGCA
TTTTTTTCACTGCATTCTAGTTGTGGTTTGTCCAAACTAGTTATTAATAGT
AATCAATTACGGGGTCATTAGTTCATAGCCCATATATGGAGTTCCGCGTTA
CATAACTTACGGTAAATGGCCCGCCTGGCTGACCGCCCAACGACCCCCGCC
CATTGACGTCAATAATGACGTATGTTCCCATAGTAACGCCAATAGGGACTT
TCCATTGACGTCAATGGGTGGAGTATTTACGGTAAACTGCCCACTTGGCAG
TACATCAAGTGTATCATATGCCAAGTACGCCCCCTATTGACGTCAATGACG
GTAAATGGCCCGCCTGGCATTATGCCCAGTACATGACCTTATGGGACTTTC
CTACTTGGCAGTACATCTACGTATTAGTCATCGCTATTACCATGGTGATGC
GGTTTTGGCAGTACATCAATGGGCGTGGATAGCGGTTTGACTCACGGGGAT
TTCCAAGTCTCCACCCCATTGACGTCAATGGGAGTTTGTTTTGGCACCAAA
ATCAACGGGACTTTCCAAAATGTCGTAACAACTCCGCCCCATTGACGCAAA
TGGGCGGTAGGCGTGTACGGTGGGAGGTCTATATAAGCAGAGCTGGTTTAG
TGAACCGTCAGATCCGCTAGCGCTACCGGACTCAGATCTCGAGCTCAAGCT
TCGAATTCTGCAGTCGACGGTACCGCGGGCCCGGGATCCCCCCCCCCCC

The invention claimed is:

1. A method for producing a joined DNA fragment in which joining DNA regions have been joined on both ends of a target gene, comprising:

(1) providing a double-stranded gene fragment comprising a target gene sequence as a template; amplifying the template to produce a 3' end protruding double-stranded gene fragment containing a target gene having associative regions on the two termini of the target gene, the two associative regions having base sequences that do not mutually associate, the base sequence of one or both of the associative regions being a base sequence contained in the target gene with a protruding sequence of one or more nucleotides being present on the 3' ends of both of the associative regions joined to a 3' end protruding double-stranded gene fragment containing a non-target gene;

(2) providing a double-stranded DNA joining fragment, containing a joining region, and having associative regions on the two termini of the joining DNA region; wherein (a) one of the associative regions of the 3' end protruding double-stranded gene fragment is comprised of a base sequence that is homologous with the associative region of one terminus of the double-stranded joining DNA fragment, with the sequence on the terminus to which the 3' protruding end has been added being the side that connects to the joining DNA region in one of the associative regions of the double-stranded joining DNA fragment;

(b) the protruding sequence from the one associative region of the 3' end protruding double-stranded gene fragment does not have a strand-elongating function in a DNA synthesis reaction;

(c) the other associative region of the 3' end protruding double-stranded gene fragment is comprised of a base sequence that is homologous with the associative region of the other terminus of the double-stranded joining DNA fragment, with the sequence on the terminus to which the 3' protruding end has been added being the side that connects to the joining DNA region in the other of the associative regions of the double-stranded joining DNA fragment;

(d) the protruding sequence from the other associative region of the 3' end protruding double-stranded gene fragment does not have a strand-elongating function in the DNA synthesis reaction; and (3) subjecting the product of step 1 and the double-stranded joining DNA fragment to at least two cycles of a thermal denaturation, re-association, and DNA synthesis reaction to obtain a joined DNA fragment in which joining DNA regions have been joined on both ends of a target gene while suppressing generation of a joined DNA fragment in which joining DNA regions have been joined on both ends of a non-target gene, without a purification step for removal of the 3' end protruding double-stranded gene fragment containing a non-target gene from the 3' end protruding double-stranded gene fragment containing a target gene sequence; wherein the method for producing the joined DNA fragment does not employ chimeric RNA/DNA primers and wherein the method for producing the joined DNA fragment produces a joined DNA fragment in which joining DNA regions are joined to both sides of a target gene, the joined DNA fragment comprising:

(A) a target gene sequence, comprising associative regions on each of the two termini of the target gene sequence, the two associative regions comprising mutually non-associative base sequences, the base sequence of one or both of the regions being a base sequence contained in the target gene sequence, and both of the associative regions having protruding sequences of one or more nucleotides on the 3' ends thereof; and (B) double-stranded joining DNA fragments comprising a joining DNA region, and having associative regions on each terminus of the joining DNA region, respectively.

2. The production method according to claim 1, wherein the product formed comprises, in order, second associative region-joining DNA region-first associative region-target gene region-second associative region-joining DNA region-first associative region.

3. The production method according to claim 1, wherein the joining DNA region is comprised of a first and a second joining DNA region in the form of a sequence A and a sequence B; one of the associative regions of the 3' end protruding double-stranded gene fragment, from the terminus of the associative region, is comprised of sequences P2 and T2; the other associative region of the 3' end protruding double-stranded gene fragment, from the terminus of the associative region, is comprised of sequences P1 and T1; at least one of sequence T1 or sequence T2 comprises a base sequence that is contained in a target gene sequence; one of the associative regions of the double-stranded joining DNA fragment comprises, from the terminus of the associative region, sequences VP1 and VT1; the other, from the terminus of the associative region comprises sequences VP2 and VT2; sequences VP1 and VT1 comprise base sequences that are homologous with sequences P1 and T1, respectively; and sequences VP2 and VT2 have base sequences that are homologous with sequences P2 and T2, respectively.

4. The production method according to claim 3, wherein the 3' end protruding double-stranded gene fragment is denoted by P1-T1-target gene-T2-P2; the double-stranded joining DNA fragment is denoted by VT2-VP2-sequence B-sequence A-VP1-VT1; the joined DNA fragment is a DNA fragment comprising at least one unit of VT2-VP2(T2-P2)-sequence B-sequence A-VP1-VT1(P1-T1)-target gene-VT2-VP2(T2-P2)-sequence B-sequence A-VP1-VT1 (P1-T1); where VT2-VP2(T2-P2) means VT2-VP2 that is homologous with T2-P2; and where VP1-VT1(P1-T1) means VT1-VP1 that is homologous with T1-P1.

5. The production method according to claim 3, wherein the sequence without a strand-elongating function in the reaction synthesizing the DNA with a protruding end on the 3' end of sequence P2 is a sequence that is not homologous with the sequence adjacent to VP2 of sequence B, and the sequence without a strand- elongating function in the reaction synthesizing the DNA with a protruding end on the 3' end of sequence P1 is a sequence that is not homologous with the sequence adjacent to VP1 of sequence A.

6. The production method according to claim 1, wherein the protruding ends are sequences containing at least one dideoxynucleotide on the 3' ends thereof.

7. A method for producing a DNA fragment comprising at least one joining DNA region and the entire sequence of a target gene, comprising:
conducting polymerase chain reaction, with a joined DNA fragment produced by the method according to claim 1 as template, using a forward primer and a reverse primer functioning in different joining DNA regions contained in a joined DNA fragment to amplify of at least one joining DNA region and the entire sequence of a target gene contained in the joined DNA fragment.

8. A method for producing a DNA fragment, comprising conducting PCR employing a forward primer contained on the 3' end of the base sequence of sequence A toward a target gene and employing a reverse primer contained on the 3' end of the base sequence of sequence B toward the target gene with the joined DNA fragment produced by the method according to claim 3 as template to obtain a DNA fragment in which sequence A, the sequence of the target gene, and sequence B are joined.

9. A method for producing a joined DNA fragment in which a joining DNA region 1 has been joined on one side of a target gene and a joining DNA region 2 has been joined on the other side thereof, comprising:

(1) providing a double-stranded gene fragment comprising a target gene sequence as a template, amplifying the template to produce a product comprising a 3' end protruding double-stranded gene fragment containing a target gene having associative regions on the two termini of the target gene, the two associative regions having base sequences that do not mutually associate, the base sequence of one or both of the regions being a base sequence contained in the target gene, the two associative regions having base sequences that do not mutually associate, the base sequence of one or both of the regions being a base sequence contained in the target gene at least as a part of the target gene, with a protruding sequence of one or more nucleotides being present on the 3' ends of both of the associative regions joined to a 3' end protruding double-stranded gene fragment containing a non-target gene;

(2) providing a double-stranded joining DNA fragment 1 that comprises a joining DNA region 1 and a terminal associative region and a double-stranded joining DNA fragment 2 that comprises a joining DNA region 2 and a terminal associative region; wherein (a) one of the associative regions of the 3' end protruding double-stranded gene fragments is comprised of a base sequence that is homologous with the associative region of the double-stranded joining DNA fragment 1, but with the sequence on the terminus terminal associative region of the joining fragment to which the 3' protruding end is added, being the side that connects with the joining DNA region in the associative region of double-stranded joining DNA fragment 1;

(b) the protruding sequence from one of the associative regions of the 3' end protruding double-stranded gene fragment does not have a strand-elongating function in a DNA synthesis reaction;

(c) the other associative region of the 3' end protruding double-stranded gene fragment is comprised of a base sequence that is homologous with the associative region of the terminus of double-stranded joining DNA fragment 2, with the sequence on the terminus to which the 3' protruding end has been added being the side that connects to the joining DNA region in the associative region of the double-stranded joining DNA fragment 2;

(d) the protruding sequence from the other associative region of the 3' end protruding double-stranded gene fragment does not have a strand-elongating function in the DNA synthesis reaction; and (3) subjecting the product of step 1 and double-stranded joining DNA fragments 1 and 2 to at least two cycles of a thermal denaturation, re-association, and DNA synthesis reaction to obtain a joined DNA fragment in which joining DNA regions have been joined on both ends of a target gene while suppressing generation of a joined DNA fragment in which joining DNA regions have been joined on both ends of a non-target gene without a purification step for removal of the 3' end protruding double-stranded gene fragment containing a non-target gene from the 3' end protruding double-stranded gene fragment containing a target gene sequence; wherein the method for producing the joined DNA fragment does not employ chimeric RNA/DNA primers and wherein the method for producing the joined DNA fragment produces a joined DNA fragment in which a joining DNA region 1 has been joined to one side of a target gene and a joining DNA region 2 has been joined to the other side thereof comprising:
(A) a 3' end protruding double-stranded gene fragment containing a target gene, having associative regions on the two termini of the target gene, the two associative regions having base sequences that do not mutually associate, the base sequence of one or both of the regions being a base sequence contained in the target gene, with protruding sequences of one or more nucleotides being present on the 3' ends of both of the associative regions, that is obtained from a double-stranded gene fragment comprising a target gene sequence; and
(B) a double-stranded joining DNA fragment 1, comprising a terminal associative region and containing a joining DNA region 1 and a double-stranded joining DNA fragment 2, comprising a terminal associative region and containing a joining DNA region 2, respectively.

10. The production method according to claim 9, wherein joining DNA region 1 contains sequence A and joining DNA region 2 contains sequence B, one of the associative regions of the 3' protruding double-stranded gene fragment comprises, from the terminus of the associative region, sequences P1 and T1, and the other comprises, from the terminus of the associative region, sequences P2 and T2, where at least one of sequence T1 and sequence T2 comprises a base sequence containing the target gene sequence, the associative region of double-stranded joining DNA fragment 1 comprises, from the terminus, sequences VT1 and VP1, the associative region of double-stranded joining DNA fragment 2 comprises, from the terminus, sequences VT2 and VP2, sequences VP1 and VT1 comprise base sequences that are homologous with sequences P1 and T1, respectively, and sequences VP2 and VT2 comprise base sequences that are homologous with sequences P2 and T2, respectively.

11. The production method according to claim 10 wherein the 3' end protruding double-stranded gene fragment is denoted by P1-T1-target gene-T2-P2, double-stranded joining DNA fragment 1 is denoted by the sequence A-VP1-VT1, double-stranded joining DNA fragment 2 is denoted by VT2-VP2-sequence B, the joined DNA fragment comprises at least one unit of sequence A-VP1-VT1(P1-T1)-target gene-VT2-VP2(T2-P2)-sequence B, where VT2-VP2(T2-P2) means VT2-VP2 that is homologous with T2-P2 and VP1-VT1(P1-T1) means VT1-VP1 that is homologous with
  T1-P1.

12. The production method according to claim 10, wherein the sequence without a strand-elongating function in the reaction synthesizing the DNA with a protruding end on the 3' end of sequence P2 is a sequence that is not homologous with the sequence adjacent to VP2 of sequence B, and the sequence without a strand- elongating function in the reaction synthesizing the DNA with a protruding end on the 3' end of sequence P1 is a sequence that is not homologous with the sequence adjacent to VP1 of sequence A.

13. The production method according to claim 9, wherein the protruding ends are sequences containing at least one dideoxynucleotide on the 3' ends thereof.

14. A method for producing a DNA fragment comprising at least one joining DNA region and the entire sequence of a target gene, comprising:
conducting polymerase chain reaction with the joined DNA prepared by the method according to claim 9 as template, using a set of primers for amplifying at least one joining DNA region and the entire sequence of a target gene contained in the joined DNA fragment.

15. A method for producing a DNA fragment, comprising conducting PCR employing a forward primer contained on the 3' end a portion of the base sequence of a first sequence toward a target gene and employing a reverse primer contained on the 3' end a portion of the base sequence of a second sequence toward the target gene using the joined DNA fragment produced by the method according to claim 10 as template to obtain a DNA fragment in which the first sequence, the sequence of the target gene, and the second sequence are joined.

16. A method for producing a single-side joined DNA fragment in which a joining DNA region has been joined on one side of a target gene, comprising:
(1) providing a double-stranded gene fragment comprising a target gene sequence as a template; amplifying the template to produce a 3' end protruding double-stranded gene fragment comprising an associative region on the side of one terminus of the target gene sequence having a base sequence contained in the target gene sequence, and there being a protruding sequence of one or more nucleotides on the 3' end of the associative region joined to a 3' end protruding double-stranded gene fragment containing a non-target gene;
(2) providing a double-stranded joining DNA fragment comprising a joining DNA region and having a terminal associative region; wherein
(a) one of the associative regions of the 3' end protruding double-stranded gene fragments is comprised of a base sequence that is homologous with the associative region of the double-stranded joining DNA fragment, but with the sequence on the side of the terminus on which the 3' protruding end is added being the side that connects with the joining DNA region in the associative region of the double-stranded joining DNA fragment;
(b) the protruding sequence from one of the associative regions of the 3' end protruding double-stranded gene fragment does not have a strand-elongating function in a DNA synthesis reaction; and
(3) subjecting the product of step 1 to one cycle of a thermal denaturation, re-association, and DNA synthesis reaction to obtain a hetero double-stranded DNA product, and then employing the hetero double-stranded DNA product as template to conduct a polymerase chain reaction and obtain a single-sided joined DNA fragment in which joining DNA regions have been joined on both ends of a target gene while suppressing generation of a joined DNA fragment in which a joining DNA region has been joined on one end of a non-target gene without a purification step for removal of the 3' end protruding double-stranded gene fragment containing a non-target gene from the 3' end protruding double-stranded gene fragment containing a target gene sequence; wherein the method for producing the joined DNA fragment does not employ chimeric RNA/DNA primers and wherein the method for producing the joined DNA fragment produces a single-sided joined DNA fragment in which a joining DNA region has been joined on one side of a target gene comprising:

(A) a target gene sequence, having an associative region on the side of one terminus of the target gene sequence, the base sequence of this region being a base sequence contained in the target gene sequence, and with a protruding sequence of one or more nucleotides being present on the 3' end of the associative region; wherein the 3' end protruding double-stranded gene fragment containing a target gene is covalently linked to a 3' end protruding double-stranded gene fragment containing a non-target gene; and (B) a double-stranded joining DNA fragment comprising a joining DNA region and having a terminal associative region respectively.

17. The production method according to claim 16, wherein the joining DNA region comprises sequence A; the associative region of the 3' end protruding double-stranded gene fragment comprises, from the terminus, sequences P1 and T1; sequence T1 comprises a base sequence contained in the target gene sequence; the associative region of the double-stranded joining DNA fragment comprises, from the terminal side, sequences VT1 and VP1; sequences VP1 and VT1 have base sequences that are homologous with sequences P1 and T1, respectively; and a primer contained on the 3' end so as to cause a portion of the target gene of the hetero double-stranded DNA product to orient toward the protruding sequence side of the target gene and a primer contained on the 3' end so as to cause a portion of sequence A of the hetero double-stranded DNA product to orient toward the target gene side are employed in the polymerase chain reaction utilizing the hetero two-stranded DNA product as template.

18. The production method according to claim 17, wherein the 3' end protruding double-stranded gene fragment is denoted by P1-T1-target gene; the double-stranded joining DNA fragment is denoted by sequence A-VP1-VT1; the single-side joined DNA fragment is a DNA fragment comprising at least one sequence A-VP1-VT1(P1-T1)-target gene; and VP1-VT1(P1-T1) means VT1-VP1 that is homologous with T1-P1.

19. The production method according to claim 17, wherein the sequence not having a strand-elongating function in the DNA synthesis reaction of the protruding end on the 3' end of sequence P1 is a sequence that is not homologous when adjacent to VP 1 of sequence A.

20. The production method according to claim 16, wherein the protruding sequence is a sequence containing a dideoxynucleotide on the 3' end thereof.

21. The production method according to claim 3, further comprising causing deoxynucleotide terminal transferase to act upon the polydeoxynucleotide and double-stranded DNA fragment containing the sequence of the target gene to obtain a 3' end protruding double-stranded gene fragment comprising the sequence of the target gene wherein the double-stranded DNA fragment containing the target gene sequence comprises sequence P1 and sequence P2 on the ends thereof, sequence T1 is present within sequence P1, sequence T2 is present within sequence P2, and one or both of sequences T1 and T2 comprise a base sequence that is included within the target gene.

22. The production method according to claim 17, further comprising causing deoxynucleotide terminal transferase to act upon the polydeoxynucleotide and double-stranded DNA fragment containing the sequence of the target gene to obtain a 3' end protruding double-stranded gene fragment comprising the sequence of the target gene wherein sequence P1 is present on one terminus of the double-stranded DNA fragment containing the target gene sequence and sequence T1 is present within sequence P1, and sequence T1 comprises a base sequence that is included within the target gene.

23. The production method according to claim 3, wherein one or both of sequence T1 and sequence T2 comprise a base sequence that is included within the target gene.

24. The production method according to claim 3, wherein one or both of sequence P1 and sequence P2 comprise a base sequence that is included within the target gene.

25. The production method according to claim 3, wherein each of sequences P1 and P2 is comprised of 10 or more bases.

26. The production method of claim 3, wherein the target gene is an antibody gene or a T cell receptor gene, the 3' end protruding double-stranded gene fragment contains a sequence of antibody gene or T cell receptor gene, and region VP1 and region VT1 in the double-stranded joining DNA fragment comprising the double-stranded joining DNA comprise sequences that are from an antibody gene or a T cell receptor gene.

27. The production method according to claim 26, wherein the target gene is an antibody gene or a T cell receptor gene, the 3' end protruding double-stranded gene fragment contains a sequence of the antibody gene or T cell receptor gene, and region VP2 and region VT2 in the double-stranded joining DNA fragment having the double-stranded joining DNA fragment are sequences that are, or are not, obtained from antibody genes or T cell receptor genes.

28. A method for producing an antibody or T cell receptor employing joined DNA prepared by the method according to claim 26, comprising expressing the joined DNA in an expression system to produce the antibody or T cell receptor.

29. The production method according to claim 1, wherein the double-stranded gene fragment accompanies as a contaminant in the result of step (1) a gene fragment comprising a non-target gene, primers used to amplify the double-stranded gene fragment in polymerase chain reaction or both of them, and the joined DNA fragment in which joining DNA regions join to both sides of a target gene is obtained in step (4) without production of a nonspecific joining DNA fragment in which joining DNA regions join to both sides of a non-target gene.

30. The production method according to claim 9, wherein the double-stranded gene fragment accompanies as a contaminant in the result of step (1) a gene fragment comprising a non-target gene, primers used to amplify the double-stranded gene fragment in polymerase chain reaction or both of them, and the joined DNA fragment in which joining DNA regions join to both sides of a target gene is obtained in step (4) without production of a nonspecific joining DNA fragment in which joining DNA regions join to both sides of a non-target gene.

31. The production method according to claim 16, wherein the double-stranded gene fragment accompanies as a contaminant in the result of step (1) a gene fragment comprising a non-target gene, primers used to amplify the double-stranded gene fragment in polymerase chain reaction or both of them, and the joined DNA fragment in which joining DNA regions join to both sides of a target gene is obtained in step (4) without production of a nonspecific joining DNA fragment in which joining DNA regions join to both sides of a non-target gene.

* * * * *